United States Patent [19]
Njoroge et al.

[11] Patent Number: 5,994,364
[45] Date of Patent: Nov. 30, 1999

[54] TRICYCLIC ANTITUMOR FARNESYL PROTEIN TRANSFERASE INHIBITORS

[75] Inventors: F. George Njoroge, Union; Ronald J. Doll, Maplewood; Stacy W. Remiszewski, Washington Township, all of N.J.

[73] Assignee: Schering Corporation, Kenilworth, N.J.

[21] Appl. No.: 08/927,467

[22] Filed: Sep. 11, 1997

Related U.S. Application Data

[60] Provisional application No. 60/025,872, Sep. 13, 1996, and provisional application No. 60/049,848, Jun. 17, 1997.

[51] Int. Cl.⁶ .................... A61K 31/435; C07D 221/06
[52] U.S. Cl. ............................. 514/290; 546/93
[58] Field of Search ................ 514/290; 546/93

[56] References Cited

U.S. PATENT DOCUMENTS

| | | | |
|---|---|---|---|
| 4,826,853 | 5/1989 | Piwinski et al. | 514/290 |
| 5,089,496 | 2/1992 | Piwinski et al. | 514/253 |
| 5,151,423 | 9/1992 | Piwinski et al. | 514/254 |
| 5,393,890 | 2/1995 | Syoji et al. | 546/80 |
| 5,661,152 | 8/1997 | Bishop et al. | 514/254 |
| 5,672,611 | 9/1997 | Doll et al. | 514/325 |
| 5,684,013 | 11/1997 | Afonso et al. | 514/290 |
| 5,696,121 | 12/1997 | Bishop et al. | 514/254 |
| 5,700,806 | 12/1997 | Doll et al. | 514/290 |
| 5,703,090 | 12/1997 | Afonso et al. | 514/290 |
| 5,712,280 | 1/1998 | Doll et al. | 514/253 |
| 5,714,609 | 2/1998 | Bishop et al. | 546/93 |
| 5,719,148 | 2/1998 | Bishop et al. | 514/228.2 |
| 5,721,236 | 2/1998 | Bishop et al. | 514/255 |
| 5,728,703 | 3/1998 | Bishop et al. | 514/254 |

FOREIGN PATENT DOCUMENTS

| | | |
|---|---|---|
| 0270818 | 6/1988 | European Pat. Off. |
| 0396083 | 11/1990 | European Pat. Off. |
| 0495484 | 7/1992 | European Pat. Off. |
| WO95/10515 | 4/1995 | WIPO |
| WO95/10516 | 4/1995 | WIPO |
| WO95/15949 | 6/1995 | WIPO |
| WO96/31478 | 10/1995 | WIPO |
| WO96/30018 | 10/1996 | WIPO |
| WO96/30362 | 10/1996 | WIPO |
| WO96/30363 | 10/1996 | WIPO |
| WO96/31477 | 10/1996 | WIPO |
| WO97/23478 | 7/1997 | WIPO |

OTHER PUBLICATIONS

Bishop et al., The Journal of Biological Chemistry, vol. 270, No. 15, pp. 30611–30618 (1995).
Njoroge et al., Bioorganic & Medicinal Chemistry Letters, vol. 6, No. 24, pp. 2977–2982 (1996).

*Primary Examiner*—John Kight
*Assistant Examiner*—Charanjit S. Aulakh
*Attorney, Agent, or Firm*—Henry C. Jeanette

[57] ABSTRACT

The invention relates to compounds of the formula

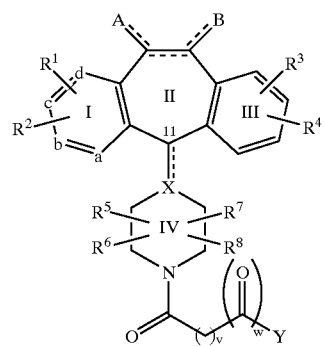

(1.0)

wherein $R^1$, $R^2$, $R^3$, $R^4$, $R^5$, $R^6$, $R^7$, $R^8$, Y, A, B, X, a, b, c, d, v, and w are as described herein. The compounds of formula (1.0) are useful for inhibiting tumor growth.

19 Claims, No Drawings

TRICYCLIC ANTITUMOR FARNESYL PROTEIN TRANSFERASE INHIBITORS

REFERENCE TO RELATED APPLICATIONS

This application claims the benefit of U.S. Provisional Application 60/025,872 filed Sep. 13, 1996, and U.S. Provisional application 60/049,848 filed Jun. 17, 1997.

SUMMARY OF THE INVENTION

This invention relates to compounds of the formula (1.0):

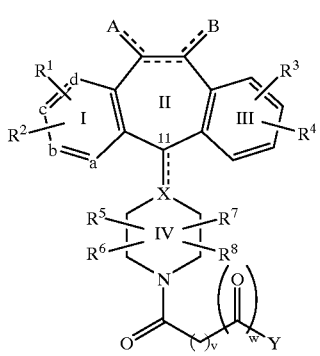

(1.0)

wherein:

X is N, CH, or C when the double bond is present at the C-11 position;

one of a, b, c and d represents N or $NR^9$ wherein $R^9$ is $O^-$, $-CH_3$ or $-(CH_2)_nCO_2H$ wherein n is 1 to 3, and the remaining a, b, c and d groups represent $CR^1$ or $CR^2$; or each of a, b, c, and d are independently selected from $CR^1$ or $CR^2$;

each $R^1$ and each $R^2$ is independently selected from H, halo, $-CF_3$, $-OR^{10}$ (e.g., $-OCH_3$), $-COR^{10}$, $-SR^{10}$ (e.g., $-SCH_3$ and $-SCH_2C_6H_5$), $-S(O)_tR^{11}$ (wherein t is 0, 1 or 2, e.g., $-SOCH_3$ and $-SO_2CH_3$), $-SCN$, $-N(R^{10})_2$, $-NR^{10}R^{11}$, $-NO_2$, $-OC(O)R^{10}$, $-CO_2R^{10}$, $-OCO_2R^{11}$, $-CN$, $-NHC(O)R^{10}$, $-NHSO_2R^{10}$, $-CONHR^{10}$, $-CONHCH_2CH_2OH$, $-NR^{10}COOR^{11}$,

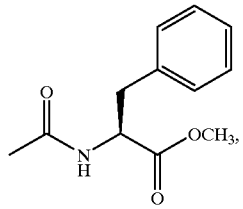

$-SR^{11}C(O)OR^{11}$ (e.g., $-SCH_2CO_2CH_3$), $-SR^{11}N(R^{12})_2$ wherein each $R^{12}$ is independently selected from H and $-C(O)OR^{11}$ (e.g., $-S(CH_2)_2NHC(O)O$-t-butyl and $-S(CH_2)_2NH_2$), benzotriazol-1-yloxy, tetrazol-5-ylthio, or substituted tetrazol-5-ylthio (e.g., alkyl substituted tetrazol-5-ylthio such as 1-methyl-tetrazol-5-ylthio), alkynyl, alkenyl or alkyl, said alkyl or alkenyl group optionally being substituted with halo, $-OR^{10}$ or $-CO_2R^{10}$;

$R^3$ and $R^4$ are the same or different and each independently represents H, any of the substituents of $R^1$ and $R^2$, or $R^3$ and $R^4$ taken together represent a saturated or unsaturated $C_5-C_7$ fused ring to the benzene ring (Ring III);

$R^5$, $R^6$, $R^7$ and $R^8$ each independently represents H, $-CF_3$, $-COR^{10}$, alkyl or aryl, said alkyl or aryl optionally being substituted with $-OR^{10}$, $-SR^{10}$, $-S(O)_tR^{11}$, $-NR^{10}COOR^{11}$, $-N(R^{10})_2$, $-NO_2$, $-COR^{10}$, $-OCOR^{10}$, $-OCO_2R^{11}$, $-CO_2R^{10}$, $OPO_3R^{10}$, or $R^5$ is combined with $R^6$ to represent $=O$ or $=S$ and/or $R^7$ is combined with $R^8$ to represent $=O$ or $=S$;

$R^{10}$ represents H, alkyl, aryl, or aralkyl (e.g., benzyl);

$R^{11}$ represents alkyl or aryl;

the dotted line between carbon atoms 5 and 6 represents an optional double bond, such that when a double bond is present, A and B independently represent $-R^{10}$, halo, $-OR^{11}$, $-OCO_2R^{11}$ or $-OC(O)R^{10}$, and when no double bond is present between carbon atoms 5 and 6, A and B each independently represent $H_2$, $-(OR^{11})_2$; H and halo, dihalo, alkyl and H, (alkyl)$_2$, $-H$ and $-OC(O)R^{10}$, H and $-OR^{10}$, $=O$, aryl and H, $=NOR^{10}$ or $-O-(CH_2)_p-O-$ wherein p is 2, 3 or 4;

v is 0 to 5;

w is 0 or 1;

Y is

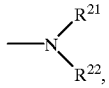

$-O-C_1-C_6$-alkyl or $-OM+$, wherein M+ is an alkali metal cation;

$R^{21}$ and $R^{22}$ are each independently H, $C_1-C_6$ alkyl, $-CH_2CONH_2$, phenyl, benzyl, $-SO_2-(C_1-C_6$-alkyl), $-NH$-phenyl, acyl, $C_3-C_6$ cycloalkyl, pyridyl, chlorophenyl,

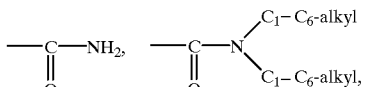

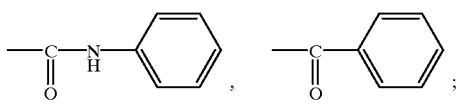

or $R^{21}$ and $R^{22}$ taken together with the nitrogen to which they are attached form

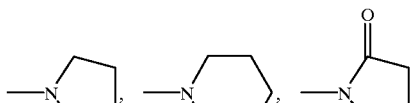

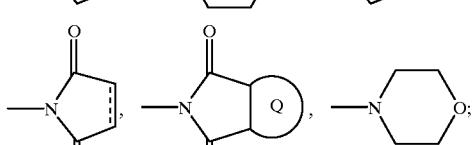

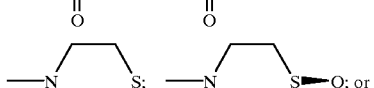

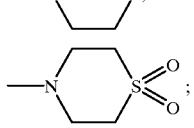

a dashed line means an optional chemical bond;

wherein Q is benzene, or a heterocyclic ring such as pyridine, pyrazine, or thiophene;

or a pharmaceutically acceptable salt thereof.

Preferred among compounds of the invention are compounds of the formula (1.0)

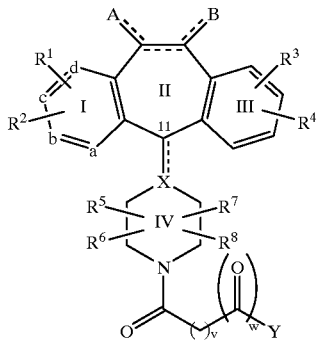
(1.0)

wherein $R^1$, $R^2$, X, A, B, a, b, c, d, are as described above, v is 0 to 4; w is 0; and Y is

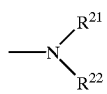

wherein $R^{21}$ and $R^{22}$ are as described above.

Also preferred are compounds of formula (1.0) wherein a is N; $R^5$, $R^6$, $R^7$ and $R^8$ are all H; and $R^1$, $R^2$, and $R^3$ are each independently selected from the group consisting of H or halo.

Also preferred are compounds of formula (1.0) wherein $R^1$ is H; and $R^2$ is Br; and $R^3$ and $R^4$ are each independently selected from the group consisting of Br and Cl.

Also preferred are compounds of formula (1.0) wherein X is CH.

Also preferred are compounds of any one of formula (1.0) wherein $R^3$ is Cl; and $R^4$ is Br.

Also preferred are compounds of formula (1.0) wherein a is N or $NO^-$, and $R^5$, $R^6$, $R^7$ and $R^8$ are all H; and $R^1$, $R^2$, $R^3$ and $R^4$ are each independently selected from the group consisting of H or halo.

Also preferred are compounds of formula (1.0) wherein A and B are each $H_2$; b and d are preferably CH.

Another group of preferred compounds is that wherein w is 1; v is 0–5; $R^1$ is H; $R^2$ is Br; $R^3$ and $R^4$ are independently Cl and Br; $R^5$–$R^8$ are each H; X is CH; and Y is $-O-C_1-C_6$ alkyl, $NH_2$ or $-OM+$.

Exemplary of compounds of the invention are:

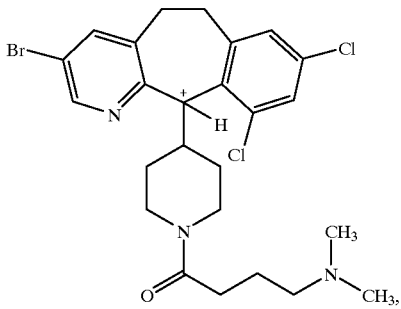

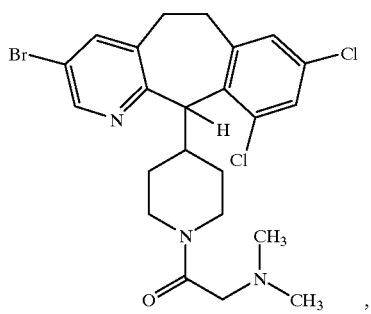

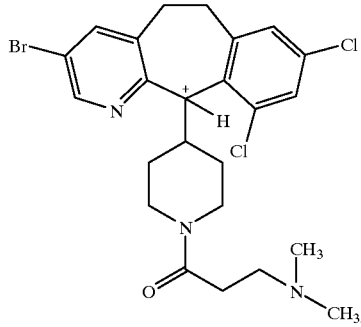

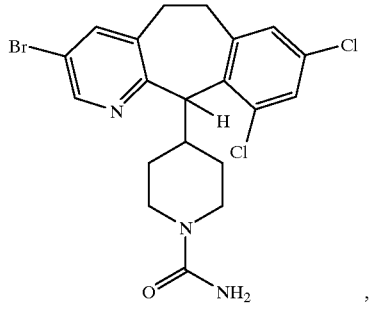

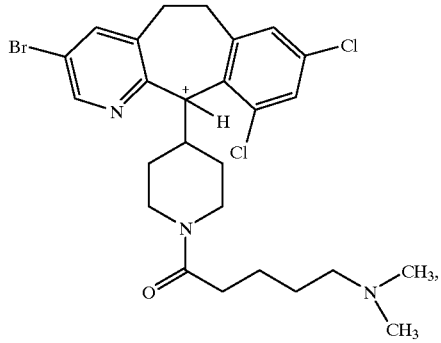

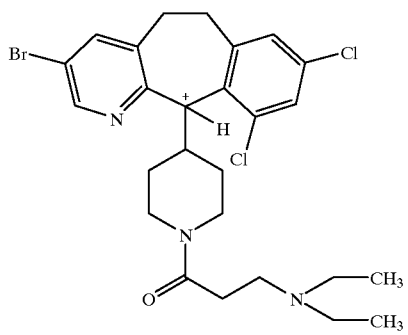

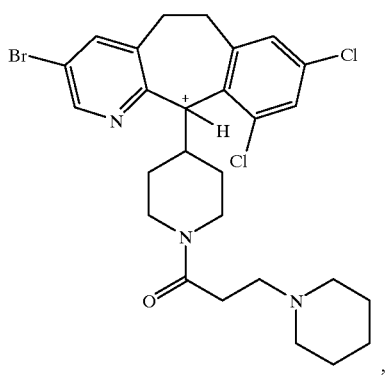
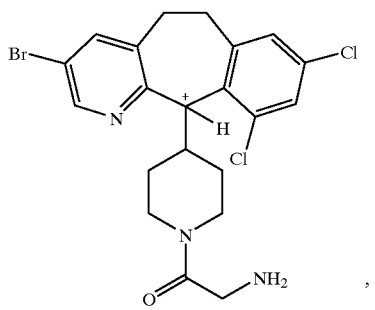
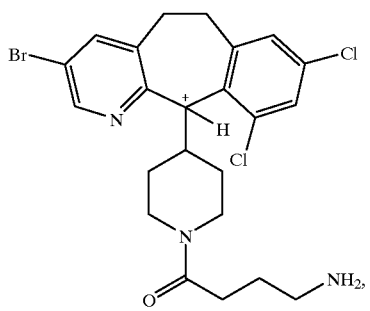
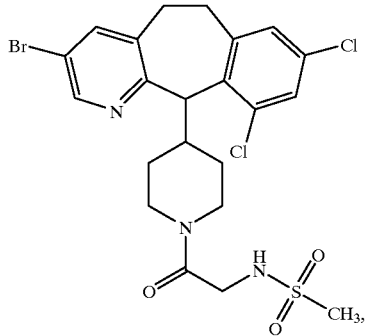
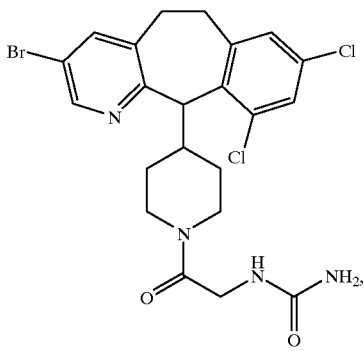
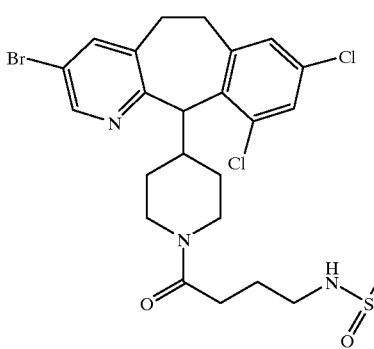
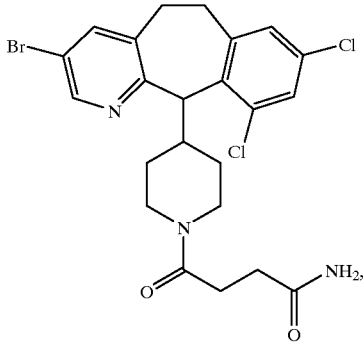
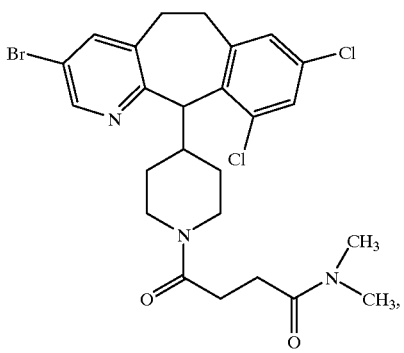

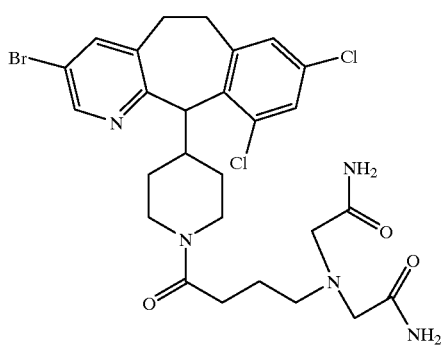
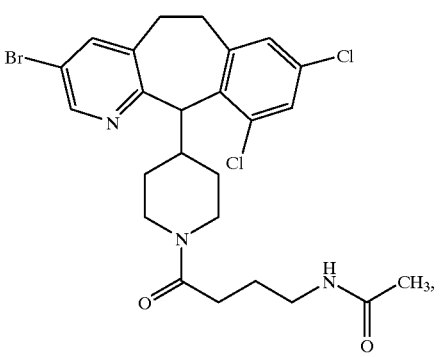
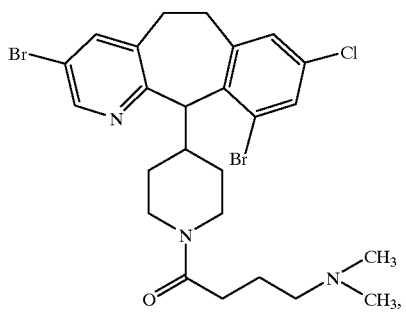
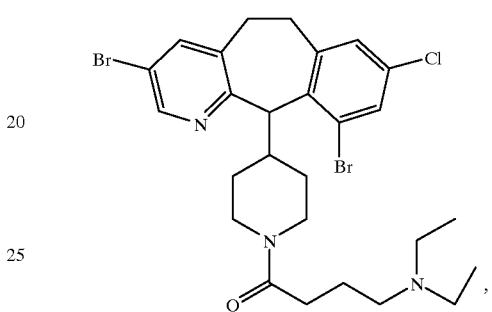
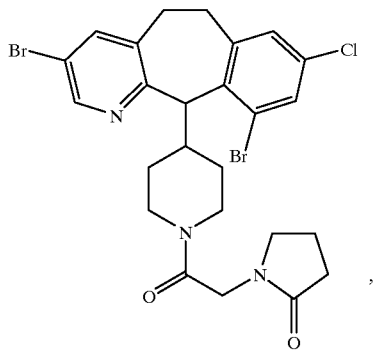
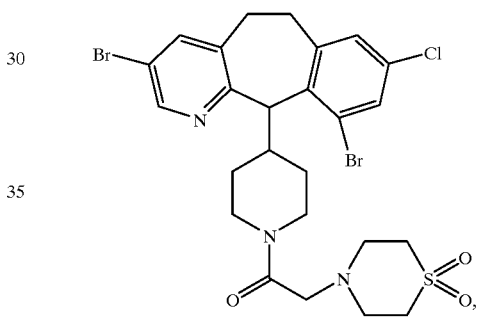
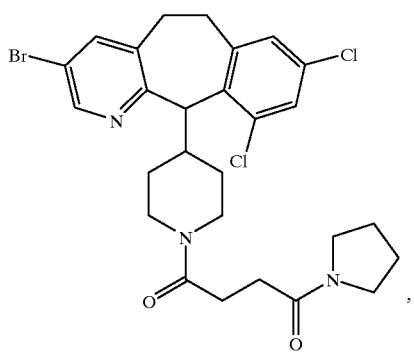
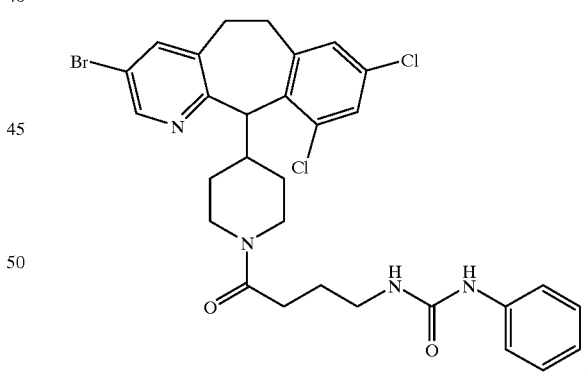

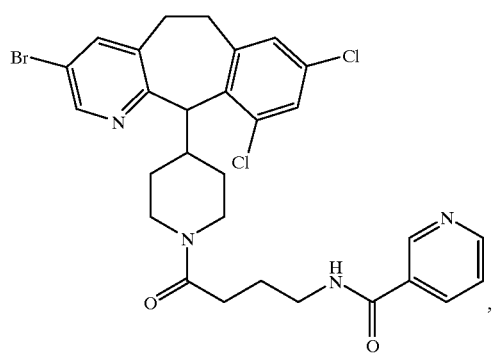
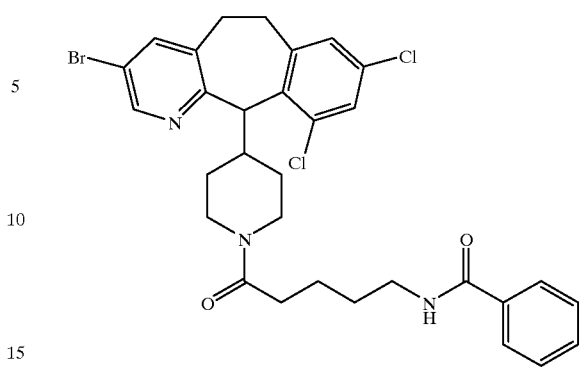
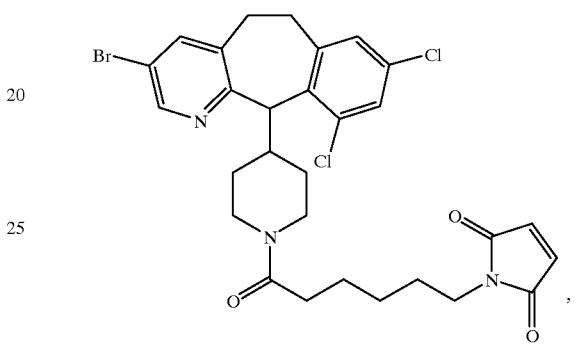
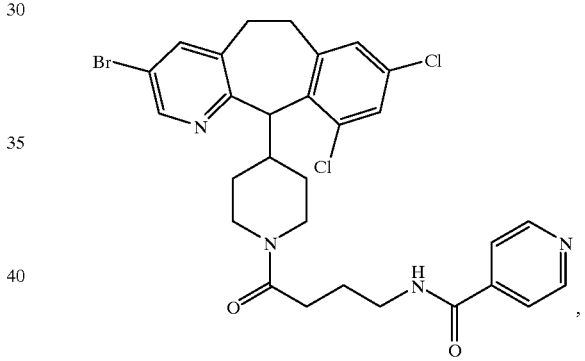
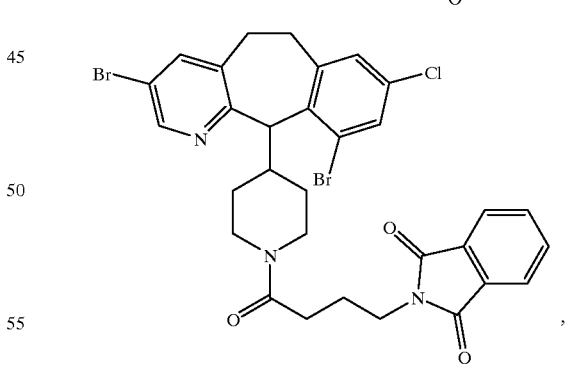

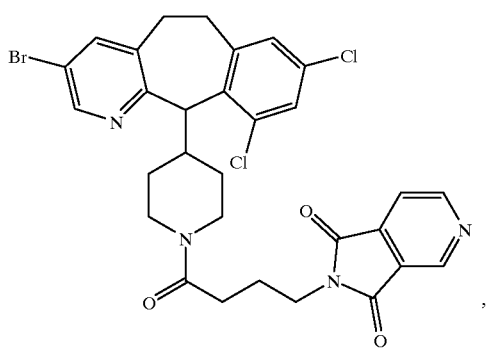
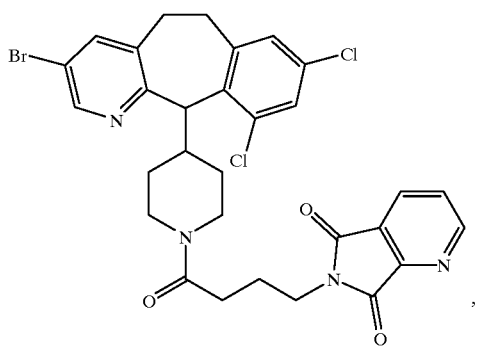
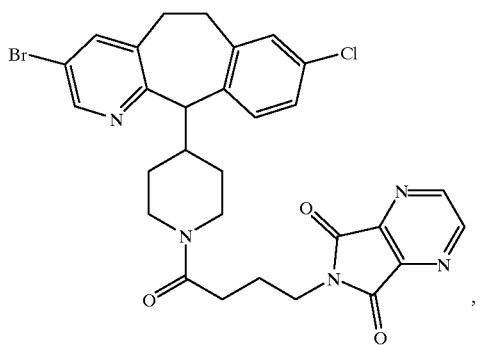
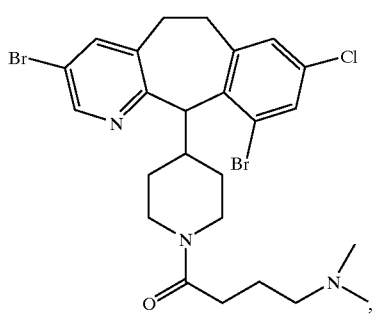
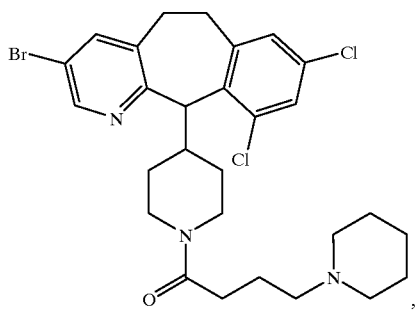
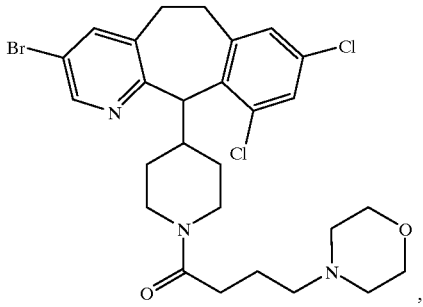
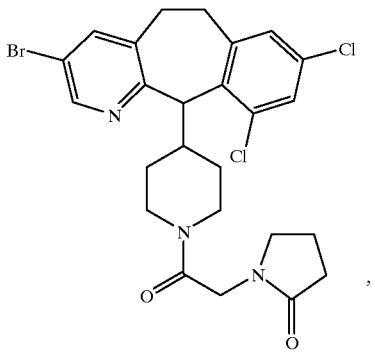
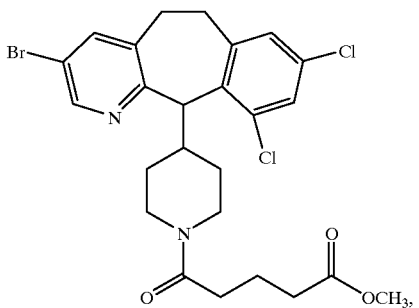
v
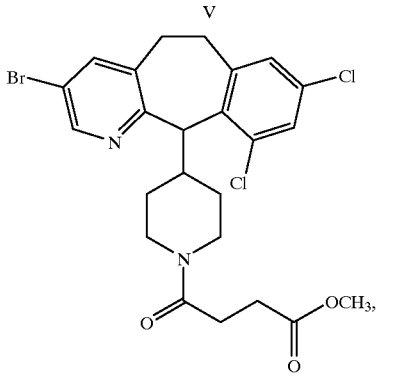
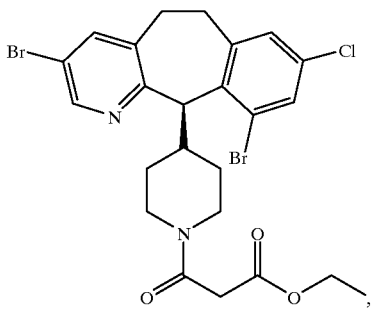

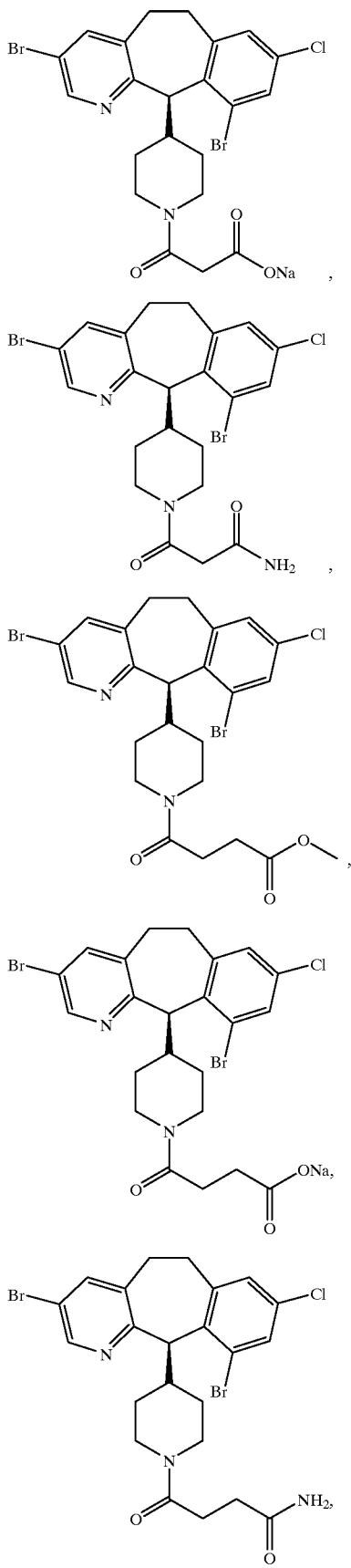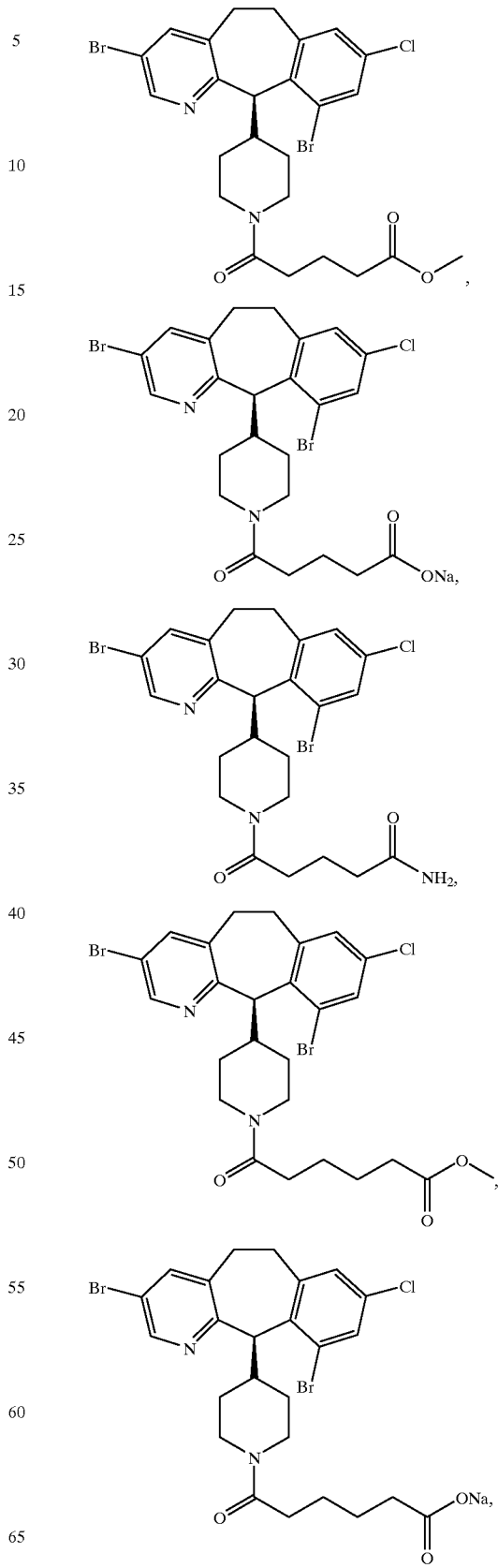

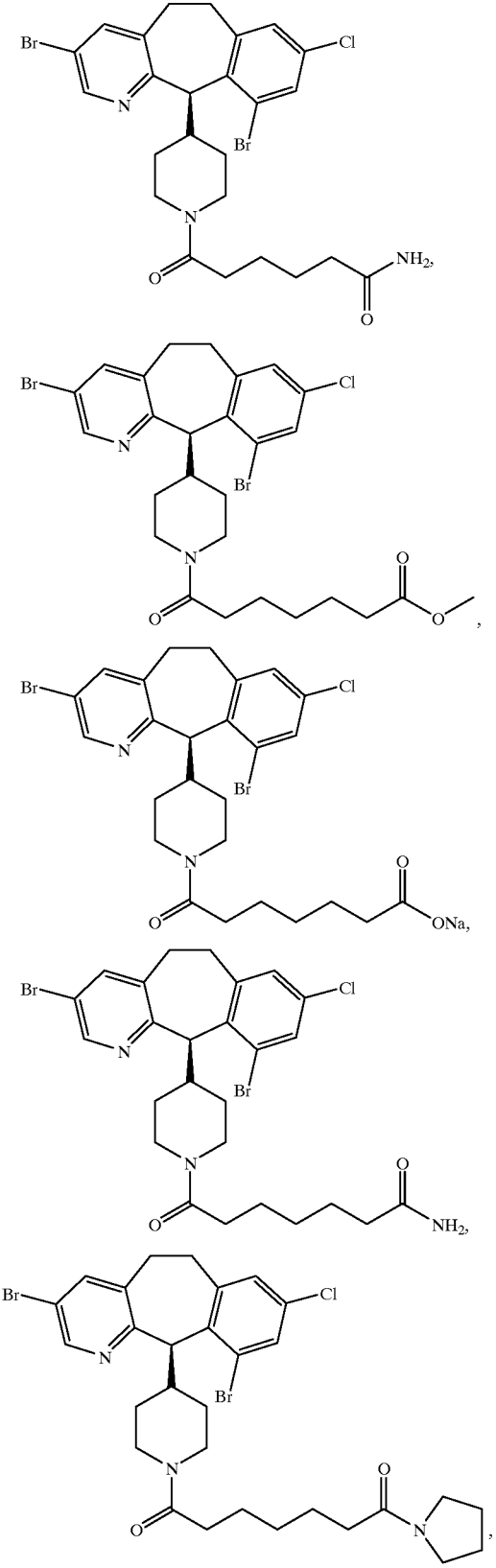
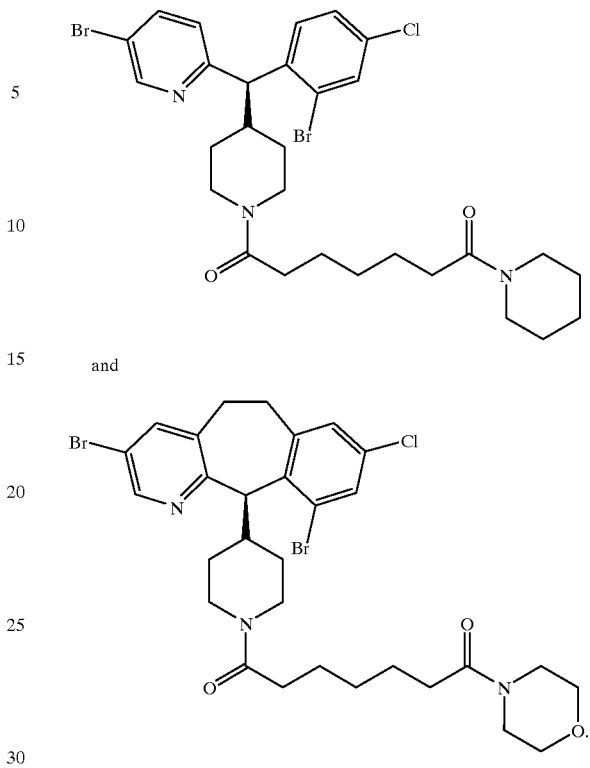

The compounds of formula (1.0) are useful as farnesyl protein transferase inhibitors. Accordingly, the compounds of formula (1.0) are useful for inhibiting tumor growth. Examples of tumors which may be inhibited include, but are not limited to, breast cancer, prostatic cancer, lung cancer (e.g., lung adenocarcinoma), pancreatic cancers (e.g., pancreatic carcinoma such as, for example, exocrine pancreatic carcinoma), colon cancers (e.g., colorectal carcinomas, such as, for example, colon adenocarcinoma and colon adenoma), myeloid leukemias (for example, acute myelogenous leukemia (AML)), thyroid follicular cancer, myelodysplastic syndrome (MDS), bladder carcinoma and epidermal carcinoma.

The invention also relates to pharmaceutical compositions for treating tumors which comprise a compound of formula (1.0) and a pharmaceutically acceptable carrier material.

The invention also relates to a method for treating tumors which comprises administering an anti-tumor effective amount of a compound of formula (1.0).

DETAILED DESCRIPTION OF THE INVENTION

The compounds of formula (1.0) can exist in unsolvated as well as solvated forms, including hydrated forms, e.g. the hemihydrate. In general, the solvated forms, with pharmaceutically acceptable solvents such as water, ethanol, and the like are equivalent to the unsolvated forms for the purposes of the invention.

Certain compounds of the invention can exist in stereoisomeric form. All such isomeric forms and mixtures thereof are within the scope of the present invention. Unless otherwise indicated, the methods of preparation disclosed herein may result in product distributions which include all possible structural isomers, although it is understood that physiological response may vary according to stereochemical structure. The isomers may be separated by conventional means such as fractional crystallization or HPLC (high performance liquid chromatography).

The compounds of formula (1.0) form pharmaceutically acceptable salts. The preferred pharmaceutically acceptable salts are nontoxic acid addition salts formed by adding to a suitable compound of the invention about a stoichiometric amount of a mineral acid, such as HCl, HBr, $H_2SO_4$ or $H_3PO_4$ or of an organic acid such as acetic, propionic, valeric, oleic, palmitic, stearic, lauric, benzoic, lactic, paratoluenesulfonic, methane sulfonic, citric, maleic, fumaric, succinic and the like, respectively.

When utilized herein and in the appended claims, the following terms, unless otherwise specified have the following meanings:

alkyl (including the alkyl portions of alkoxy, alkylamino and dialkylamino) represents straight and branched carbon chains and contains from one to twenty carbon atoms, preferably one to six carbon atoms;

acyl represents a moiety of the formula

wherein R is $C_1$–$C_6$ alkyl, phenyl, pyridyl, chlorophenyl, as described above;

alkanediyl represents a divalent, straight or branched hydrocarbon chain having from 1 to 20 carbon atoms, preferably 1 to 6 carbon atoms, the two available bonds being from the same or different carbon atoms thereof, e.g., methylene, ethylene, ethylidene, —$CH_2CH_2CH_2$—, —$CH_2CHCH_3$, —$CHCH_2CH_3$, etc.

cycloalkyl represents saturated carbocyclic rings branched or unbranched of from 3 to 20 carbon atoms, preferably 3 to 7 carbon atoms;

chlorophenyl represents a phenyl moiety where one of the hydrogens is replaced by a chlorine;

alkenyl represents straight and branched carbon chains having at least one carbon to carbon double bond and containing from 2 to 12 carbon atoms, preferably from 2 to 6 carbon atoms and most preferably from 3 to 6 carbon atoms;

alkynyl represents straight and branched carbon chains having at least one carbon to carbon triple bond and containing from 2 to 12 carbon atoms, preferably from 2 to 6 carbon atoms;

aryl (including the aryl portion of aryloxy and aralkyl) represents a carbocyclic group containing from 6 to 15 carbon atoms and having at least one aromatic ring (e.g., aryl is a phenyl ring), with all available substitutable carbon atoms of the carbocyclic group being intended as possible points of attachment, said carbocyclic group being optionally substituted (e.g., 1 to 3) with one or more of halo, alkyl, hydroxy, alkoxy, phenoxy, $CF_3$, amino, alkylamino, dialkylamino, —$COOR^{10}$ or —$NO_2$;

M+ is an alkali metal cation, preferably a sodium or lithium cation;

and halo represents fluoro, chloro, bromo and iodo.

Reference to the position of the substituents $R^1$, $R^2$, $R^3$, and $R^4$ is based on the numbered ring structure:

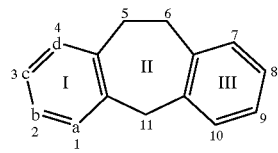

For example, $R^1$ can be at the C-4 position and $R^2$ can be at the C-2 or C-3 position. Also, for example, $R^3$ can be at the C-8 position and $R^4$ can be at the C-10 position.

When the bond from the IV ring to the C-11 carbon is a single bond, all stereoisomers are included within formula (1.0), that is, racemates, R-isomers, and S-isomers.

The compounds of the invention can be prepared according to the following methods.

The compounds of the invention are prepared as shown by reaction schemes 1, 2, and 3. Other conventional techniques such as ester hydrolysis and cleavage of protecting groups may be employed in the procedures to prepare the compounds of the invention.

Specifically, Scheme 1 depicts the synthesis of amides by the treatment of amine 1 with the appropriate carboxylic acid in the presence of a coupling agent such as DEC. Scheme 1A depicts the preparation of compounds of formula I wherein w is 1: esters, wherein Y is —O-alkyl, are prepared by reaction of an amine of formula 1 with a diacid monoester of formula 10 using standard coupling reagents, e.g., DEC and HOBT; the resultant ester can be hydroplyzed to an acid and converted to an alkali metal salt by conventional means, e.g., the sodium salt can be prepared by dissolving the ester in alcohol and treating with NaOH. The salt can then be reacted with an amine, again using standard coupling procedures, e.g., DEC and HOBT, to obtain amides of formula I (i.e., compounds wherein Y is —$NR^{21}R^{22}$).

SCHEME 1

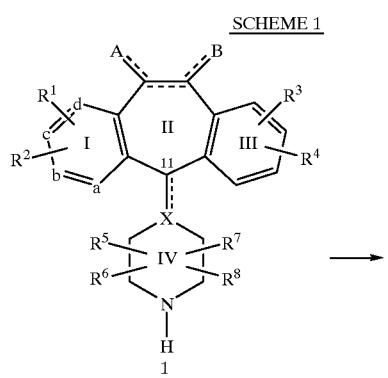

-continued

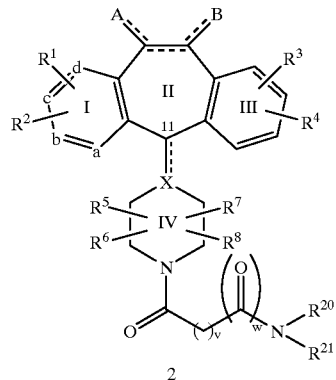

Scheme 2 depicts preparation of ureas of formula 5, acetamides of formula 7 and diamides of formula 8. In Scheme 2, the N—BOC protecting group is removed using TFA/CH$_2$Cl$_2$ or dioxane-HCl. The resulting amine 4 is treated with trimethylsilyl isocyanate in TFA to give ureas 5. Treatment of compounds of formula 4 with either acetyl chloride or acetic anhydride provides the acetamides of formula 7. Treatment of 5 with carboxylic anhydride in dimethylformamide at a temperature between about 40° C. to 50° C. and then treating the resulting adduct with Ac$_2$O and heating between about 85° C.–95° C. gives diamides of the formula 8.

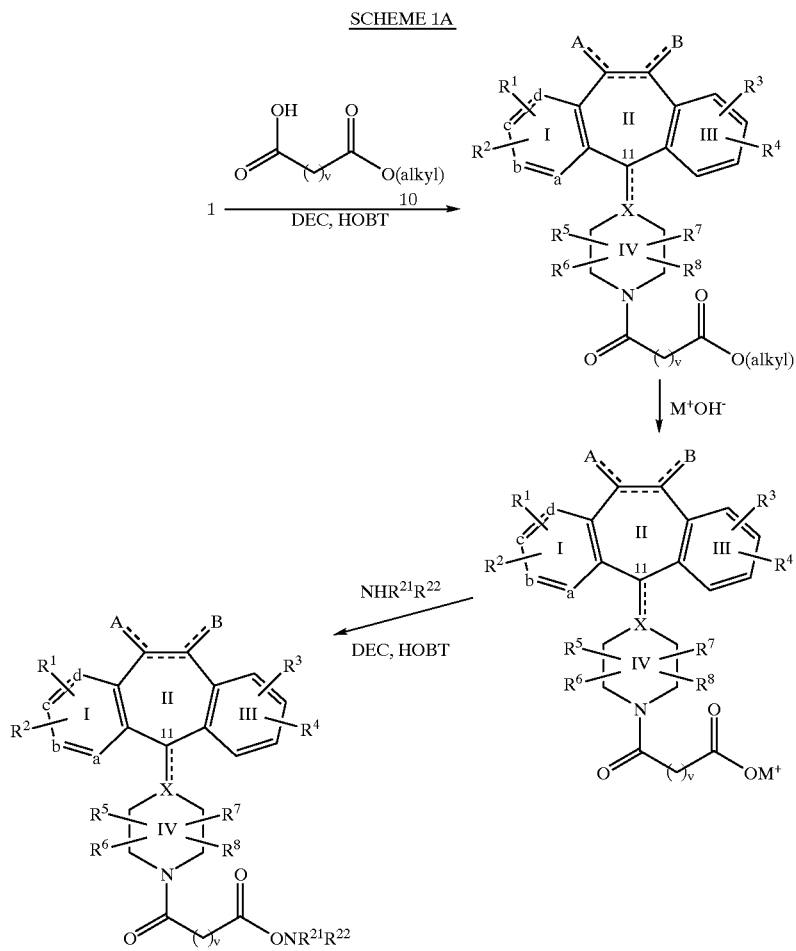

SCHEME 2
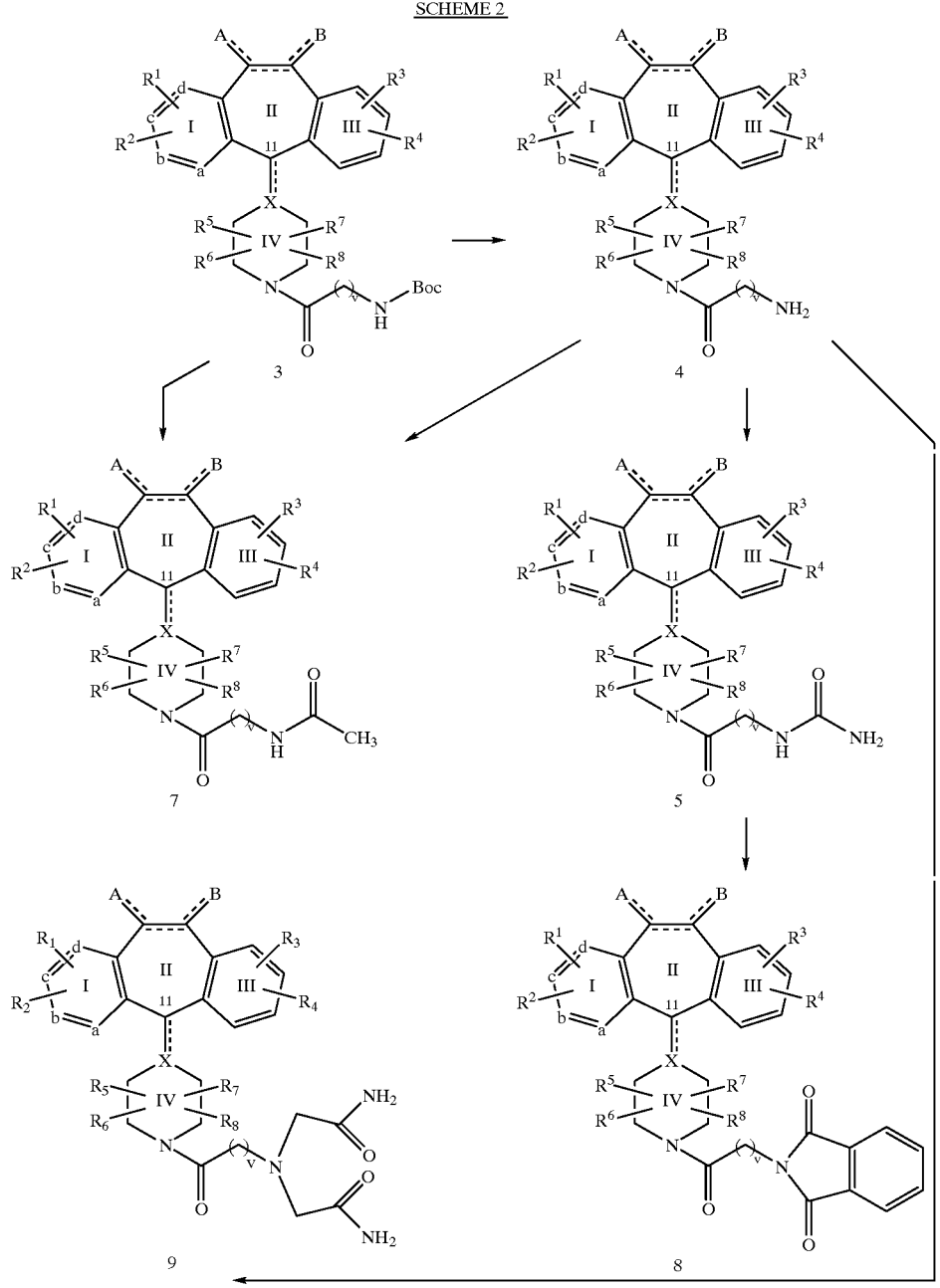
Scheme 3 shows the reaction of amine 1 with 4-chlorobutyl chloride to give an amide of the formula 8. Treatment of an amide of formula 8 with an amine affords the 4-amino substituted analogs of formula 9.

Scheme 3

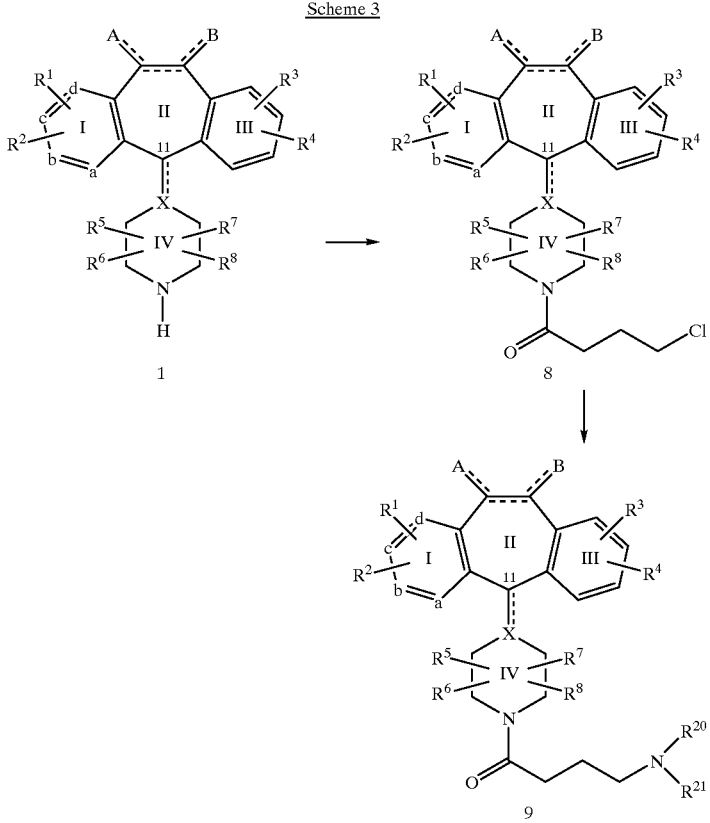

Starting materials used in the preparation of compounds of the invention are either known, can be prepared according to known methods, or can be prepared by methods that are analogous to known methods.

Compounds of formula I comprising a pyridyl N-oxide in ring I of the tricyclic portion can be prepared by procedures well known in the art. For example, the amine compound of formula 1 can be reacted with MCPBA in a suitable organic solvent, e.g., $CH_2Cl_2$ (usually anhydrous). at a suitable temperature, to obtain an N-oxide of formula 1a

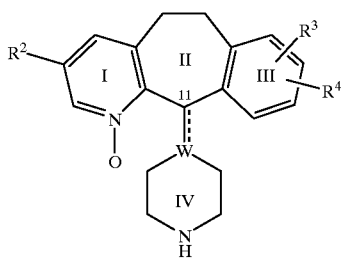

1a

Generally, the organic solvent solution of formula 1 is cooled to about 0° C. before the MCPBA is added. The reaction is then allowed to warm to room temperature during the reaction period. The desired product can be recovered by standard separation means, for example, the reaction mixture can be washed with an aqueous solution of a suitable base, e.g., saturated $NaHCO_3$ or NaOH (e.g., i N NaOH), and then dried over anhydrous $MgSO_4$. The solution containing the product can be concentrated in vacuo, and the product can be purified by standard means, e.g., by chromatography using silica gel (e.g., flash column chromatography).

Compounds of formula 1 are prepared by methods known in the art, for example by methods disclosed in WO 95/10516, in U.S. Pat. No. 5,151,423 and those described below. Compounds of formula 1 wherein the C-3 postion of the pyridine ring in the tricyclic structure is substituted by bromo can also be prepared by a procedure comprising the following steps:

(a) reacting an amide of the formula

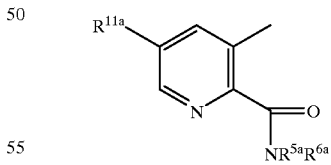

wherein $R^{11a}$ is Br, $R^{5a}$ is hydrogen and $R^{6a}$ is $C_1$–$C_6$ alkyl, aryl or heteroaryl; $R^{5a}$ is $C_1$–$C_6$ alkyl, aryl or heteroaryl and $R^{6a}$ is hydrogen; $R^{5a}$ and $R^{6a}$ are independently selected from the group consisting of $C_1$–$C_6$ alkyl and aryl; or $R^{5a}$ and $R^{6a}$, together with the nitrogen to which they are attached, form a ring comprising 4 to 6 carbon atoms or comprising 3 to 5 carbon atoms and one hetero moiety selected from the group consisting of —O— and —$NR^{9a}$—, wherein $R^{9a}$ is H, $C_1$–$C_6$ alkyl or phenyl;

with a compound of the formula

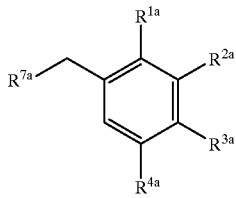

wherein $R^{1a}$, $R^{2a}$, $R^{3a}$ and $R^{4a}$ are are independently selected from the group consisting of hydrogen and halo and $R^{7a}$ is Cl or Br, in the presence of a strong base to obtain a compound of the formula

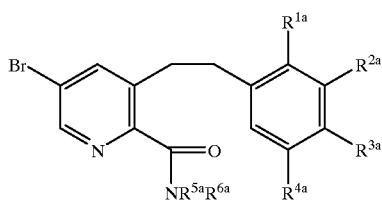

(b) reacting a compound of step (a) with (i) $POCl_3$ to obtain a cyano compound of the formula

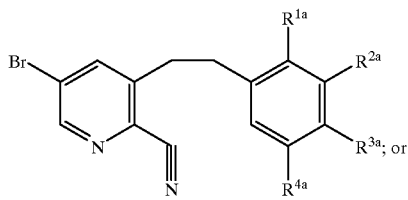

(ii) DIBALH to obtain an aldehyde of the formula

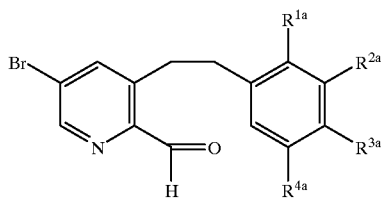

(c) reacting the cyano compound or the aldehyde with a piperidine derivative of the formula

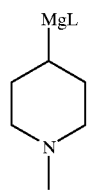

wherein L is a leaving group selected from the group consisting of Cl and Br, to obtain an aldehyde or an alcohol of the formula below, respectively:

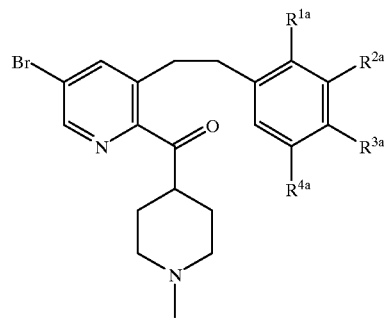

or

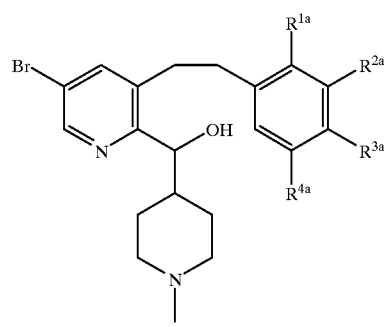

(d)(i) cyclizing the aldehyde with $CF_3SO_3H$ to obtain a compound of formula II wherein the dotted line represents a double bond; or (d)(ii) cyclizing the alcohol with polyphosphoric acid to obtain a compound of formula II wherein the dotted line represents a single bond.

Methods for preparing compounds of formula 1 disclosed in WO 95/10516, U.S. Pat. No. 5,151,423 and described below employ a tricyclic ketone intermediate. Such intermediates of the formula

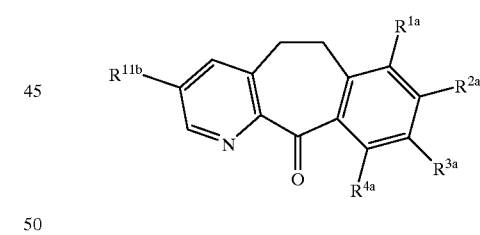

wherein $R^{11b}$, $R^{1a}$, $R^{2a}$, $R^{3a}$ and $R^{4a}$ are independently selected from the group consisting of hydrogen and halo, can be prepared by the following process comprising:

(a) reacting a compound of the formula

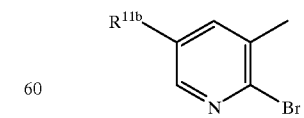

(i) with an amine of the formula $NHR^{5a}R^{6a}$, wherein $R^{5a}$ and $R^{6a}$ are as defined in the process above; in the presence of a palladium catalyst and carbon monoxide to obtain an amide of the formula:

(ii) with an alcohol of the formula $R^{10a}OH$, wherein $R^{10a}$ is $C_1-C_6$ lower alkyl or $C_3-C_6$ cycloalkyl, in the presence of a palladium catalyst and carbon monoxide to obtain the ester of the formula

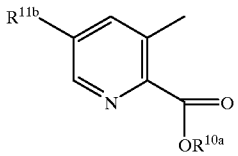

followed by reacting the ester with an amine of formula $NHR^{5a}R^{6a}$ to obtain the amide;

(b) reacting the amide with an iodo-substituted benzyl compound of the formula

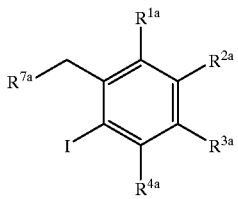

wherein $R^{1a}$, $R^{2a}$, $R^{3a}$, $R^{4a}$ and $R^{7a}$ are as defined above, in the presence of a strong base to obtain a compound of the formula

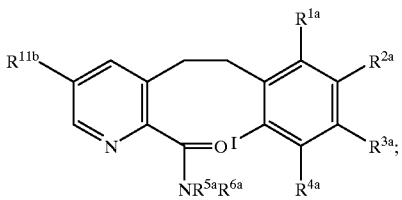

(c) cyclizing a compound of step (b) with a reagent of the formula $R^{8a}MgL$, wherein $R^{8a}$ is $C_1-C_8$ alkyl, aryl or heteroaryl and L is Br or Cl, provided that prior to cyclization, compounds wherein $R^{5a}$ or $R^{6a}$ is hydrogen are reacted with a suitable N-protecting group.

(+)-Isomers of compounds of formula 1 wherein X is CH can be prepared with high enantioselectivity by using a process comprising enzyme catalyzed transesterification. Preferably, a racemic compound of formula 1, wherein X is C, the double bond is present and a substituent other than H is present at the 10-position on ring III, is reacted with an enzyme such as Toyobo LIP-300 and an acylating agent such as trifluoroethly isobutyrate; the resultant (+)-amide is then hydrolyzed, for example by refluxing with an acid such as $H_2SO_4$, to obtain the corresponding optically enriched (+)-isomer. Alternatively, a racemic compound of formula 1, wherein X is C, the double bond is present and a substituent other than H is present at the 10-position on ring III, is first reduced to the corresponding racemic compound of formula 1 wherein X is CH and then treated with the enzyme (Toyobo LIP-300) and acylating agent as described above to obtain the (+)-amide, which is hydrolyzed to obtain the optically enriched (+)-isomer.

Nitration Process

A

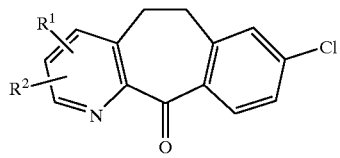

or

B

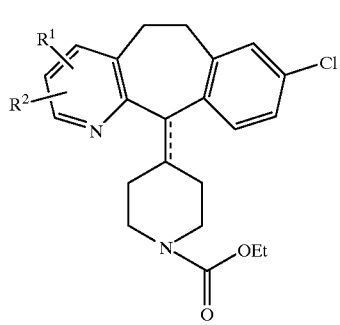

A process for producing compounds of the formulas 10 through 18 shown below. These compounds are useful as intermediates in the preparation of compounds of formula (1.0) of the invention. The process involves suspending one molar equivalent of either formula A or B above in an appropriate aqueous acid such as concentrated sulfuric acid and then cooling the reaction mixture to $-20°$ to $40°$ C. and then adding 1.1 molar equivalent of $KNO_3$ at the same temperature. The reaction mixture is stirred at that temperature for 1 hour and then allowed to warm up to room temperature over a period of 10 to 16 hours. The reaction mixture is then poured onto ice and basified with an appropriate base such as concentrated ammonium hydroxide or 50% aqueous NaOH. It is extracted with an appropriate solvent such as $CH_2Cl_2$ and desired compounds are obtained either by recrystallization or column chromatography.

Compounds Obtained by the Low Temperature Nitration Process

10

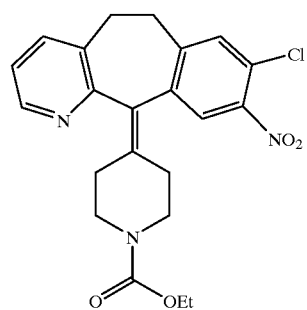

11 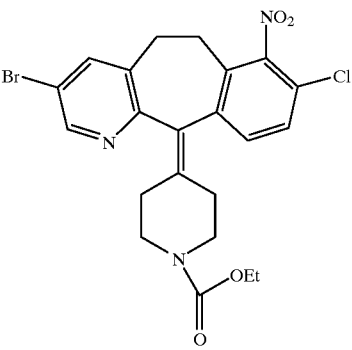

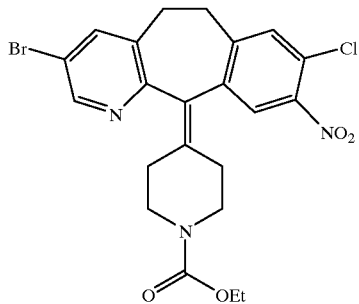

12 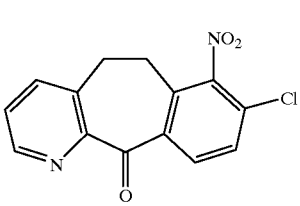

17 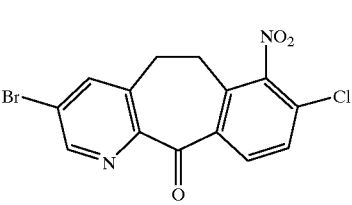

13 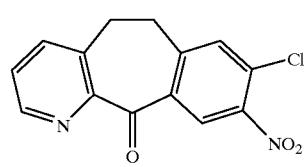

18 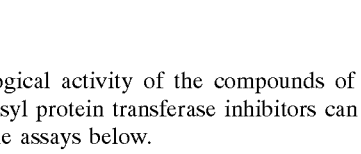

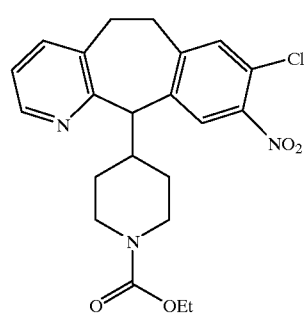

14 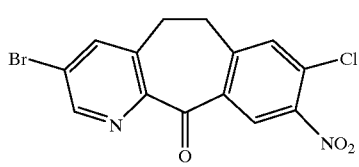

Biological activity of the compounds of the invention as farnesyl protein transferase inhibitors can be demonstrated by the assays below.

Assays

1. In vitro enzyme assays: Inhibition of farnesyl protein transferase and geranylgeranyl protein transferase.

Farnesyl protein transferase (FPT) was partially purified from rat brain by ammonium sulfate fractionation followed by Q-Sepharose (Pharmacia, Inc.) anion exchange chromatography essentially as described by Yokoyama et al (Yokoyama, K., et al., (1991), A protein geranylgeranyltransferase from bovine brain: Implications for protein prenylation specificity, *Proc. Natl. Acad. Sci USA* 88: 5302–5306, the disclosure of which is incorporated herein by reference thereto). Human farnesyl protein transferase was also expressed in *E. coli*, using cDNA clones encoding both the a and b subunits. The methods used were similar to those published (Omer, C. et al., (1993), Characterization of recombinant human farnesyl protein transferase: Cloning, expression, farnesyl diphosphate binding, and functional homology with yeast prenyl-protein transferases, Biochemistry 32:5167–5176). Human farnesyl protein transferase was partially-purified from the soluble protein fraction of *E.*

15 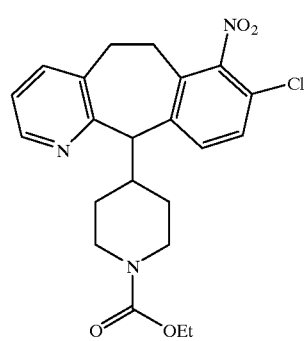

coli as described above. The tricyclic farnesyl protein transferase inhibitors disclosed herein inhibited both human and rat enzyme with similar potencies. Two forms of val$^{12}$-Ha-Ras protein were prepared as substrates for these enzymes, differing in their carboxy terminal sequence. One form terminated in cysteine-valine-leucine-serine (Ras-CVLS) the other in cystein-valine-leucine-leucine (Ras-CVLL). Ras-CVLS is a substrate for the farnesyl protein transferase while Ras-CVLL is a substrate for geranylgeranyl protein transferase I. The cDNAs encoding these proteins were constructed so that the proteins contain an amino-terminal extension of 6 histidine residues. Both proteins were expressed in Escherichia coli and purified using metal chelate affinity chromatography. The radiolabelled isoprenyl pyrophosphate substrates, [$^3$H]farnesyl pyrophosphate and [$^3$H]geranylgeranyl pyrophosphate, were purchased from DuPont/New England Nuclear.

Several methods for measuring farnesyl protein transferase activity have been described (Reiss et al 1990, Cell 62: 81; Schaber et al 1990, J. Biol. Chem. 265: 14701; Manne et al 1990, PNAS 87: 7541; and Barbacid & Manne 1993, U.S. Pat. No. 5,185,248). The activity was assayed by measuring the transfer of [$^3$H]farnesyl from [$^3$H]farnesyl pyrophosphate to Ras-CVLS using conditions similar to those described by Reiss et al. 1990 (Cell 62: 81) The reaction mixture contained 40 mM Hepes, pH 7.5; 20 mM magnesium chloride; 5 mM dithiothreitol; 0.25 $\mu$M [$^3$H] farnesyl pyrophosphate; 10 ml Q-Sepharose-purified farnesyl protein transferase; the indicated concentration of tricyclic compound or dimethylsulfoxide (DMSO) vehicle control (5% DMSO final); and 5 mM Ras-CVLS in a total volume of 100 ml. The reaction was allowed to proceed for 30 minutes at room temperature and then stopped with 0.5 ml of 4% sodium dodecyl sulfate (SDS) followed by 0.5 ml of cold 30% TCA. Samples were allowed to sit on ice for 45 minutes and precipitated Ras protein was then collected on GF/C filter paper mats using a Brandel cell harvester. Filter mats were washed once with 6% TCA, 2% SDS and radioactivity was measured in a Wallac 1204 Betaplate BS liquid scintillation counter. Percent inhibition was calculated relative to the DMSO vehicle control.

2. Cell-Based Assay: Transient expression of val$^{12}$-Ha-Ras-CVLS and val$^{12}$-Ha-Ras-CVLL in COS monkey kidney cells: Effect of farnesyl protein transferase inhibitors on Ras processing and on disordered cell growth induced by transforming Ras.

COS monkey kidney cells were transfected by electroporation with the plasmid pSV-SPORT (Gibco/BRL) containing a cDNA insert encoding either Ras-CVLS or Ras-CVLL, leading to transient overexpression of a Ras substrate for either farnesyl protein transferase or geranylgeranyl protein transferase I, respectively (see above).

Following electroporation, cells were plated into 6-well tissue culture dishes containing 1.5 ml of Dulbecco's-modified Eagle's media (GIBCO, Inc.) supplemented with 10% fetal calf serum and the appropriate farnesyl protein transferase inhibitors. After 24 hours, media was removed and fresh media containing the appropriate drugs was re-added.

48 hours after electroporation cells were examined under the microscope to monitor disordered cell growth induced by transforming Ras. Cells expressing transforming Ras become more rounded and refractile and overgrow the monolayer, reminiscent of the transformed phenotype. Cells were then photographed, washed twice with 1 ml of cold phosphate-buffered saline (PBS) and removed from the dish by scraping with a rubber policeman into 1 ml of a buffer containing 25 mM Tris, pH 8.0; 1 mM ethylenediamine tetraacetic acid; 1 mM phenylmethylsulfonyl fluoride; 50 mM leupeptin; and 0.1 mM pepstatin. Cells were lysed by homogenization and cell debris was removed by centrifugation at 2000×g for 10 min.

Cellular protein was precipitated by addition of ice-cold trichloroacetic acid and redissolved in 100 ml of SDS-electrophoresis sample buffer. Samples (5–10 ml) were loaded onto 14% polyacrylamide minigels (Novex, Inc.) and electrophoresed until the tracking dye neared the bottom of the gel. Proteins resolved on the gels were electroblotted onto nitrocellulose membranes for immunodetection.

Membranes were blocked by incubation overnight at 4° C. in PBS containing 2.5% dried milk and 0.5% Tween-20 and then incubated with a Ras-specific monoclonal antibody, Y13–259 (Furth, M. E., et al., (1982), Monoclonal antibodies to the p21 products of the transforming gene of Harvey murine sarcoma virus and of the cellular ras gene family, J. Virol. 43: 294–304), in PBS containing 1% fetal calf serum for one hour at room temperature. After washing, membranes were incubated for one hour at room temperature with a 1:5000 dilution of secondary antibody, rabbit anti-rat IgG conjugated to horseradish peroxidase, in PBS containing 1% fetal calf serum. The presence of processed and unprocessed Ras-CVLS or Ras-CVLL was detected using a colorimetric peroxidase reagent (4-chloro-1-naphthol) as described by the manufacturer (Bio-Rad).

Compounds of the invention exhibited the following biological activity.

TABLE 2

| FPT INHIBITION | | | |
|---|---|---|---|
| EXAMPLE | FPT IC$_{50}$ ($\mu$M) | EXAMPLE | FPT IC$_{50}$ ($\mu$M) |
| 1 | 0.39 | 25 | 47% @ 330 nM |
| 2 | 0.004 | 26 | 0.54 |
| 3 | 1.1 | 27 | 0.13 |
| 4 | 0.38 | 28 | 43% @ 110 nM |
| 5 | 0.056 | 29 | 0.032 |
| 6 | 0.0065 | 30 | 36% @ 110 nM |
| 7 | 0.022 | 31 | 0.058 |
| 8 | 0.014 | 32 | 12% @ 88 nM |
| 9 | 0.006 | 33 | 38.7% @ 93.4 nM |
| 10 | 0.019 | 45 | 0.028 |
| 11 | 0.076 | 46 | 0.078 |
| 12 | 0.061 | 47 | 0.068 |
| 13 | 0.015 | 48 | 0.009 |
| 14 | 0.016 | 49 | 0.27 |
| 15 | 0.063 | 50 | 0.014 |
| 16 | >0.1 | 51 | 0.019 |
| 23 | 0.62 | 52 | 0.044 |
| 17 | ~0.1 | 53 | 0.010 |
| 18 | 9% @ 93 nM | 54 | 0.015 |
| 19 | 21% @ 0.06 $\mu$g/$\mu$L | 55 | 0.017 |
| 20 | 0% @ 92 nM | 56 | 0.007 |
| 21 | 35% @ 0.06 $\mu$g/$\mu$L | 57 | 0.011 |
| 22 | 41% @ 0.06 $\mu$g/$\mu$L | 58 | 0.0091 |
| 24 | 20% @ 0.06 $\mu$g/$\mu$L | 59 | 0.0033 |

TABLE 3

ACTIVITY IN COS CELLS

| EXAMPLE | INHIBITION OF RAS PROCESSING IC$_{50(\mu M)}$ |
|---------|-----------------------------------------------|
| 2       | 0.013                                         |
| 6       | 0.035                                         |
| 10      | 0.500                                         |
| 13      | 0.200                                         |
| 14      | 0.250                                         |
| 18      | 0.540                                         |
| 58      | 0.300                                         |
| 59      | 0.015                                         |

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 70 percent active ingredient. Suitable solid carriers are known in the art, e.g. magnesium carbonate, magnesium stearate, talc, sugar, lactose. Tablets, powders, cachets and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Liquid form preparations include solutions, suspensions and emulsions. As an example may be mentioned water or water-propylene glycol solutions for parenteral injection.

Liquid form preparations may also include solutions for intranasal administration.

Aerosol preparations suitable for inhalation may include solutions and solids in powder form, which may be in combination with a pharmaceutically acceptable carrier, such as an inert compressed gas.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in unit dosage form. In such form, the preparation is subdivided into unit doses containing appropriate quantities of the active component, e.g., an effective amount to achieve the desired purpose.

The quantity of active compound in a unit dose of preparation may be varied or adjusted from about 0.1 mg to 1000 mg, more preferably from about 1 mg. to 300 mg, according to the particular application.

The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The amount and frequency of administration of the compounds of the invention and the pharmaceutically acceptable salts thereof will be regulated according to the judgment of the attending clinician considering such factors as age, condition and size of the patient as well as severity of the symptoms being treated. A typical recommended dosage regimen is oral administration of from 10 mg to 2000 mg/day preferably 10 to 1000 mg/day, in two to four divided doses to block tumor growth. The compounds are non-toxic when administered within this dosage range.

While the present invention has been described in conjunction with the specific embodiments set forth herein, many alternatives, modifications and variations thereof will be apparent to those of ordinary skill in the art. All such alternatives, modifications and variations are intended to fall within the spirit and scope of the present invention.

Compounds of the invention may be prepared according to the procedures described in WO 95/10516 published Apr. 20, 1995, copending application Ser. No. 08/410,187 filed Mar. 24, 1995, copending application Ser. No. 08/577,951 filed Dec. 22, 1995, and copending application Ser. No. 08/615,760 filed Mar. 13, 1996; the disclosures of each being incorporated herein by reference thereto; and according to the procedures described below.

PREPARATIVE EXAMPLE 1

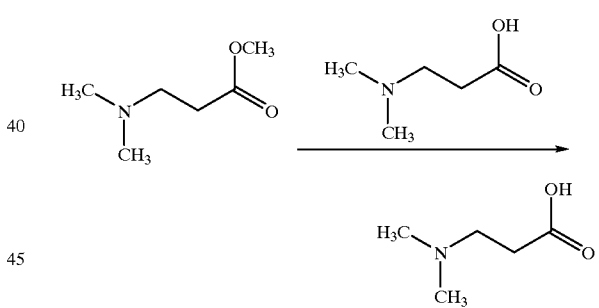

2 g (15 mmol) of methyl 3-(dimethyl amino) propionate was dissolved in 20 mL of EtOH and then 20 mL of 1M LiOH was added. The reaction mixture was stirred at room temperature for 16 hours. The solvents were stripped off. The resulting material in water was dissolved and pH was adjusted to ~6. The reaction mixture was concentrated to give the product. Mass Spec.: MH$^+$=118.

PREPARATIVE EXAMPLE 2

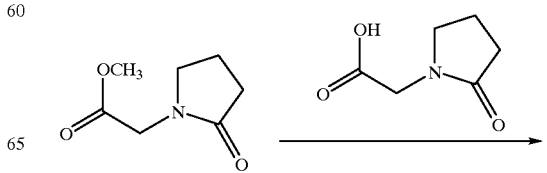

-continued

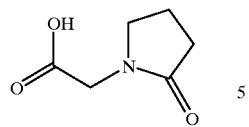

2 g (12.7 mmol) of methyl 2-oxo-1-pyrrolidine acetate was dissolved in 20 mL of EtOH and then 20 mL of 1M LiOH was added. The reaction mixture was stirred at room temperature for 16 hours. The solvents were stripped off. The resulting material was dissolved in water and the pH was adjusted to ~4. The reaction mixture was concentrated to give the product. Mass Spec.: MH$^+$=144.

PREPARATIVE EXAMPLE 3

(+)-4-(3-BROMO-8,10-DICHLORO-6,11-DIHYDRO-5H-BENZO[5,6]-CYCLO-HEPTA[1,2-b]PYRIDIN-11-YL)-1-[4-(CHLORO)-1-OXOBUTYL]PIPIRIDINE

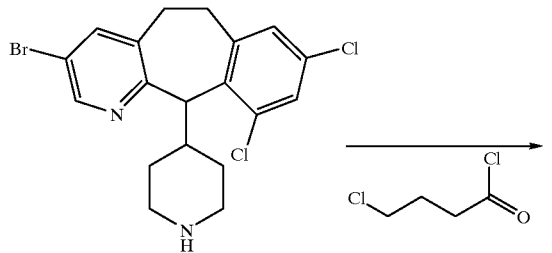

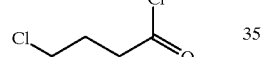

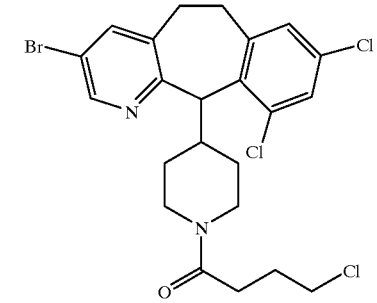

4-bromobutyric acid (5 g, 29.9 mmol) was dissolved in 50 mL of CH$_2$Cl$_2$ and thionyl chloride (35.6 g, 299 mmol) was then added. The reaction mixture was stirred at room temperature for ~16 h. Excess thionyl chloride was removed by rotary evaporation and final traces were chased off with toluene. The crude product was dried under high vacuum to obtain 4.47 g of crude acid chloride. To this acid chloride (0.65 g, 3.5 mmol) was added the title compound of preparative Example 7, (1.0 g, 2.3 mmol), and triethylamine (0.7 mL, 5.2 mmol) and then dissolved in 10 mL of CH$_2$Cl$_2$. Reaction mixture was stirred at room temperature for 16 h. It was extracted with sat. NaHCO$_3$ and the CH$_2$Cl$_2$ fraction was dried over MgSO$_4$ and concentrated to give 0.63 g of the title compound FAB-MS: MH$^+$=531

PREPARATIVE EXAMPLE 4

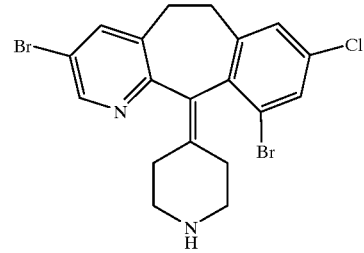

Step A:

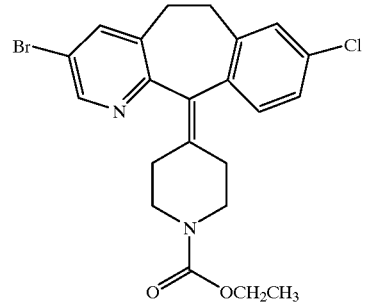

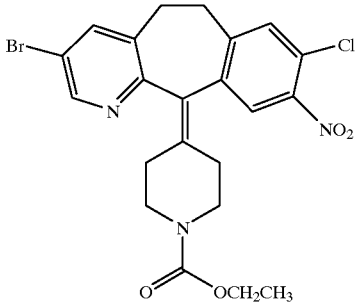

15 g (38.5 mmol) of 4-(8-chloro-3-bromo-5,6-dihydro-11H-benzo[5,6]cyclohepta[1,2-b]pyridin-11-ylidene)-1-piperidine-1-carboxylic acid ethyl ester and 150 mL of concentrated H$_2$SO$_4$ at −5° C., then add 3.89 g (38.5 mmol) of KNO$_3$ were combined and stirred for 4 hours. The mixture was poured into 3 L of ice and basified with 50% NaOH (aqueous). The mixture was extracted with CH$_2$Cl$_2$, dried over MgSO$_4$, then filtered and concentrated in vacuo to a residue. The residue was recrystallized from acetone to give 6.69 g of the product. $^1$H NMR (CDCl$_3$, 200 MHz): 8.5 (s, 1H); 7.75 (s, 1H); 7.6 (s, 1H); 7.35 (s, 1H); 4.15 (q, 2H); 3.8 (m, 2H); 3.5–3.1 (m, 4H); 3.0–2.8 (m, 2H); 2.6–2.2 (m, 4H); 1.25 (t, 3H).

Step B:

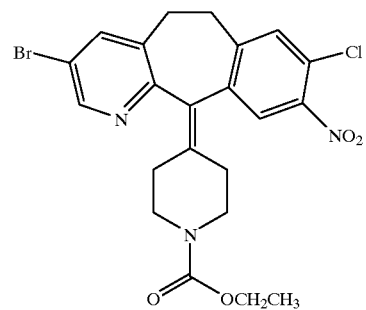

-continued

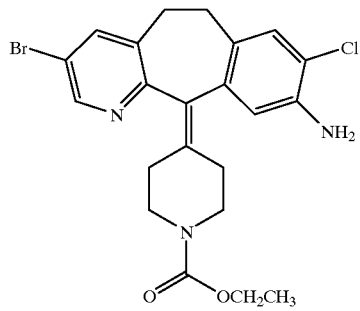

6.69 g (13.1 mmol) of the product of Step A and 100 mL of 85% EtOH/water were combined, then 0.66 g (5.9 mmol) of $CaCl_2$ and 6.56 g (117.9 mmol) of Fe were added and the mixture was heated at reflux overnight. The hot reaction mixture was filtered through celite® and the filter cake was rinsed with hot EtOH. The filtrate was concentrated in vacuo to give 7.72 g of the product. Mass Spec.: $MH^+$=478.0

Step C:

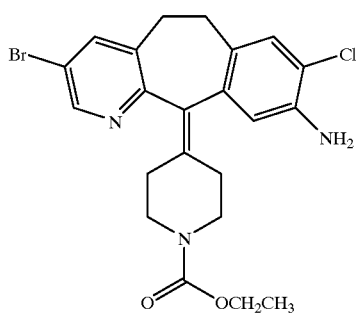

7.70 g of the product of Step B and 35 mL of HOAc, were combined then 45 mL of a solution of $Br_2$ in HOAc was added and the the mixture was stirred at room temperature overnight. 300 mL of 1 N NaOH (aqueous) was added, then 75 mL of 50% NaOH (aqueous) was added and the mixure was extracted with EtOAc. The extract was dried over $MgSO_4$ and concentrated in vacuo to a residue. The residue was chromatographed (silica gel, 20%–30% EtOAc/hexane) to give 3.47 g of the product (along with another 1.28 g of partially purified product). Mass Spec.: $MH^+$=555.9.

$^1$H NMR ($CDCl_3$, 300 MHz): 8.5 (s, 1H); 7.5 (s, 1H); 7.15 (s, 1H); 4.5 (s, 2H); 4.15 (m, 3H); 3.8 (brs, 2H); 3.4–3.1 (m, 4H); 9–2.75 (m, 1H); 2.7–2.5 (m, 2H); 2.4–2.2 (m, 2H); 1.25 (m, 3H).

Step D:

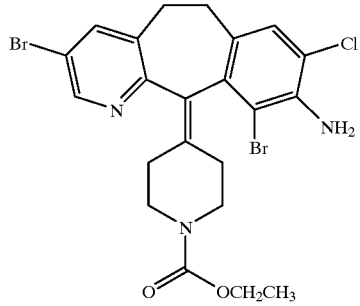

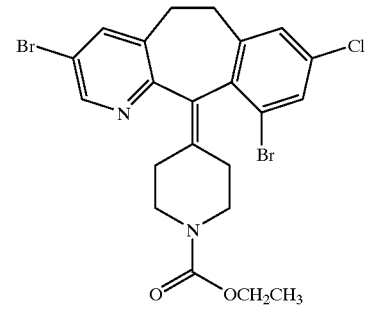

0.557 g (5.4 mmol) of t-butylnitrite and 3 mL of DMF were combined, and the mixture was heated at 60°–70° C. A mixture of 2.00 g (3.6 mmol) of the product of Step C and 4 mL of DMF, was slowly added dropwise and then the mixture was cooled to room temperature. Another 0.64 mL of t-butylnitrite was added at 40° C. and the mixture was reheated to 60°–70° C. for 0.5 hrs. The mixture was cooled to room temperature and poured into 150 mL of water. The mixture was extracted with $CH_2Cl_2$, the extract was dried over $MgSO_4$ and concentrated in vacuo to a residue. The residue was chromatographed (silica gel, 10%–20% EtOAc/hexane) to give 0.74 g of the product. Mass Spec.: $MH^+$= 541.0.

$^1$H NMR (CDCl3, 200 MHz): 8.52 (s, 1H); 7.5 (d, 2H); 7.2 (s, 1H); 4.15 (q, 2H); 3.9–3.7 (m, 2H); 3.5–3.1 (m, 4H); 3.0–2.5 (m, 2H); 2.4–2.2 (m, 2H); 2.1–1.9 (m, 2H); 1.26 (t, 3H).

Step E:

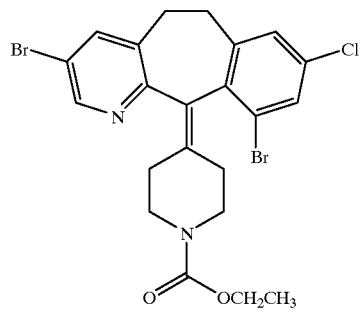

-continued

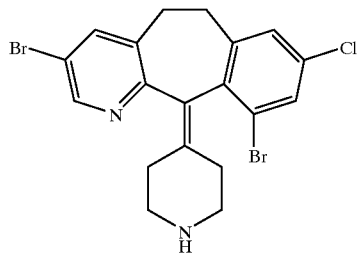

0.70 g (1.4 mmol) of the product of Step D and 8 mL of concentrated HCl (aqueous) were combined and the mixture was heated at reflux overnight. 30 mL of 1 N NaOH (aqueous) was added, then 5 mL of 50% NaOH (aqueous) and the mixture was extracted with $CH_2Cl_2$. The extract was dried over $MgSO_4$ and concentrated in vacuo to give 0.59 g of the title compound. Mass Spec.: $M^+$=468.7. m.p.= 123.9°–124.2° C.

PREPARATIVE EXAMPLE 5

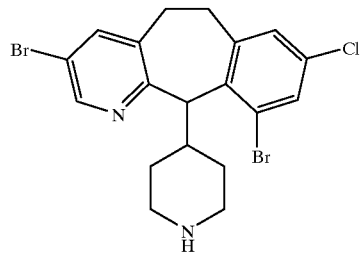

[racemic as well as (+)- and (−)-isomers]

Step A:

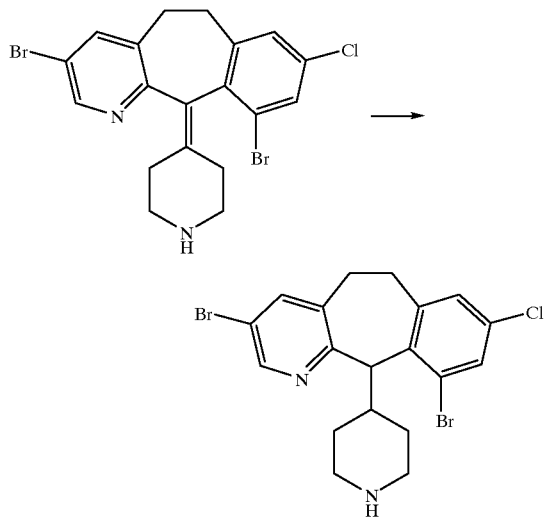

A solution of 8.1 g of the title compound from Preparative Example 4 in toluene was prepared and 17.3 mL of a 1M solution of DIBAL in toluene was added. The mixture was heated at reflux and another 21 mL of 1 M DIBAL/toluene solution was slowly added dropwise over a period of 40 min. The reaction mixture was cooled to about 0° C. and 700 mL of 1 M HCl (aqueous) was added. The organic phase was separated and discarded. The aqueous phase was washed with $CH_2Cl_2$, the extract was discarded, then the aqueous phase was basified by adding 50% NaOH (aqueous). The mixture was extracted with $CH_2Cl_2$, the extract was dried over $MgSO_4$ and concentrated in vacuo to give 7.30 g of the title compound, which is a racemic mixture of enantiomers.

Step B—Separation of Enantiomers:

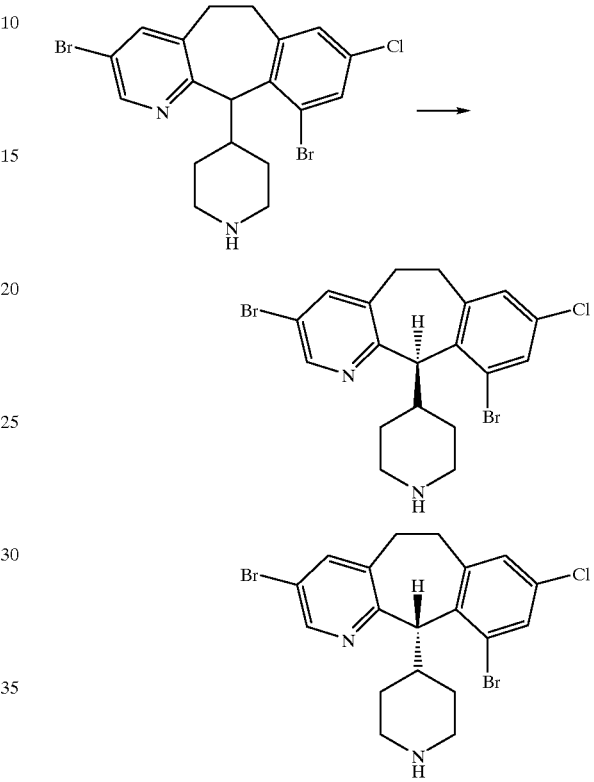

The racemic title compound of Step A was separated by preparative chiral chromatography (Chiralpack AD, 5 cm×50 cm column, using 20% iPrOH/hexane+0.2% diethylamine), to give the (+)-isomer and the (−)-isomer of the title compound.

Physical chemical data for (+)-isomer: m.p.=148.8° C.; Mass Spec. $MH^+$=472; $[\alpha]_D^{25}$=+65.6° (12.93 mg/2 mL MeOH).

Physical chemical data for (−)-isomer: m.p.=112° C.; Mass Spec. $MH^+$=472; $[\alpha]_D^{25}$=−65.2° (3.65 mg/2 mL MeOH).

PREPARATIVE EXAMPLE 6

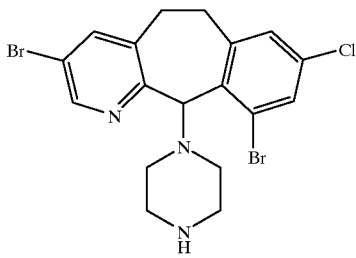

[racemic as well as (+)- and (-)-isomers]

Step A:

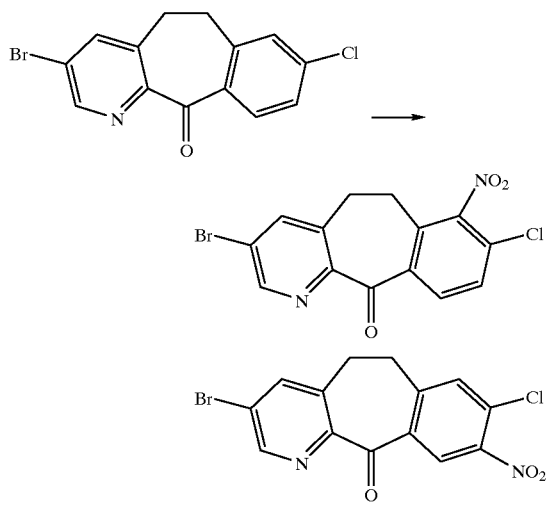

40.0 g (0.124 mole) of the starting ketone and 200 mL of H₂SO₄ were combined and cooled to 0° C. 13.78 g (0.136 mole) of KNO₃ were slowly added over a period of 1.5 hrs., then the mixture was warmed to room temperature and stirred overnight. The reaction was worked up using substantially the same procedure as described for Preparative Example 4, Step A. Chromatography (silica gel, 20%, 30%, 40%, 50% EtOAc/hexane, then 100% EtOAc) gave 28 g of the 9-nitro product, along with a smaller quantity of the 7-nitro product and 19 g of a mixture of the 7-nitro and 9-nitro compounds.

Step B:

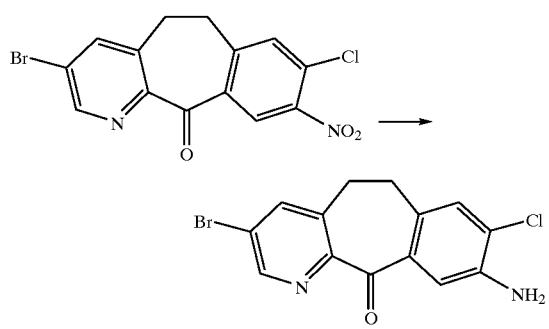

28 g (76.2 mmol) of the 9-nitro product of Step A, 400 mL of 85% EtOH/water, 3.8 g (34.3 mmol) of CaCl₂ and 38.28 g (0.685 mole) of Fe were reacted using substantially the same procedure as described for Preparative Example 4, Step C, to give 24 g of the product.

Step C:

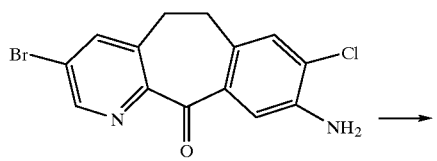

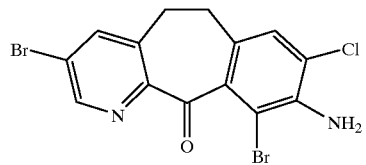

13 g (38.5 mmol) of the product of Step B and 140 mL of HOAc were combined and slowly added to a solution of 2.95 mL (57.8 mmol) of Br₂ in 10 mL of HOAc over a period of 20 min. The reaction mixture was stirred at room temperature, then concentrated in vacuo to a residue. CH₂Cl₂ and water were added, then the pH was adjusted to 8–9 with 50% NaOH (aqueous). The organic phase was washed with water, then brine and dried over Na₂SO₄ and concentrated in vacuo to give 11.3 g of the product.

Step D:

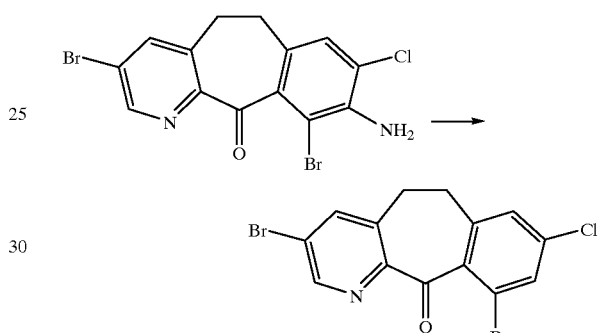

100 mL of concentrated HCl (aqueous) was cooled to 0° C., then 5.61 g (81.4 mmol) of NaNO₂ were added and the mixture was stirred for 10 min. 11.3 g (27.1 mmol) of the product of Step C was slowly added in portions and the mixture was stired at 0°–3° C. for 2.25 hrs. 180 mL of 50% H₃PO₂ (aqueous) was slowly added in portions and the mixture was allowed to stand at 0° C. overnight. 150 mL of 50% NaOH was slowly added in portions over 30 min., and the pH was adjusted to 9. The mixture was then extracted with CH₂Cl₂. The extract was washed with water, then brine and dried over Na₂SO₄. The mixture was concentrated in vacuo to a residue and chromatographed (silica gel, 2% EtOAc/CH₂Cl₂) to give 8.6 g of the product.

Step E:

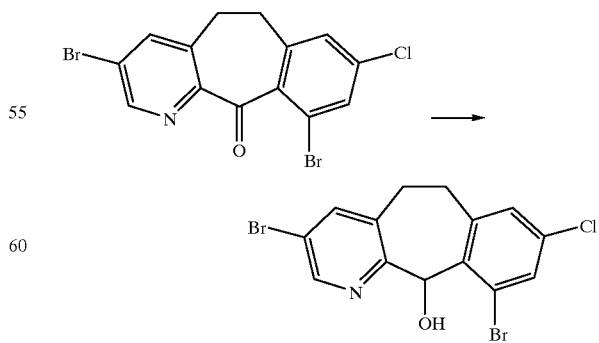

8.6 g (21.4 mmol) of the product of Step D and 300 mL of MeOH were combined and cooled to 0°–2° C. 1.21 g (32.1 mmol) of NaBH$_4$ was added and the mixture was stirred at ~0° C. for 1 hr. Another 0.121 g (3.21 mmol) of NaBH$_4$, was added and the mixture was stirred for 2 hr. at 0° C., then allowed to stand overnight at 0° C. It was concentrated in vacuo to a residue then the residue was partitioned between CH$_2$Cl$_2$ and water. The organic phase was separated and concentrated in vacuo (50° C.) to give 8.2 g of the product.

Step F:

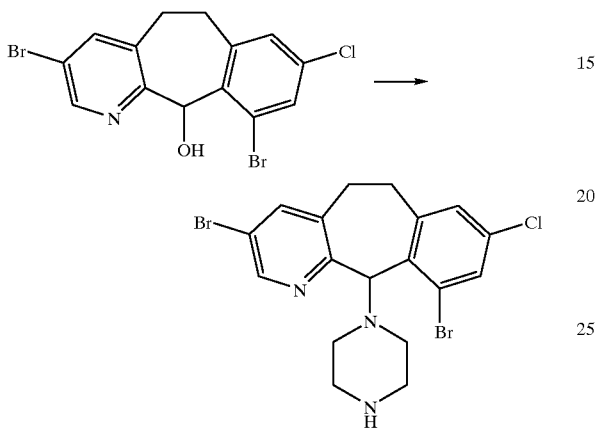

8.2 g (20.3 mmol) of the product of Step E was combined with 160 mL of CH$_2$Cl$_2$, cooled to 0° C., then 14.8 mL (203 mmol) of SOCl$_2$ was slowly added dropwise over a 30 minute period. The mixture was warmed to room temperature and stirred for 4.5 hrs., then concentrated in vacuo to a residue. CH$_2$Cl$_2$ was added and the mixture was washed with 1 N NaOH (aqueous) then brine and dried over Na$_2$SO$_4$. The residue was concentrated in vacuo to a residue, then dry THF was added and 8.7 g (101 mmol) of piperazine was added and the mixture was stirred at room temperature overnight. The residue was concentrated in vacuo to a residue, CH$_2$Cl$_2$, was added and the mixture was washed with 0.25 N NaOH (aqueous), water, then brine dried over Na$_2$SO$_4$ and concentrated in vacuo to give 9.46 g of the crude product. Chromatography (silica gel, 5% MeOH/CH$_2$Cl$_2$+NH$_3$) gave 3.59 g of the title compound, as a racemate. $^1$H NMR (CDCl$_3$, 200 MHz): 8.43 (d, 1H); 7.55 (d, 1H); 7.45 (d, 1H); 7.11 (d, 1H); 5.31 (s, 1H); 4.86–4.65 (m, 1H); 3.57–3.40 (m, 1H); 2.98–2.55 (m, 6H); 2.45–2.20 (m, 5H).

Step G—Separation of Enantiomers:

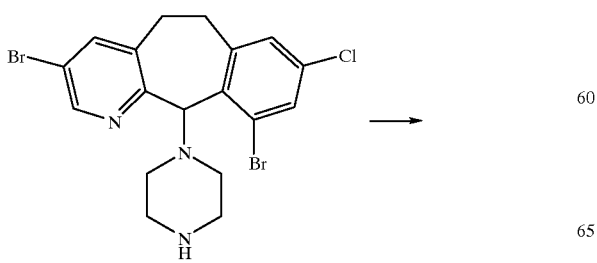

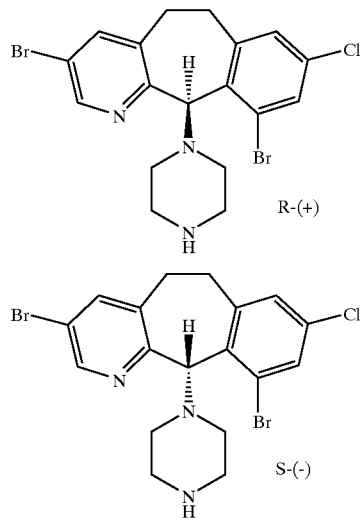

The racemic title compound from Step F (5.7 g) was chromatographed as described for Preparative Example 6, Step D, using 30% iPrOH/hexane+0.2% diethylamine, to give 2.88 g of the R-(+)-isomer and 2.77 g of the S-(-)-isomer of the title compound.

Physical chemical data for the R-(+)-isomer: Mass Spec. MH$^+$=472.0; $[\alpha]_D^{25}$=+12.1° (10.9 mg/2 mL MeOH).

Physical chemical data for the S-(-)-isomer: Mass Spec. MH$^+$=472.0; $[\alpha]_D^{25}$=-13.2° (11.51 mg/2 mL MeOH).

PREPARATIVE EXAMPLE 7

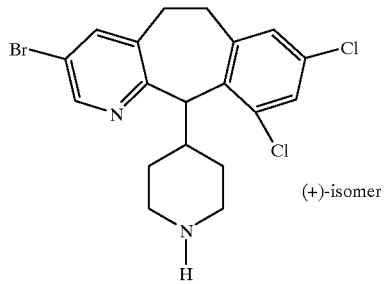

Step A:

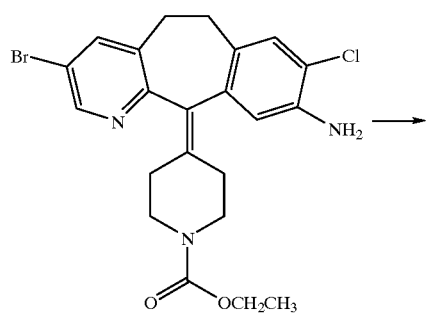

-continued

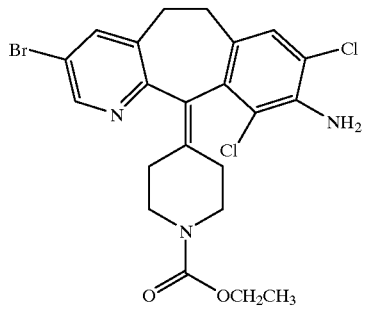

Dissolve 9.90 g (18.9 mmol) of the product of Preparative Example 4, Step B, in 150 mL CH$_2$Cl$_2$ and 200 mL of CH$_3$CN and heat to 60° C. Add 2.77 g (20.8 mmol) N-chlorosuccinimide and heat to reflux for 3 h., monitoring the reaction by TCL (30% EtOAc/H$_2$O). Add an additional 2.35 g (10.4 mmol) of N-chlorosuccinimide and reflux an additional 45 min. Cool the reaction mixture to room temperature and extract with 1 N NaOH and CH$_2$Cl$_2$. Dry the CH$_2$Cl$_2$ layer over MgSO$_4$, filter and purify by flash chromatography (1200 mL normal phase silica gel, eluting with 30% EtOAc/H$_2$O) to obtain 6.24 g of the desired product. M.p. 193–195.4° C.

Step B:

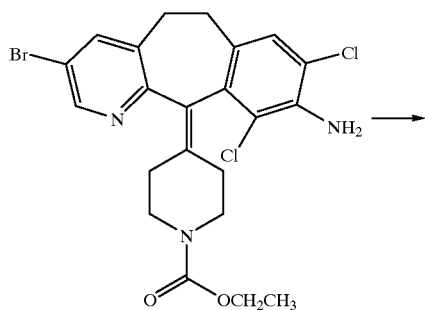

To 160 mL of conc. HCl at −10° C. add 2.07 g (30.1 mmol) NaNO$_2$ and stir for 10 min. Add 5.18 g (10.1 mmol) of the product of Step A and warm the reaction mixture from −10° C. to 0° C. for 2 h. Cool the reaction to −10° C., add 100 mL H$_3$PO$_2$ and let stand overnight. To extract the reaction mixture, pour over crushed ice and basifiy with 50% NaOH/CH$_2$Cl$_2$. Dry the organic layer over MgSO$_4$, filter and concentrate to dryness. Purify by flash chromatography (600 mL normal phase silica gel, eluting with 20% EtOAc/ hexane) to obtain 3.98 g of product. Mass spec.: MH$^+$= 497.2.

Step C:

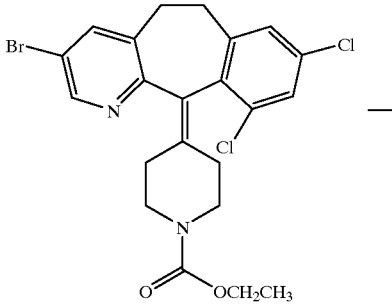

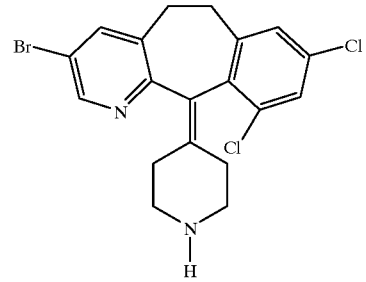

Dissolve 3.9 g of the product of Step B in 100 mL conc. HCl and reflux overnight. Cool the mixture, basify with 50% w/w NaOH and extract the resultant mixture with CH$_2$Cl$_2$. Dry the CH$_2$Cl$_2$ layer over MgSO$_4$, evaporate the solvent and dry under vacuum to obtain 3.09 g of the desired product. Mass spec.: MH$^+$=424.9.

Step D:

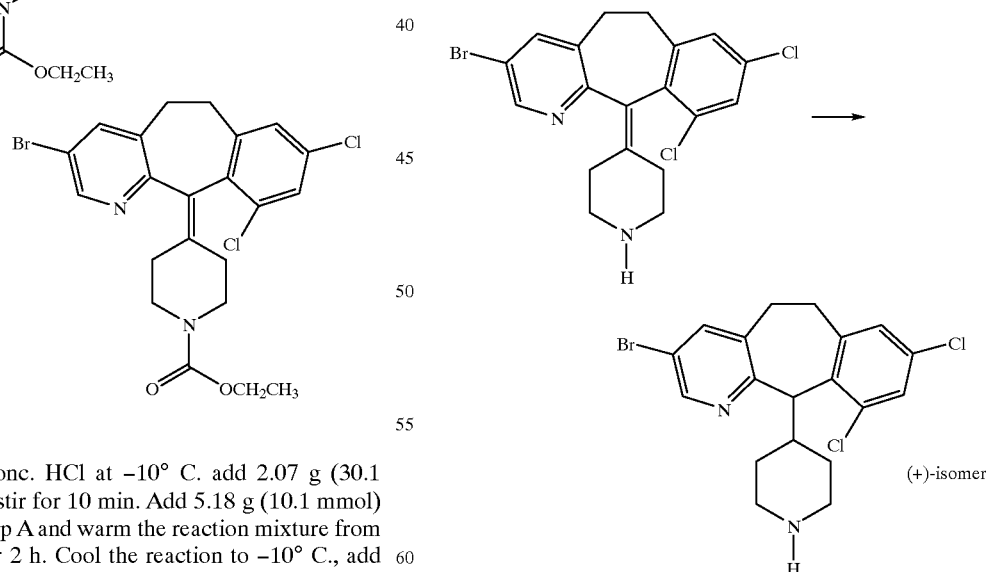

Using a procedure similar to that described in Preparative Example 6, obtain 1.73 g of the desired product, m.p. 169.6–170.1° C.; [a]$_D^{25}$=+48.2° (c=1, MeOH).

PREPARATIVE EXAMPLE 8

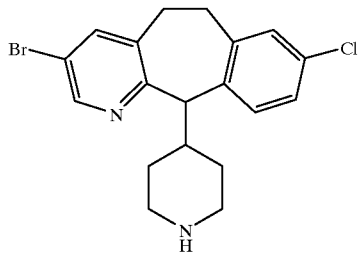

Step A:

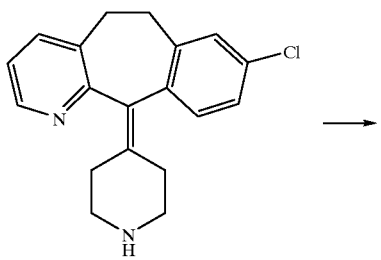

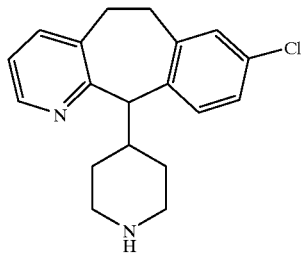

Combine 82.0 g (0.26 mole) of the product of Preparative Example 1, Step G, of WO 95/10516, and 1 L of toluene, then add 20.06 g (0.53 mole) of LiAlH$_4$ and heat the reaction mixture at reflux overnight. Cool the mixture to room temperature and add ~1 L of Et$_2$O, followed by dropwise addition of saturated Na$_2$SO$_4$ (aqueous) until a precipitate forms. Filter and stir the filtrate over MgSO$_4$ for 30 minutes, then concentrate in vacuo to give the product compound in 83% yield. Mass Spec.: MH$^+$=313

Step B:

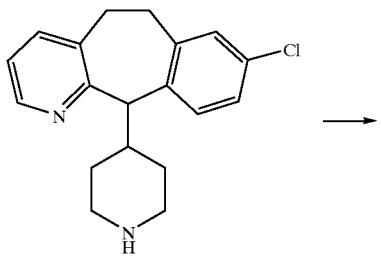

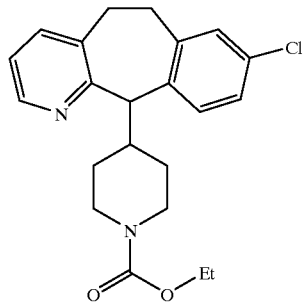

Combine 24.32 g (74.9 mmol) of the Product from Step A, 500 mL of toluene, 83 mL of Et$_3$N and 65.9 mL of ethyl chloroformate and heat the mixture at reflux overnight. Cool to 25° C., pour into 200 mL of water and extract with EtOAc. Dry the extract over MgSO$_4$, concentrate in vacuo to a residue and chromatograph (silica gel, 50% EtOAc/hexane) to give 15 g of the product compound. Mass Spec.: MH$^+$= 385.

Step C:

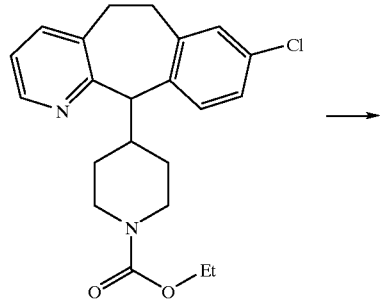

Dissolve 3.2 g (10.51 mmol) of tetra-n-butylammonium nitrate in 25 mL of CH$_2$Cl$_2$ and add 2.2 g (10.51 mmol, 1.5 mL) of TFAA. Cool to 0° C. and add the mixture (via cannula) to a solution of 3.68 g (9.56 mmol) of the product of Step B in 50 mL of CH$_2$Cl$_2$ at 0° C., then stir at 0° C. for 3 hours. Allow the mixture to warm to 25° C. while stirring overnight, then extract with saturated NaHCO$_3$ (aqueous) and dry over MgSO$_4$. Concentrate in vacuo to a residue and chromatograph (silica gel, 30% EtOAc/hexane) to give 1.2 g of the product compound. Mass Spec.: MH$^+$=430

Step D:

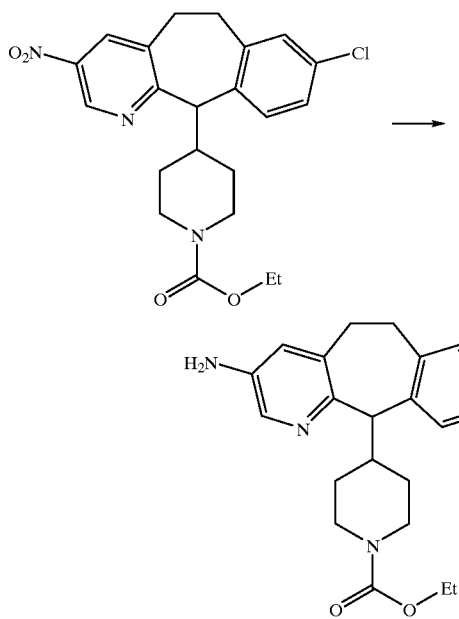

Combine 2.0 g (4.7 mmol) of the Product of Step C and 150 mL of 85% EtOH (aqueous), add 2.4 g (42 mmol) of Fe filings and 0.24 g (2.1 mmol) of $CaCl_2$, and heat at reflux for 16 hours. Filter the hot mixture through a bed of celite®, wash the celite® with hot EtOH. Concentrate the filtrate in vacuo to give a 100% yield of the product compound. Mass Spec.: $MH^+=400$.

Step E:

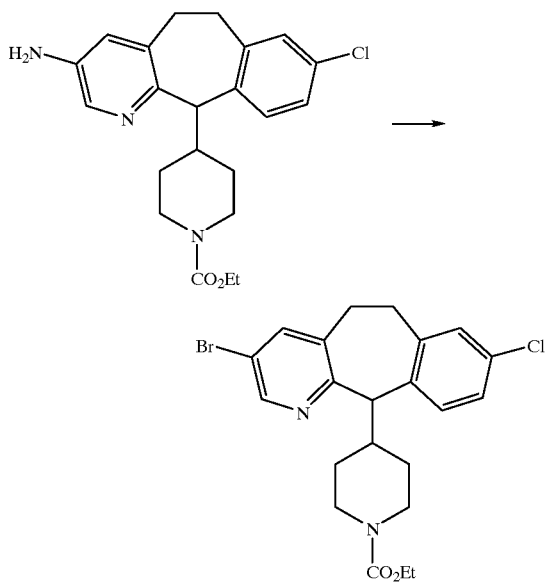

Combine 2.0 g (5.2 mmol) of the Product of Step D and 20 mL of 48% HBr, cool the mixture to −5° C. Add 1.4 mL of bromine and stir the mixture at −5° C. for 15 minutes and slowly add a solution of 1.07 g (15.5 mmol) of $NaNO_2$ in 10 mL of water. Stir for 45 minutes, then quench with 50% NaOH (aqueous) to pH ~10. Extract with EtOAc, dry the combined extracts over $MgSO_4$ and concentrate in vacuo to give the product compound. Mass Spec.: $MH^+=465$

Step F:

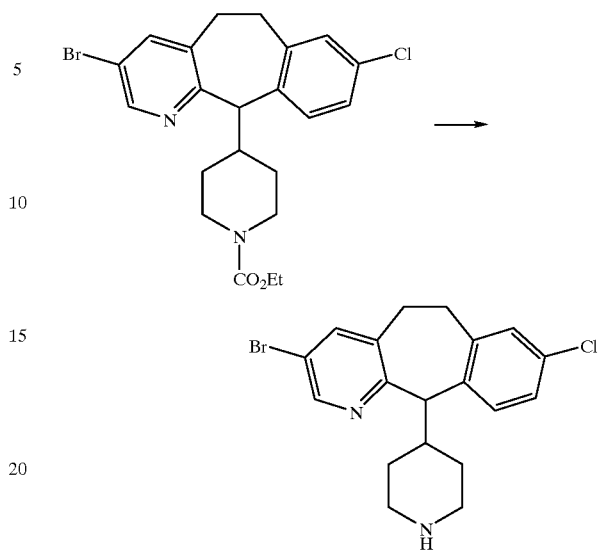

Hydroyze 4.0 g of the Product of Step E via substantially the same process as described for Example 358, Step A, of WO 95/10516, to give 1.39 g of the product compound. Mass Spec.: $MH^+=392$

EXAMPLE 1

(+)-4-(3-BROMO-8,10-DICHLORO-6,11-DIHYDRO-5H-BENZO[5,6]-CYCLOHEPTA[1,2-b]PYRIDIN-11-YL)-1-PIPERIDINE CARBOXAMIDE

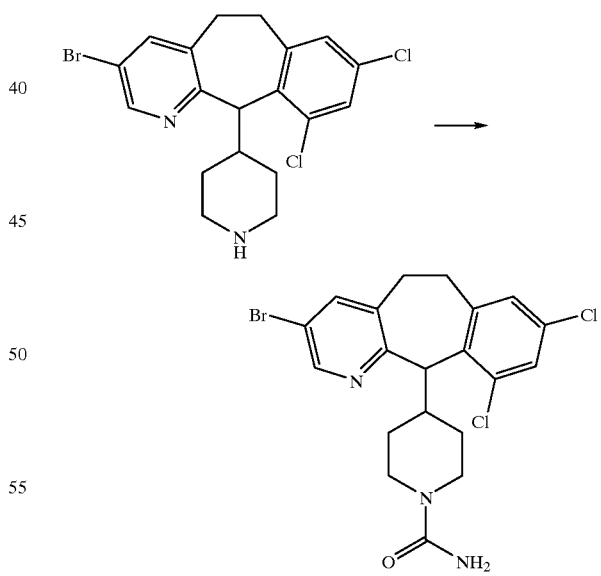

The title compound from preparative example 7 Step D (0.3 g, 0.7 mmol) and trimethylsilyl isocyanate (1.6 g, 2 mL, 14.1 mmol) were dissolved in $CH_2Cl_2$ (6 mL) and reaction stirred under nitrogen at room temperature for 72 h. Saturated aqueous sodium bicarbonate (20 mL) was then added. The desired product was extracted with $CH_2Cl_2$. Combined $CH_2Cl_2$ extracts were dried over $MgSO_4$ and concentrated in vacuo to give the title compound as a white solid (0.3 g, 97% yield, mp=101.9–102.8° C., MH+=470).

EXAMPLE 2

(+)-4-(3,10-DIBROMO-8-CHLORO-6,11-DIHYDRO-5H-BENZO[5,6]-CYCLO-HEPTA[1,2-b]PYRIDIN-11-YL)-1-[4-(DIMETHYLAMINO)-1-OXOBUTYL]PIPERIDINE

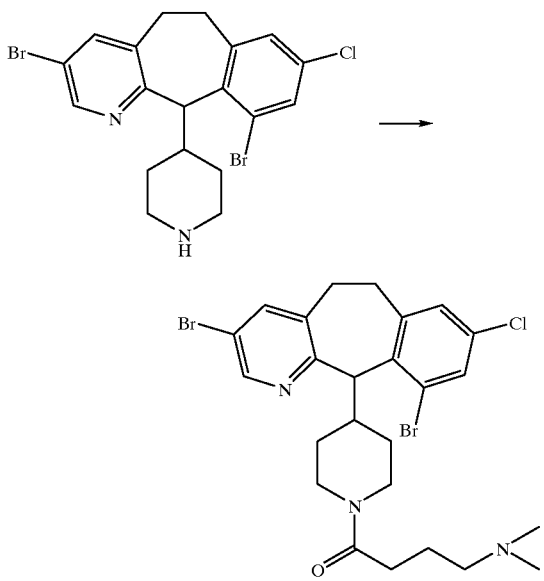

The title compound from Example 5 Step B-(+-isomer), was dissolved in DMF (7 mL) and then cooled to ~4° C. 4-(Dimethylamino)butyric acid hydrochloride salt, (0.13 g, 0.83 mmol) was then added followed by DEC (0.16 g, 0.83 mmol), HOBT (0.11 g, 0.83 mmol), and 4-methylmorpholine (0.08 g, 91 mM, 0.83 mmol) the reaction was then stirred at room temperature overnight. The reaction mixture was concentrated in vacuo to a residue that was partitioned between $CH_2Cl_2$ and Sat. $NaHCO_3$ (aqueous). The aqueous phase was extracted further with $CH_2Cl_2$. Combined $CH_2Cl_2$ fractions were dried over $MgSO_4$ and concentrated in vacuo to give a residue that was chromatographed on silica gel column using 10% (ammonia saturated methanol)/$CH_2Cl_2$ eluent to give the title compound as a white solid (0.3 g, 81% yield, mp=78–80° C., MH+=584).

EXAMPLE 3

(+)-1-(AMINOACETYL)-4-(3-BROMO-8,10-DICHLORO-6,11-DIHYDRO-5H-BENZO[5,6]CYCLO-HEPTA[1,2-b]PYRIDIN-11-YL)PIPERIDINE

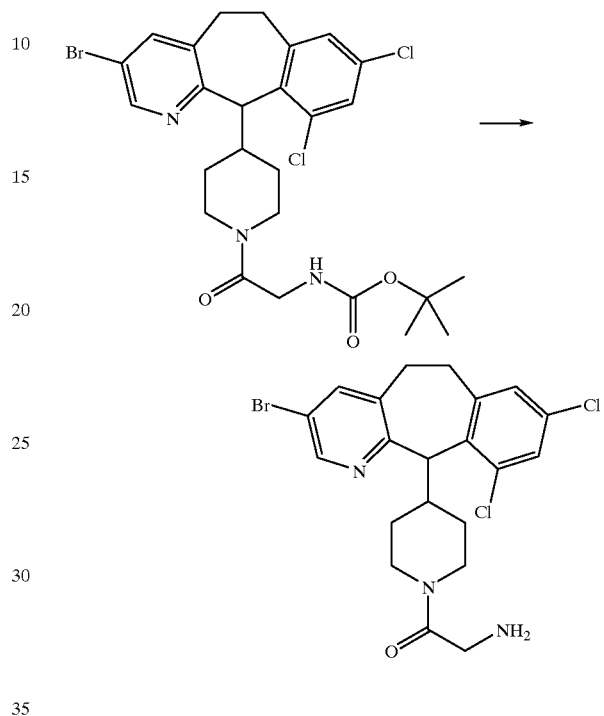

The title compound of Example 26 (0.6 g, 1.02 mmol) was dissolved in $CH_2Cl_2$ (6 mL) and trifluoroacetic acid (6 mL) was then added. The reaction mixture was stirred at room temperature for 4 h. It was the poured into ice and the pH was adjusted to 10 using 50% (w/v) aqueous NaOH. Reaction mixture was extracted with $CH_2Cl_2$. Combined $CH_2Cl_2$ extracts were washed with $H_2O$, brine, and dried over $Na_2SO_4$. The solvents were removed rotary evaporation to give the title compound as a white solid ((0.447 g, mp=81–122° C., MH+=484)

By essentially the same procedure as set forth in Example 2, but using the carboxylic acids in column 1 of Table 1 below, in place of 4-(Dimethylamino)butyric acid hydrochloride salt, and using (+)-4-(3-bromo-8,10-dichloro-6,11-dihydro-5H-benzo[5,6]cyclo-hepta[1,2-b]pyridin-11-yl)-1-piperidine instead of (+)-4-(3,10-dibromo-8-chloro-6,11-dihydro-5H-benzo[5,6]cyclo-hepta[1,2-b]pyridin-11-yl)-1-piperidine, (Title compound from Preparative example 7, Step D), one can obtain final products listed in column 2 of Table 1. The R group in Table 1 refers to compounds of formula (1.0)", just below.

TABLE 1

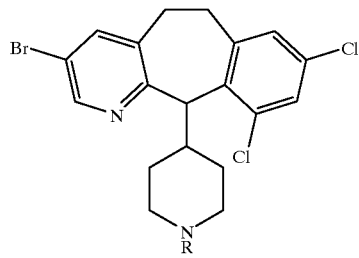
(1.0)"

| EXS | CARBOXYLIC ACID | —R | FINAL PRODUCTS |
|---|---|---|---|
| 4 | HOOC-CH2-N(CH3)2 | O=C-CH2-N(CH3)2 | Solid mp 80–81° C. MS MH+ = 512 |
| 5 | HOOC-CH2CH2-N(CH3)2 | O=C-CH2CH2-N(CH3)2 | Solid mp 84–85° C. MS MH+ = 526 |
| 6 | HOOC-(CH2)3-N(CH3)2 | O=C-(CH2)3-N(CH3)2 | Solid mp 78–79° C. MS MH+ = 540 |
| 7 | HOOC-(CH2)4-N(CH3)2 | O=C-(CH2)4-N(CH3)2 | Glass MS MH+ = 554 |
| 8 | HOOC-CH2CH2-N(C2H5)2 | O=C-CH2CH2-N(C2H5)2 | Solid mp 72–75° C. MS MH+ = 554 |
| 9 | HOOC-CH2CH2-piperidine | O=C-CH2CH2-piperidine | Solid mp 102–104° C. MS MH+ = 566 |
| 10 | HOOC-CH2-(2-oxopyrrolidin-1-yl) | O=C-CH2-(2-oxopyrrolidin-1-yl) | Solid mp 75–76° C. MS MH+ = 552 |
| 11 | HOOC-CH2CH2-(2,5-dioxopyrrolidin-1-yl) | O=C-CH2CH2-(2,5-dioxopyrrolidin-1-yl) | Solid mp 124–125° C. MS MH+ = 580 |

TABLE 1-continued

| # | Structure 1 | Structure 2 | Properties |
|---|---|---|---|
| 12 | HOOC-CH2-CH2-C(=O)-NH2 | CH3-C(=O)-CH2-CH2-C(=O)-NH2 | Solid<br>mp 134–135° C.<br>MS MH+ = 526 |
| 13 | HOOC-CH2-CH2-C(=O)-N(CH3)2 | CH3-C(=O)-CH2-CH2-C(=O)-N(CH3)2 | Solid<br>mp 78–79° C.<br>MS MH+ = 554 |
| 14 | HOOC-CH2-CH2-C(=O)-pyrrolidine | CH3-C(=O)-CH2-CH2-C(=O)-pyrrolidine | Solid<br>mp 85–86° C.<br>MS MH+ = 580 |
| 15 | HOOC-CH2-CH2-CH2-NH-C(=O)-CH3 | CH3-C(=O)-CH2-CH2-CH2-NH-C(=O)-CH3 | Solid<br>mp 92–94° C.<br>MS MH+ = 554 |
| 16 | HOOC-CH2-CH2-CH2-NH-C(=O)-NH-Ph | CH3-C(=O)-CH2-CH2-CH2-NH-C(=O)-NH-Ph | Solid<br>mp 115–117° C.<br>MS MH+ = 631 |
| 17 | HOOC-CH2-CH2-CH2-C(=O)-NH-(3-pyridyl) | CH3-C(=O)-CH2-CH2-CH2-C(=O)-NH-(3-pyridyl) | Solid<br>mp 109–110° C.<br>MS MH+ = 617 |
| 18 | HOOC-CH2-CH2-CH2-NH-C(=O)-(3-pyridyl) | CH3-C(=O)-CH2-CH2-CH2-NH-C(=O)-(3-pyridyl) | Solid<br>mp 111–112° C.<br>MS MH+ = 617 |
| 19 | HOOC-CH2-CH2-CH2-C(=O)-NH-Ph | CH3-C(=O)-CH2-CH2-CH2-C(=O)-NH-Ph | Solid<br>mp 77–78° C.<br>MS MH+ = 616 |
| 20 | HOOC-CH2-CH2-CH2-C(=O)-NH-(4-Cl-Ph) | CH3-C(=O)-CH2-CH2-CH2-C(=O)-NH-(4-Cl-Ph) | Solid<br>MS MH+ = 650 |
| 21 | HOOC-CH2-CH2-CH2-C(=O)-NH-CH2-Ph | CH3-C(=O)-CH2-CH2-CH2-C(=O)-NH-CH2-Ph | Solid<br>MS MH+ = 630 |

TABLE 1-continued

| | | | |
|---|---|---|---|
| 22 | (structure: HOOC-(CH2)3-NH-C(O)-Ph) | (structure: CH3-C(O)-(CH2)3-NH-C(O)-Ph) | Solid<br>mp<br>66–67° C.<br>MS MH$^+$ = 630 |
| 23 | (structure: HOOC-(CH2)4-N(maleimide)) | (structure: CH3-C(O)-(CH2)4-N(maleimide)) | Solid<br>MS MH$^+$ = 620 |
| 24 | (structure: HOOC-(CH2)3-NH-C(O)-4-pyridyl) | (structure: CH3-C(O)-(CH2)3-NH-C(O)-4-pyridyl) | Solid<br>mp<br>130–131° C.<br>MS MH$^+$ = 617 |
| 25 | (structure: HOOC-(CH2)3-NH-C(O)-O-tBu) | (structure: CH3-C(O)-(CH2)3-NH-C(O)-O-tBu) | Solid<br>mp<br>93–99° C.<br>MS MH$^+$ = 612<br>$\alpha D^{24}$ = 48.2°,<br>c = 0.23,<br>CH$_2$Cl$_2$ |
| 26 | (structure: HOOC-CH2-NH-C(O)-O-tBu) | (structure: CH3-C(O)-CH2-NH-C(O)-O-tBu) | Solid<br>mp<br>103–117<br>MS MH$^+$ = 584 |
| 40 | (structure: HOOC-CH2-CH2-C(O)-O-CH3) | (structure: CH3-C(O)-CH2-CH2-C(O)-O-CH3) | Solid<br>mp = 72–73° C.<br>MS MH$^+$ = 541 |
| 41 | (structure: HOOC-(CH2)3-C(O)-OCH3) | (structure: CH3-C(O)-(CH2)3-C(O)-OCH3) | Solid<br>MS MH$^+$ = 555 |

EXAMPLE 27

(+)-1-(4-AMINO-1-OXOBUTYL)-4-(3-BROMO-8,10-DICHLORO-6,11-DIHYDRO-5H-BENZO[5,6]CYCLO-HEPTA[1,2-b]PYRIDIN-11-YL)PIPERIDINE

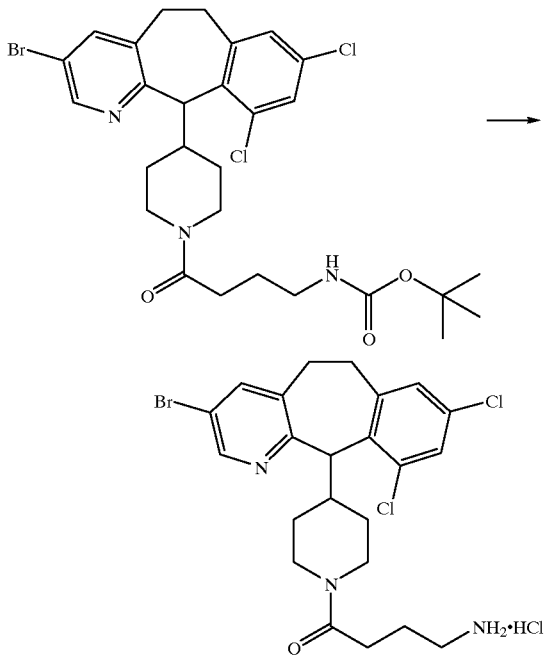

The title compound is prepared from the title compound of Example 25, following essentially the same procedure as described for Example 3 except that HCl in dioxane was used instead of TFA to obtain the title compounds as a white solid (mp=112–118° C., MH=512). $\alpha_D^{24}$=64.0°, c=$_{0.14}$, ethanol

EXAMPLE 28

(+)-N-[2-[4-(3-BROMO-8,10-DICHLORO-6,11-DIHYDRO-5H-BENZO[5,6]CYCLO-HEPTA[1,2-b]PYRIDIN-11-YL)PIPERIDINYL]-2-OXOETHYL]METHANESULFONAMIDE

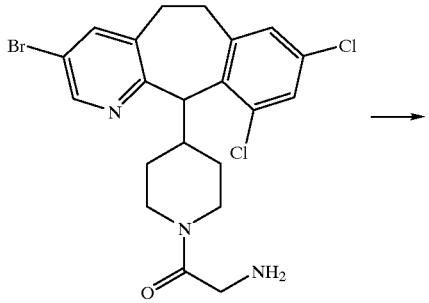

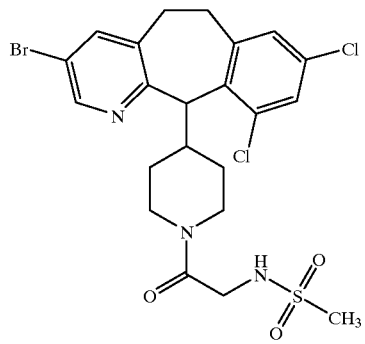

The title compound of Example 3 (0.15 g, 0.31 mmol) was dissolved in CH$_2$Cl$_2$ (1.5 mL). 4-Methylmorpholine (102 uL), followed by mesyl chloride (36 uL, 0.47 mmol, 1.5 equiv.) was then added. Reaction mixture was stirred at room tempearture overnite. The CH$_2$Cl$_2$ phase was washed twice with Sat. NaHCO$_3$, brine and then dried over Na$_2$SO$_4$. CH$_2$Cl$_2$ was then removed by rotary evaporation and resulting residue was purified on silica gel column eluting with 30% EtOAc/CH2Cl2 to give the title compound as a white solid (0.109 g, mp=120–140° C., MH$^+$==562.

EXAMPLE 29

(+)-N-[4-[4-(3-BROMO-8,10-DICHLORO-6,11-DIHYDRO-5H-BENZO[5,6]CYCLO-HEPTA[1,2-b]PYRIDIN-11-YL)PIPERIDINYL]-2-OXOBUTYL]METHANESULFONAMIDE

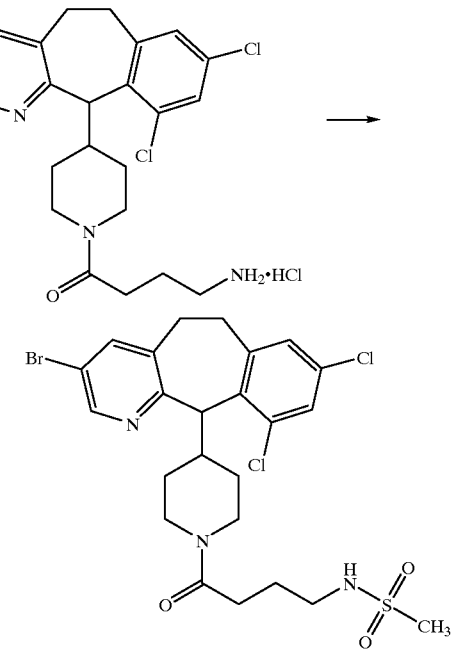

The title compound is prepared from the title compound of Example 27, following essentially the same procedure as described for Example 28 to obtain the title compound as a white solid (mp=110–113° C., MH=590).

EXAMPLE 30

(+)-N-[2-[4-(3-BROMO-8,10-DICHLORO-6,11-DIHYDRO-5H-BENZO[5,6]CYCLO-HEPTA[1,2-b]PYRIDIN-11-YL)PIPERIDINYL]-2-OXOETHYL]UREA

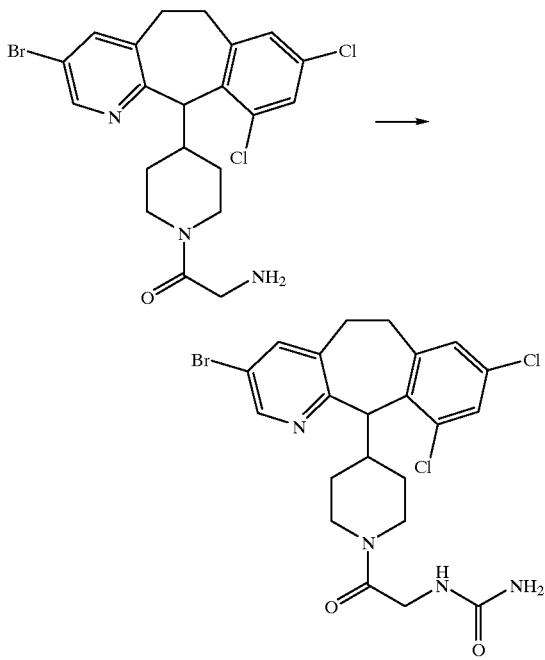

The title compound is prepared from the title compound of Example 3, following essentially the same procedure as described for Example 1 to obtain the title compound as a white solid (MH$^+$=527)

EXAMPLE 31

(+)-N-[2-[4-(3-BROMO-8,10-DICHLORO-6,11-DIHYDRO-5H-BENZO[5,6]CYCLO-HEPTA[1,2-b]PYRIDIN-11-YL)PIPERIDINYL]-2-OXOBUTYL]UREA

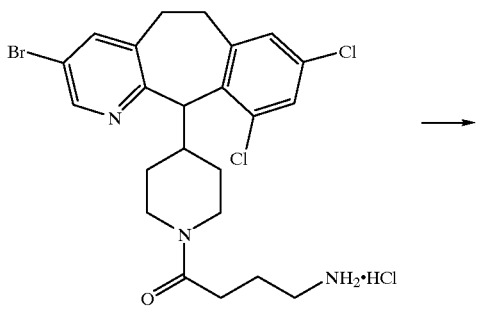

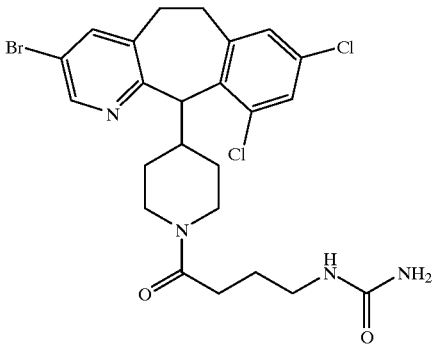

The title compound of Example 27 (0.05 g, 0.091 mmol) was dissolved in H$_2$O (1 mL) and urea (0.055 g, 0.9 mmol) was added. The reaction was heated at ~78° C. overnight. Reaction mixture was partitioned between 1 N NaOH and CH$_2$CL$_2$. CH$_2$Cl$_2$ fraction was dried over MgSO$_4$ and concentrated. The residue was purified on silica gel on a plate eluting with 5% MeOH (sat. with ammonia)-CH$_2$CL$_2$ eluent to give the title compound as a light yellow powder (MH$^+$=555, mp=182–190° C.).

EXAMPLE 32

(+)-4-(3,10-DIBROMO-8-CHLORO-6,11-DIHYDRO-5H-BENZO[5,6]CYCLO-HEPTA[1,2-b]PYRIDIN-11-YL)-1-[4-(1,3-DIHYDRO-1,3-DIOXO-2H-ISOINDOL-2-YL)-1-OXOBUTYL]PIPERIDINE

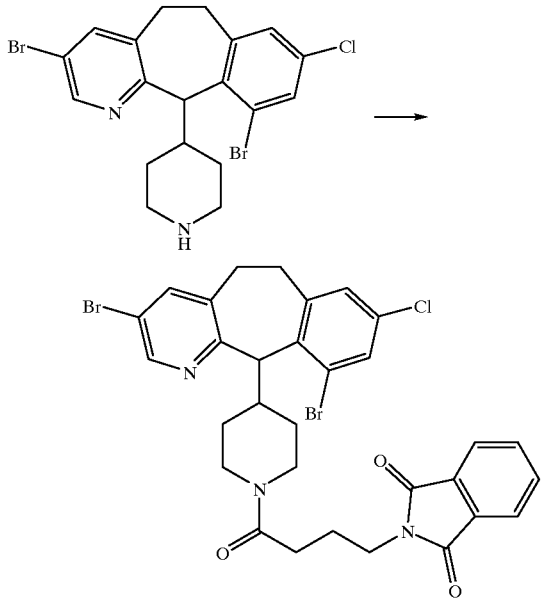

The title compound from preparative example 5, Step B (+enantiomer) (100 mg, 0.21 mmole) was dissolved in 2 mL DMF and 1-hydroxybenzotriazole hydrate (43 mg, 0.32 mmole), 4(1,3-dioxo-1,3-dihydroisoindol-2-yl)butyric acid (0.02 mL, 0.32 mmole), 1-methylmorpholine (0.04 mL, 0.32 mmole) and 1-(3-dimethylaminopropyl)-3-ethylcarbodiimide hydrochloride 61 mg, 0.32 mmole) were added. The resulting mixture was stirred at room temperature for 65 h and poured into 10 mL saturated NaHCO₃ solution. The aqueous mixture was extracted with dichloromethane and the organic solution washed with brine and water, dried with MgSO₄, and evaporated. The resulting residue was purified by silica gel chromatography using 2.5% (ammonia saturated methanol)/dichloromethane as eluent to yield 107 mg of the title compound as a white solid (mp 100.5°–101.8° C., MH⁺686).

EXAMPLE 33

4-(8,10-DICHLORO-3-BROMO-6,11-DIHYDRO-5H-BENZO[5,6]CYCLO-HEPTA[1,2-b]PYRIDIN-11-YL)-1-[4-(1,3-DIHYDRO-1,3-DIOXO-2H-PYRROLO-[3,4c]-PYRIDINE-2-YL)-1-OXOBUTYL]PIPERIDINE

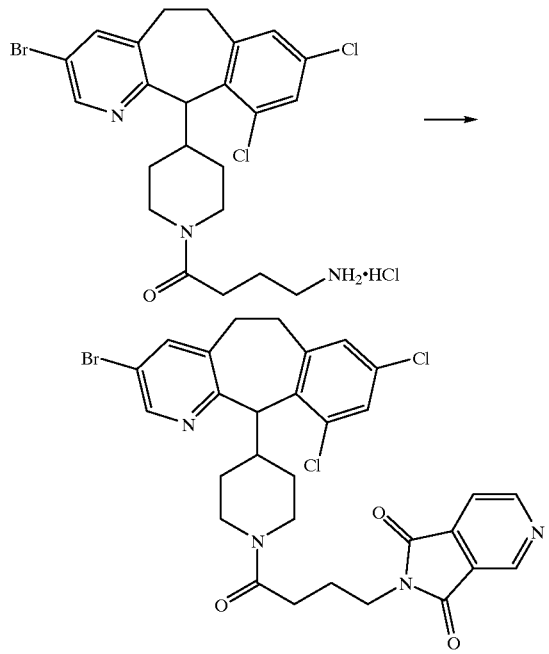

The title compound of Example 27 (93.3 mg, 0.171 mmole) was dissolved in 0.75 mL DMF and triethylamine (50 μL, 0.36 mmole) and 3,4-pyridinedicarboxylic anhydride (30.4 mg, 0.204 mmole) were added. The mixture was stirred at room temperature for 4.5 h, heated to 40° to 50° C. for ½ h then evaporated to dryness. The residue was suspended in 1 mL acetic anhydride and heated to 85°–95° C. for 24 h. The mixture was evaporated to dryness. The residue was dissolved in 2 mL DMF and 0.5 mL water, heated on a steam bath for ½ h then added to a stirred solution of NaHCO₃ (170.3 mg) in 10 mL water. The resulting suspension was filtered and the filter cake washed with water then dried at 50° C. under vacuum for 16 h to give 81.9 mg of the title compound as a white solid. mp 105.9–112.2° C., MH⁺643.

EXAMPLE 34

4-(8,10-DICHLORO-3-BROMO-6,11-DIHYDRO-5H-BENZO[5,6]CYCLO-HEPTA[1,2-b]PYRIDIN-11-YL)-1-[4-(1,3-DIHYDRO-1,3-DIOXO-2H-PYRROLO-[3,4b]-PYRIDINE-2-YL)-1-OXOBUTYL]PIPERIDINE

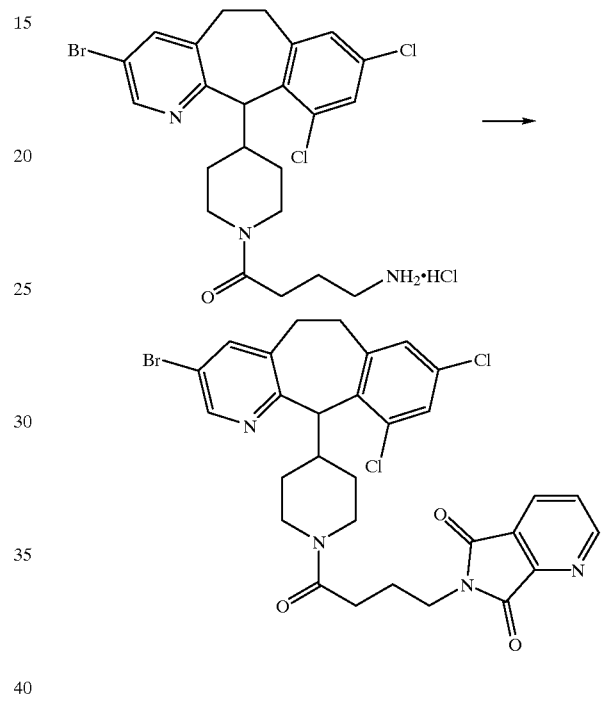

The title compound of example 27 (104 mg, 0.191 mmole) was dissolved in 0.75 mL DMF and triethylamine (50 μL, 0.36 mmole) and 2,3-pyridinedicarboxylic anhydride (301.6 mg, 0.212 mmole) were added. The mixture was stirred at room temperature for 2 h and evaporated to dryness. The residue was suspended in 1 mL acetic anhydride and heated to 70° to 80° C. for 2 hours and evaporated to dryness. The residue was dissolved in 1.5 mL hot DMF and added to a solution of 146 mg NaHCO₃ in 10 mL water. The resulting precipitate was filtered, washed with water and vacuum dried at 50° C. for 16 h to afford 74.0 mg of the title compound as a white solid (mp 126.0°–135.2° C., heating 2 to 3° C. per minute), MH⁺643.

EXAMPLE 35

4-(8,10-DICHLORO-3-BROMO-6,11-DIHYDRO-5H-BENZO[5,6]CYCLO-HEPTA[1,2-b]PYRIDIN-11-YL)-1-[4-(1,3-DIHYDRO-1,3-DIOXO-2H-PYRROLO-[3,4b]-PYRAZINE-2-YL)-1-OXOBUTYL]PIPERIDINE

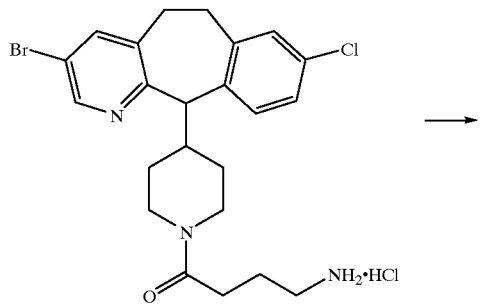

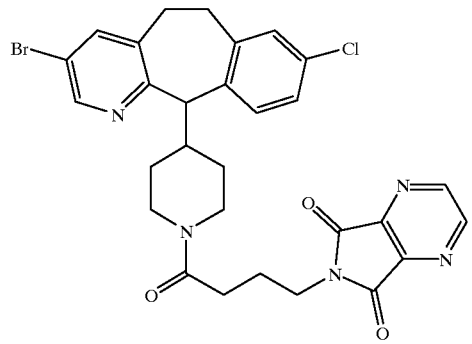

The procedure of Example 33 was followed using 100.0 mg (0.19 mmole) of the title compound of Example 37 44.0 mg (0.241 mmole) 2,3-pyrazinedicarboxylic anhydride and 55 µL triethylamine in 0.75 mL DMF. Following the procedure described in Example 33 the title compound was obtained as a white solid mp 124.0–125.5° C., MH⁺610.

EXAMPLE 36

(+/−)-1-(5-AZA-8,8 DIMETHYL-1,6-DIOXO-7-OXYNONYL)-4-(3-BROMO-8-CHLORO-6,11-DIHYDRO-5H-BENZO[5,6]CYCLOHEPTA-[1,2b]PYRIDIN-11-YL)PIPERIDINE

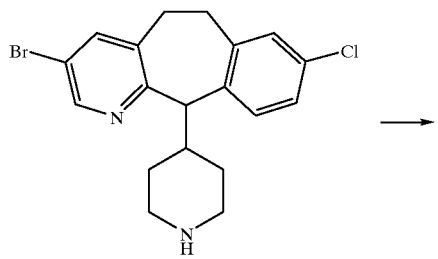

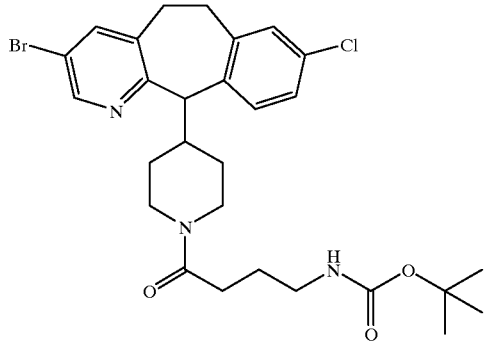

The title compound is prepared from the title compound of preparative example 8 following essentially the same procedure as described for the preparation of the starting material of Example 27 (mp=90.3–93.4° C., MH+=578).

EXAMPLE 37

(+/−)-1-(4-AMINO-1-OXOBUTYL)-4-(3-BROMO-8-CHLORO-6,11-DIHYDRO-5H-BENZO[5,6]CYCLOHEPTA[1,2b]PYRIDIN-11-YL)PIPERIDINE

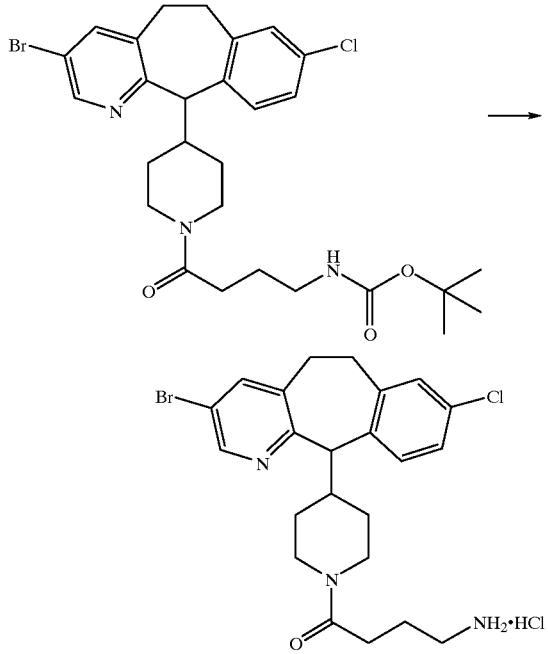

The title compound is prepared from the title compound of Example 36, following essentially the same procedure as described for Example 27 to obtain the title compound as a pale yellow solid (mp 50.8–55.5° C.), MH⁺478.

EXAMPLE 38

(+)-4-(3-BROMO-8,10-DICHLORO-6,11-DIHYDRO-5H-BENZO[5,6]CYCLO-HEPTA[1,2-b]PYRIDIN-11-YL)-1-[4-(PIPERIDINYL)-1-OXOBUTYL]PIPIRIDINE

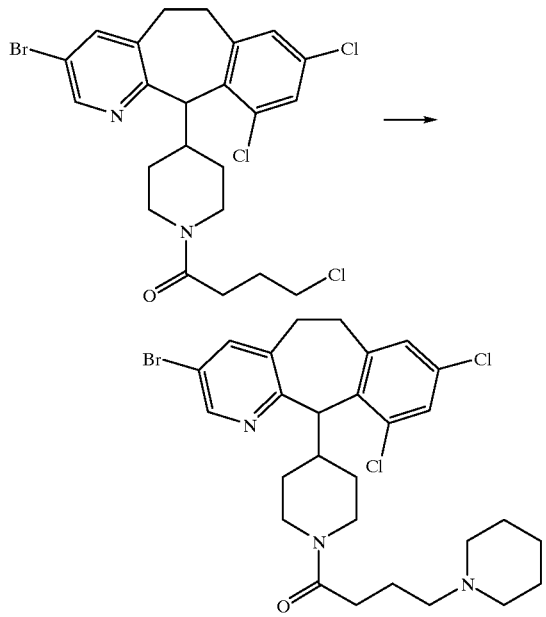

The title compound of Preparative Example 3 (0.1 g, 0.17 mmol) and pipiridine (0.1 mL, 1.04 mmol) were dissolved in 5 mL of $CH_2Cl_2$ and stirred at room temperature for 48 h. All the volatile solvents were removed and the resulting crude product was purified on a silica gel prep plate eluting with 20% MeOH—$NH_3$—$CH_2Cl_2$ to give 0.02 g of the title compound FAB-MS: $MH^+$=580

EXAMPLE 39

(+)-4-(3-BROMO-8,10-DICHLORO-6,11-DIHYDRO-5H-BENZO[5,6]CYCLO-HEPTA[1,2-b]PYRIDIN-11-YL)-1-[4-(MORPHOLINYL)-1-OXOBUTYL]PIPIRIDINE

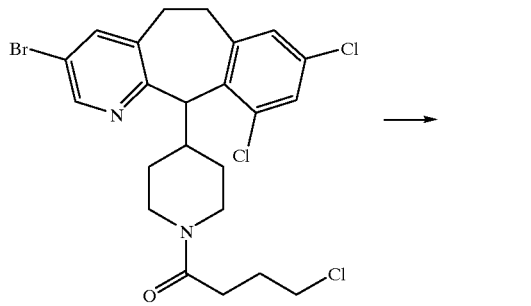

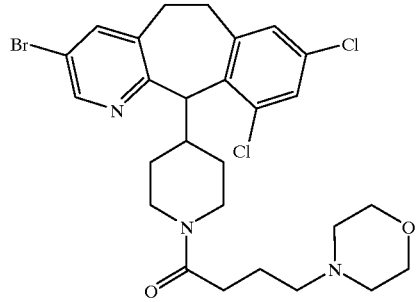

The title compound is prepared following essentially the same procedure as described in Example 38 except that morpholine was used instead of pipiridine to obtain a solid FAB-MS: $MH^+$=582.

EXAMPLE 42

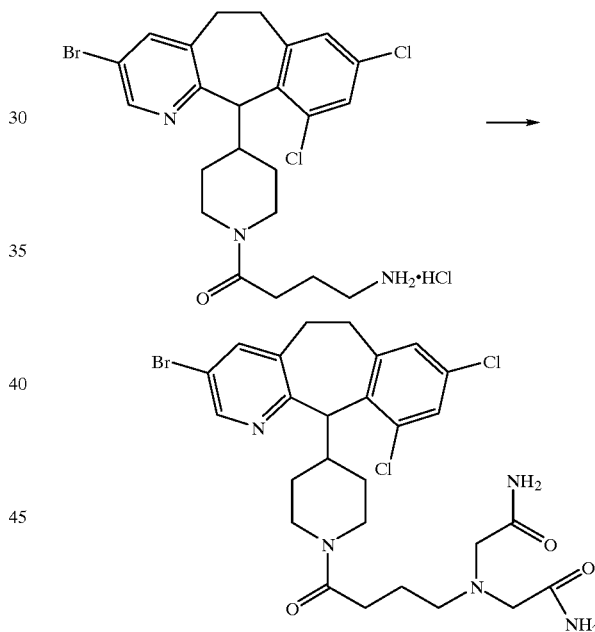

The title compound of Example 27 (0.1 g, 0.18 mmole), bromoacetamide (0.04 g, 0.3 mmole) and potassium carbonate were dissolved in 2 ml of DMF and allowed to stand for 18 hours. The reaction mixture was concentrated in vacuo. The residue was dissolved in ethyl acetate, washed with water, dried over magnesium sulfate, and concentrated to give a white solid. mp=110° C. to 123° C., MH=626, $\alpha_D^{24}=+30.6°$, c=0:17, $CH_2Cl_2$.

EXAMPLE 43

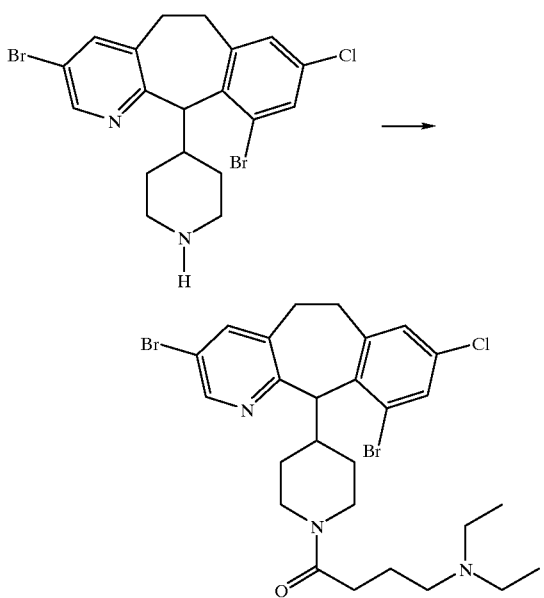

The title compound was prepared by essentially the same procedure as described in Example 2 except that 4-(diethylamino)butyric acid was used in place of 4-(methylamino)butyric acid, mp=69.9–70.1° C.

EXAMPLE 44

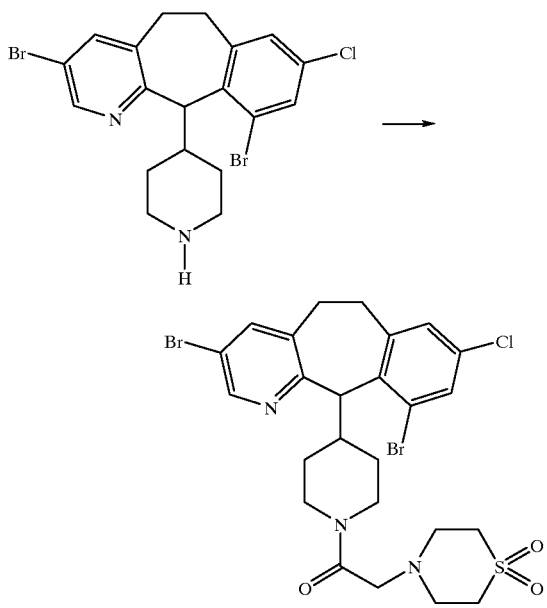

The title compound was prepared by essentially the same procedure as described in Example 2 except that 4-(diethylamino)butyric acid was replaced with thiomorpholine S-dioxide acetic acid.

EXAMPLE 45

(+)-ETHYL 4-(3,10-DIBROMO-8-CHLORO-6,11-DIHYDRO-5H-BENZO[5,6]CYCLO-HEPTA[1,2-b]PYRIDIN-11(R)-YL)-BETA-OXO-1-PIPERIDININE PROPANOATE

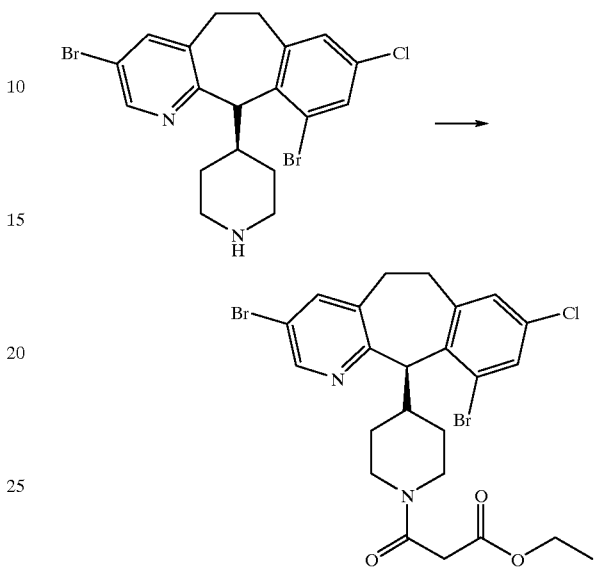

The product of Preparative Example 5, Step B −(+-isomer) (0.4 g, 0.85 mmol), was dissolved in DMF (10 mL) and then cooled to ~4° C. Mono ethyl malonate potassium salt (0.19 g, 1.1 mmol) was then added, followed by DEC (0.2 g, 1.1 mmol), HOBT (0.15 g, 1.1 mmol), and 4-methylmorpholine (0.11 g, 0.12 μL, 1.1 mmol). The reaction was then stirred at room temperature overnight. The reaction mixture was concentrated in vacuo to a residue that was partitioned between $CH_2Cl_2$ and sat. $NaHCO_3$ (aqueous). The aqueous phase was extracted further with $CH_2Cl_2$, the combined $CH_2Cl_2$ fractions were dried over $MgSO_4$ and concentrated in vacuo. The resultant residue was chromatographed on a silica gel column using 50% EtOAc-Hexanes as eluent to give the title compound as a white solid (0.41 g, 82% yield, m.p.=86–87° C., $MH^+$=585).

EXAMPLE 46

(+)-SODIUM 4-(3,10-DIBROMO-8-CHLORO-6,11-DIHYDRO-5H-BENZO[5,6]CYCLO-HEPTA[1,2-b]PYRIDIN-11(R)-YL)-BETA-OXO-1-PIPERIDININE PROPANOATE

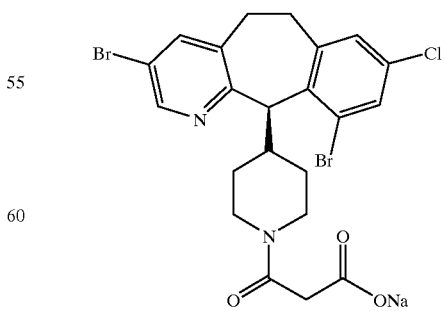

The product of Example 45 (0.34 g, 0.58 mmol) was dissolved in absolute EtOH (10 mL). $H_2O$ (0.7 mL) was then added, followed by NaOH (0.03 g, 0.7 mmol). The reaction mixture was stirred at room temperature for 16 h. The solvents were removed by rotary evaporation to give the title compound as a white solid (0.34 g, 100% yield, m.p.=230° C. (decomposed), MH$^+$=556).

EXAMPLE 47

4-(3,10-DIBROMO-8-CHLORO-6,11-DIHYDRO-5H-BENZO[5,6]CYCLO-HEPTA[1,2-b]PYRIDIN-11(R)-YL)-BETA-OXO-1-PIPERIDININE PROPANAMIDE

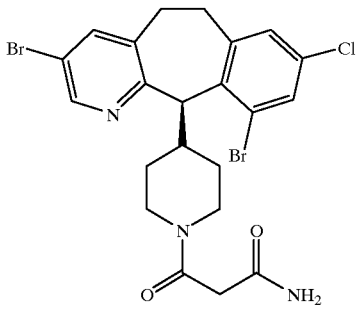

The product of Example 46 (0.4 g, 0.72 mmol), was dissolved in DMF (10 mL) and then cooled to ~4° C. NH$_4$Cl (0.05 g, 0.94 mmol) was added, followed by DEC (0.17 g, 0.94 mmol), HOBT (0.13 g, 0.94 mmol), and 4-methylmorpholine (0.09 g, 0.1 μL, 0.094 mmol). The reaction was then stirred at room temperature overnight. The reaction mixture was concentrated in vacuo to a residue which was partitioned between CH$_2$Cl$_2$ and sat. NaHCO$_3$ (aqueous). The aqueous phase was extracted further with CH$_2$Cl$_2$, the combined CH$_2$Cl$_2$ fractions were dried over MgSO$_4$ and concentrated in vacuo. The resultant residue was chromatographed on a silica gel column using 50% EtOAc-Hexanes as eluent to give the title compound as a white solid (0.22 g, 55% yield, m.p.=143–144° C., MH$^+$=556).

EXAMPLE 48

(+)-METHYL 4-(3,10-DIBROMO-8-CHLORO-6,11-DIHYDRO-5H-BENZO[5,6]CYCLO-HEPTA[1,2-b]PYRIDIN-11(R)-YL)-GAMMA-OXO-1-PIPERIDININE BUTANOATE

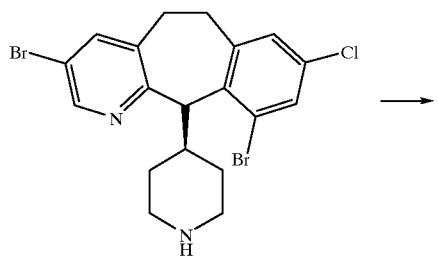

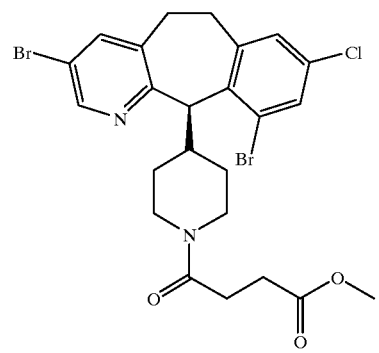

The title compound is prepared following essentially the same procedure as described for Example 45, using the appropriate diacid monoester to obtain the title compound as a white solid (yield=72% m,p,=78–79° C., MH$^+$=584).

EXAMPLE 49

(+)-SODIUM 4-(3,10-DIBROMO-8-CHLORO-6,11-DIHYDRO-5H-BENZO[5,6]CYCLO-HEPTA[1,2-b]PYRIDIN-11(R)-YL)-GAMMA-OXO-1-PIPERIDININE BUTANOATE

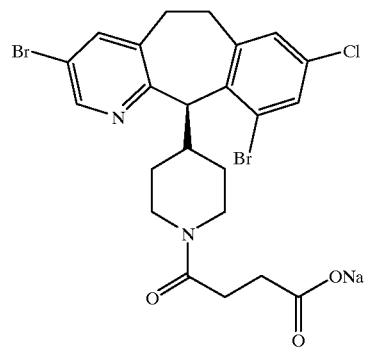

The title compound is prepared from the product of Example 48 following essentially the same procedure as described for Example 46 to obtain the title compound as a white solid (94% yield, m.p.=270° C. (decomposed), MH$^+$=570).

EXAMPLE 50

(+)-4-(3,10-DIBROMO-8-CHLORO-6,11-DIHYDRO-5H-BENZO[5,6]CYCLO-HEPTA[1,2-b]PYRIDIN-11(R)-YL)-GAMMA-OXO-1-PIPERIDININE BUTANAMIDE

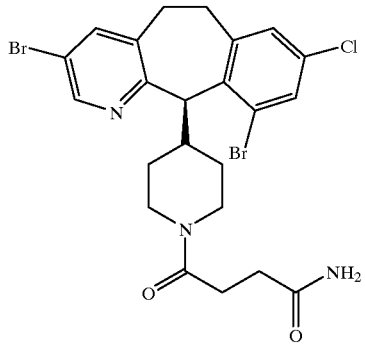

The title compound is prepared from the product of Example 49 following essentially the same procedure as described for Example 47 to obtain a white solid (yield=45%, m.p.=134–135° C., MH$^+$=570).

EXAMPLE 51

(+)-METHYL 4-(3,10-DIBROMO-8-CHLORO-6,11-DIHYDRO-5H-BENZO[5,6]CYCLO-HEPTA[1,2-b]PYRIDIN-11(R)-YL)-DELTA-OXO-1-PIPERIDININE PENTANOATE

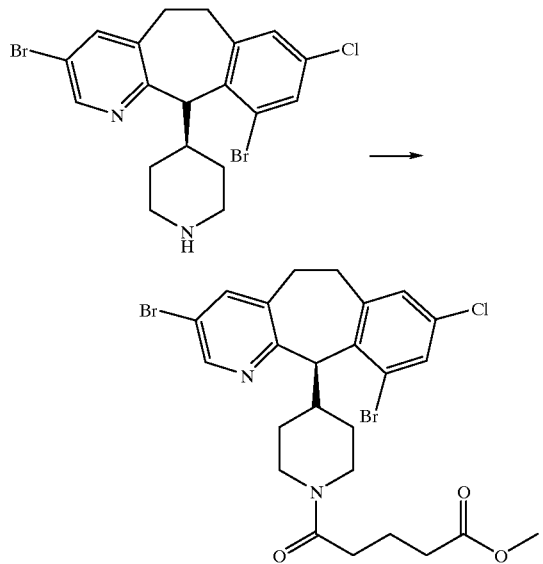

The title compound is prepared following essentially the same procedure as described for Example 45 using the appropriate diacid monoester to obtain the title compound as a white solid (yield=94%, m.p.=74–75° C., MH$^+$=599).

EXAMPLE 52

(+)-SODIUM 4-(3,10-DIBROMO-8-CHLORO-6,11-DIHYDRO-5H-BENZO[5,6]CYCLO-HEPTA[1,2-b]PYRIDIN-11(R)-YL)-DELTA-OXO-1-PIPERIDININE PENTANOATE

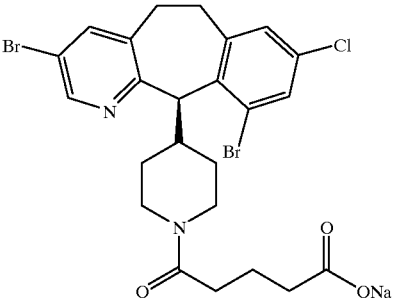

The title compound is prepared from the product of Example 51 following essentially the same procedure as described for Example 46 to obtain the title compound as a white solid (93% yield, m.p.=282° C. (decomposed), MH$^+$=584).

EXAMPLE 53

(+)-4-(3,10-DIBROMO-8-CHLORO-6,11-DIHYDRO-5H-BENZO[5,6]CYCLO-HEPTA[1,2-b]PYRIDIN-11(R)-YL)-DELTA-OXO-1-PIPERIDININE PENTANAMIDE

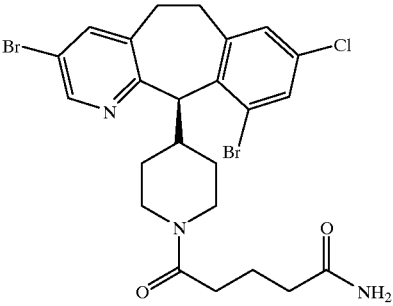

The title compound is prepared form the product of Example 52 following essentially the same procedure as described for Example 47 to obtain the title compound as a white solid (yield=61%, m.p.=124–125° C., MH$^+$=584).

EXAMPLE 54

(+)-METHYL 4-(3,10-DIBROMO-8-CHLORO-6, 11-DIHYDRO-5H-BENZO[5,6]CYCLO-HEPTA[1, 2-b]PYRIDIN-11(R)-YL)-EPSILON-OXO-1-PIPERIDININE HEXANOATE

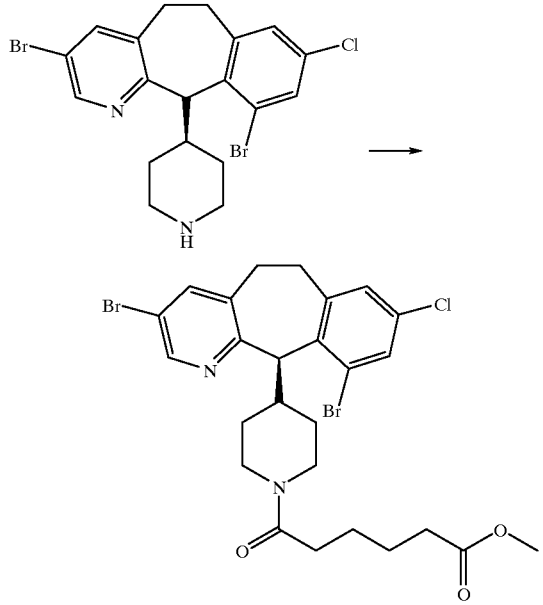

The title compound is prepared following essentially the same procedure as described for Example 45 using the appropriate diacid monoester to obtain the title compound as a white solid (yield=92%, m.p.=84–85° C., MH$^+$=613).

EXAMPLE 55

(+)-SODIUM 4-(3,10-DIBROMO-8-CHLORO-6, 11-DIHYDRO-5H-BENZO[5,6]CYCLO-HEPTA[1, 2-b]PYRIDIN-11(R)-YL)-EPSILON-OXO-1-PIPERIDININE HEXANOATE

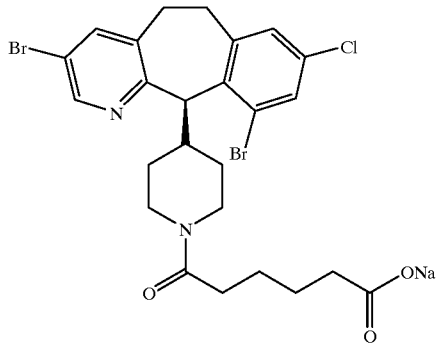

The title compound is prepared from the product of Example 54 following essentially the same procedure as described for Example 46 to obtain the title compound as a white solid (97% yield, m.p.=135–136° C., MH$^+$=598).

EXAMPLE 56

(+)-4-(3,10-DIBROMO-8-CHLORO-6,11-DIHYDRO-5H-BENZO[5,6]CYCLO-HEPTA[1,2-b]PYRIDIN-11(R)-YL)-EPSILON-OXO-1-PIPERIDININE HEXANAMIDE

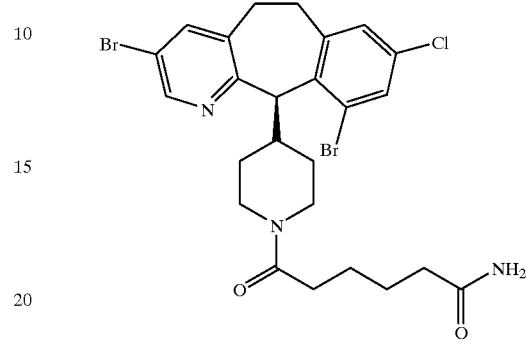

The title compound is prepared from the product of Example 55 following essentially the same procedure as described for Example 47 to obtain the title compound as a white solid (38% yield, m.p.=119–120° C., MH$^+$=598).

EXAMPLE 57

(+)-METHYL 4-(3,10-DIBROMO-8-CHLORO-6, 11-DIHYDRO-5H-BENZO[5,6]CYCLO-HEPTA[1, 2-b]PYRIDIN-11(R)-YL)-OMEGA-OXO-1-PIPERIDININE HEPTANOATE

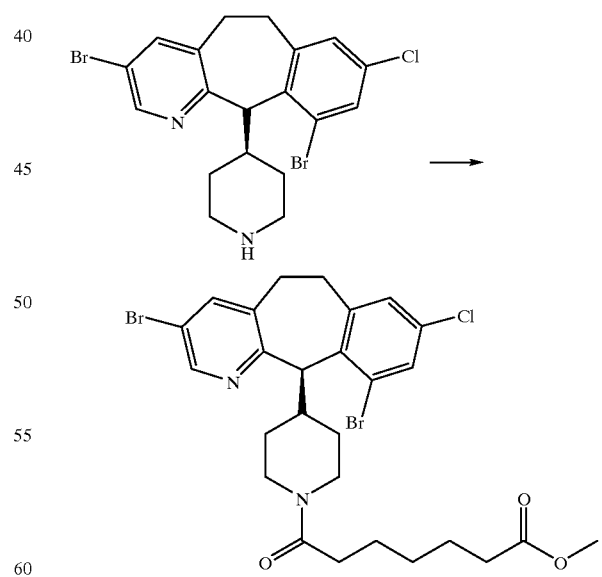

The title compound is prepared following essentially the same procedure as described for Example 45, using the appropriate diacid monoester to obtain the title compound as as an oil (yield=97%, MH$^+$=627).

EXAMPLE 58

(+)-SODIUM 4-(3,10-DIBROMO-8-CHLORO-6, 11-DIHYDRO-5H-BENZO[5,6]CYCLO-HEPTA[1, 2-b]PYRIDIN-11(R)-YL)-OMEGA-OXO-1-PIPERIDININE HEPTANOATE

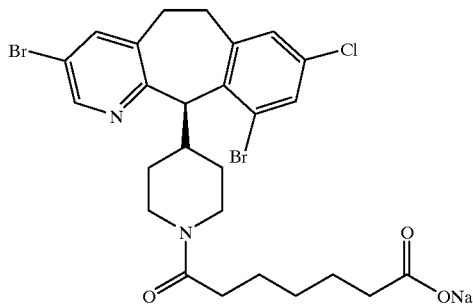

The title compound is prepared from the product of Example 57 following essentially the same procedure as described for Example 46 to obtain the title compound as a white solid (yield=82%, m.p.=142–143° C., MH$^+$=613).

EXAMPLE 59

(+)-4-(3,10-DIBROMO-8-CHLORO-6,11-DIHYDRO-5H-BENZO[5,6]CYCLO-HEPTA[1,2-b]PYRIDIN-11(R)-YL)-OMEGA-OXO-1-PIPERIDININE HEPTANAMIDE

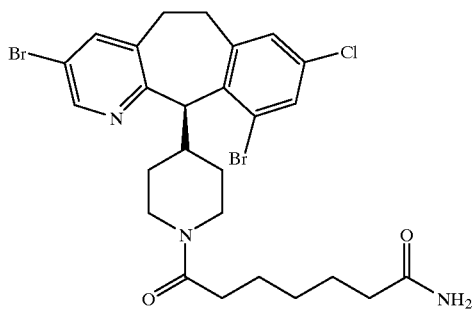

The title compound is prepared from the product of Example 58 following essentially the same procedure as described for Example 47 to obtain the title compound as a white solid (yield=30%, m.p.=96–97° C., MH$^+$=612).

EXAMPLE 60

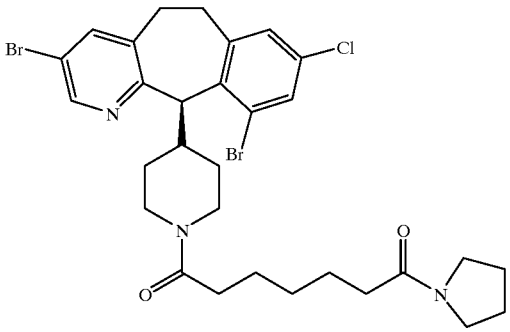

The title compound is prepared from the product of Example 58 following essentially the same procedure as described for Example 47, using the appropriate amine to obtain the title compound.

EXAMPLE 61

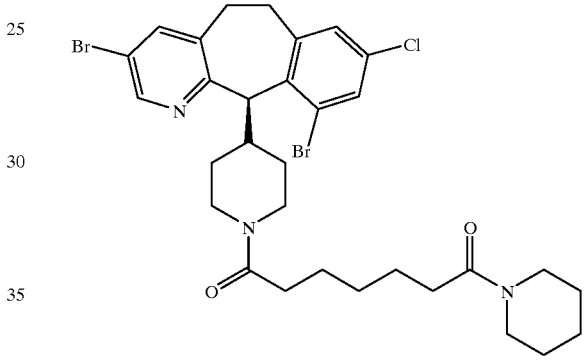

The title compound is prepared from the product of Example 58 following essentially the same procedure as described for Example 47, using the appropriate amine to obtain the title compound.

EXAMPLE 62

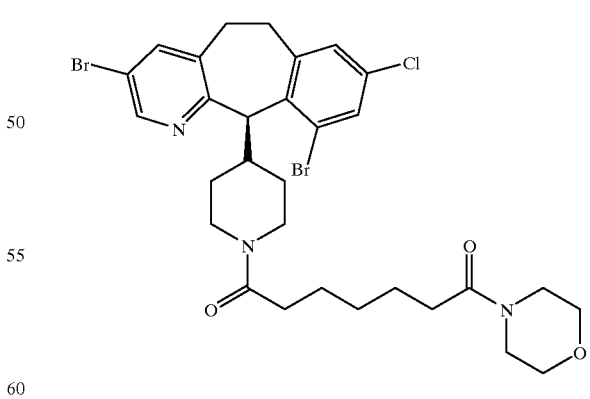

The title compound is prepared from the product of Example 58 following essentially the same procedure as described for Example 47, using the appropriate amine to obtain the title compound.

PHARMACEUTICAL DOSAGE FORM EXAMPLES

EXAMPLE A

Tablets

| No. | Ingredients | mg/tablet | mg/tablet |
|-----|-------------|-----------|-----------|
| 1. | Active compound | 100 | 500 |
| 2. | Lactose USP | 122 | 113 |
| 3. | Corn Starch, Food Grade, as a 10% paste in Purified Water | 30 | 40 |
| 4. | Corn Starch, Food Grade | 45 | 40 |
| 5. | Magnesium Stearate | 3 | 7 |
| | Total | 300 | 700 |

Method of Manufacture

Mix Item Nos. 1 and 2 in a suitable mixer for 10–15 minutes. Granulate the mixture with Item No. 3. Mill the damp granules through a coarse screen (e.g., ¼", 0.63 cm) if necessary. Dry the damp granules. Screen the dried granules if necessary and mix with Item No. 4 and mix for 10–15 minutes. Add Item No. 5 and mix for 1–3 minutes. Compress the mixture to appropriate size and weigh on a suitable tablet machine.

EXAMPLE B

Capsules

| No. | Ingredient | mg/capsule | mg/capsule |
|-----|------------|------------|------------|
| 1. | Active compound | 100 | 500 |
| 2. | Lactose USP | 106 | 123 |
| 3. | Corn Starch, Food Grade | 40 | 70 |
| 4. | Magnesium Stearate NF | 7 | 7 |
| | Total | 253 | 700 |

Method of Manufacture

Mix Item Nos. 1, 2 and 3 in a suitable blender for 10–15 minutes. Add Item No. 4 and mix for 1–3 minutes. Fill the mixture into suitable two-piece hard gelatin capsules on a suitable encapsulating machine.

While the present invention has been described in conjunction with the specific embodiments set forth herein, many alternatives, modifications and variations thereof will be apparent to those of ordinary skill in the art. All such alternatives, modifications and variations are intended to fall within the spirit and scope of the present invention.

We claim:

1. A compound of the formula

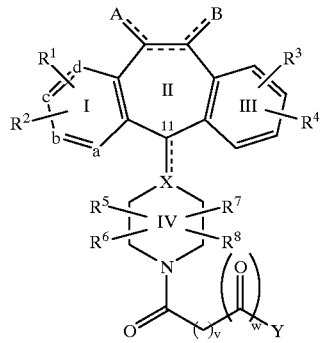

wherein:

X is CH or C when the double bond is present at the C-11 position;

one of a, b, c and d represents N or $NR^9$ wherein $R^9$ is $O^-$, $-CH_3$ or $-(CH_2)_nCO_2H$ wherein n is 1 to 3, and the remaining a, b, c and d groups represent $CR^1$ or $CR^2$; or each of a, b, c, and d are independently selected from $CR^1$ or $CR^2$;

$R^1$ is H;

$R^2$ is Br;

$R^3$ and $R^4$ are each independently selected from the group consisting of Br and Cl;

$R^5$, $R^6$, $R^7$ and $R^8$ each independently represents H, $-CF_3$, $-COR^{10}$, alkyl or aryl, said alkyl or aryl optionally being substituted with $-OR^{10}$, $-SR^{10}$, $-S(O)_tR^{11}$, $-NR^{10}COOR^{11}$, $-N(R^{10})_2$, $-NO_2$, $-COR^{10}$, $-OCOR^{10}$, $-OCO_2R^{11}$, $-CO_2R^{10}$, $OPO_3R^{10}$, or $R^5$ is combined with $R^6$ to represent $=O$ or $=S$ and/or $R^7$ is combined with $R^8$ to represent $=O$ or $=S$;

$R^{10}$ represents H, alkyl, aryl, or aralkyl;

$R^{11}$ represents alkyl or aryl;

the dotted line between carbon atoms 5 and 6 represents an optional double bond, such that when a double bond is present, A and B independently represent $-R^{10}$, halo, $-OR^{11}$, $-OCO_2R^{11}$ or $-OC(O)R^{10}$, and when no double bond is present between carbon atoms 5 and 6, A and B each independently represent $H_2$, $-(OR^{11})_2$; H and halo, dihalo, alkyl and H, $(alkyl)_2$, $-H$ and $-OC(O)R^{10}$, H and $-OR^{10}$, $=O$, aryl and H, $=NOR^{10}$ or $-O-(CH_2)_p-O-$ wherein p is 2, 3 or 4;

v is 0 to 5;

w is 0 or 1;

Y is

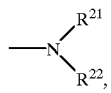

$-O-C_1-C_6$-alkyl or $-OM+$, wherein M+ is an alkali metal cation;

$R^{21}$ and $R^{22}$ are each independently H, $C_1$–$C_6$ alkyl, —$CH_2CONH_2$, phenyl, benzyl, —$SO_2$—($C_1$–$C_6$-alkyl), —NH-phenyl, acyl, $C_3$–$C_6$ cycloalkyl, pyridyl, chloro-phenyl,

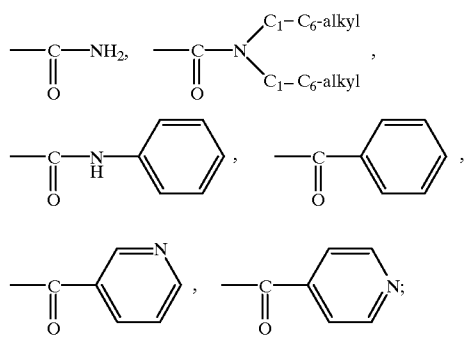

or $R^{21}$ and $R^{22}$ taken together with the nitrogen to which they are attached form

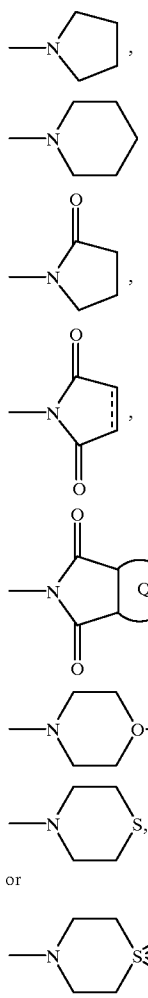

a dashed line means an optional chemical bond; wherein Q is benzene, pyridine, pyrazine, or thiophene; or a pharmaceutically acceptable salt thereof.

2. The compound according to claim 1, of the formula

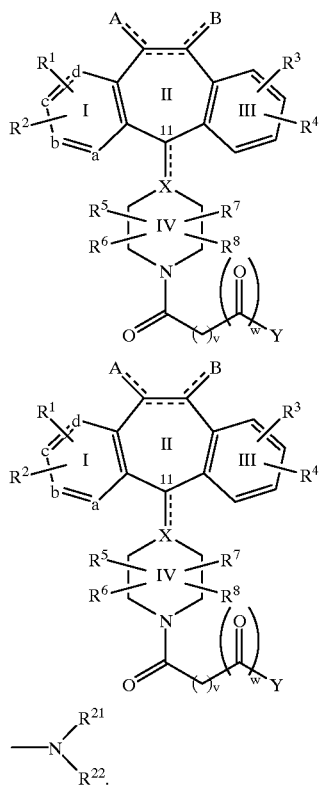

wherein v is 0 to 4; w is 0; and Y is

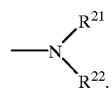

3. The compound according to claim 1 wherein a is N.

4. A compound according to claim 3 wherein X is CH.

5. The compound of claim 1 wherein w is 1; v is 0–5; $R^1$ is H; $R^2$ is Br; $R^5$–$R^8$ are each H; X is CH; and Y is —O—$C_1$–$C_6$ alkyl, $NH_2$ or —OM+.

6. A compound selected from the group consisting of

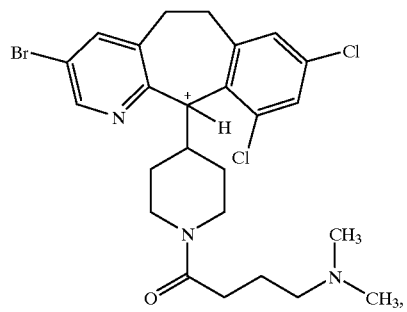

-continued
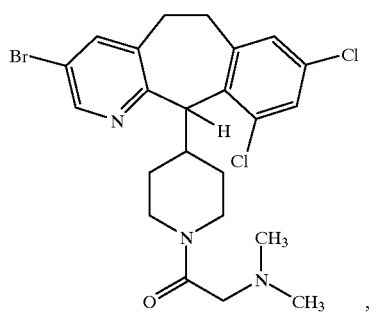
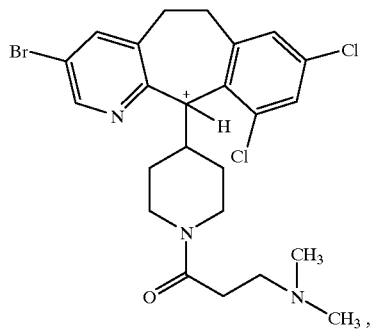
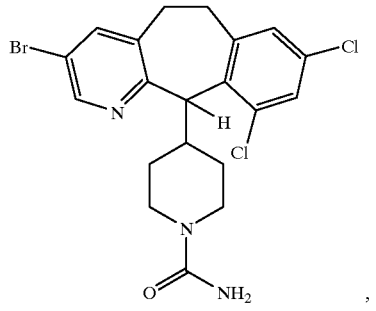
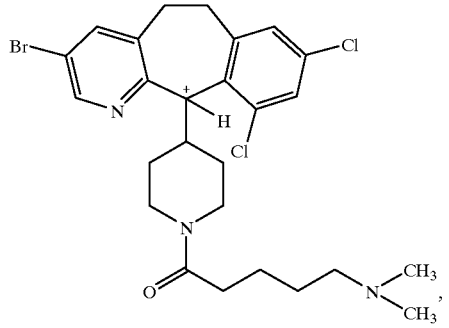
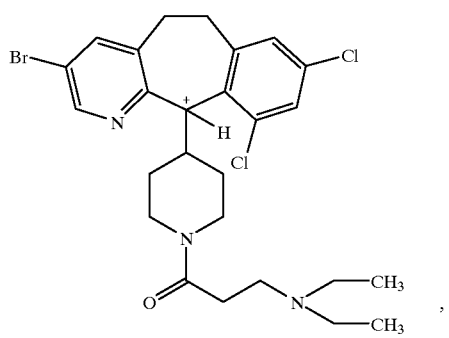
-continued
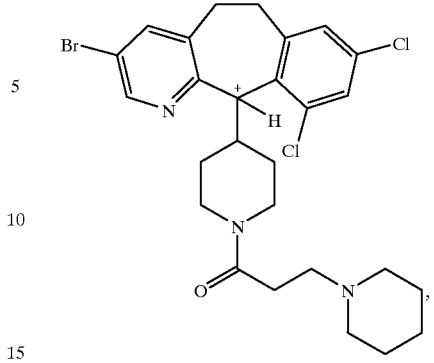
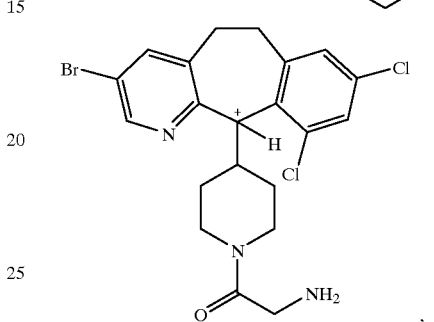
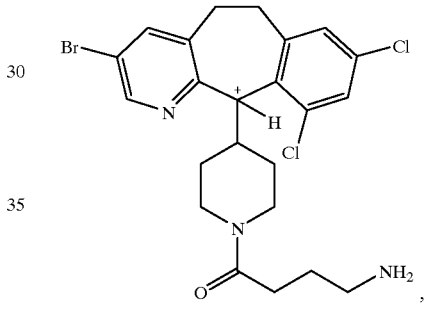
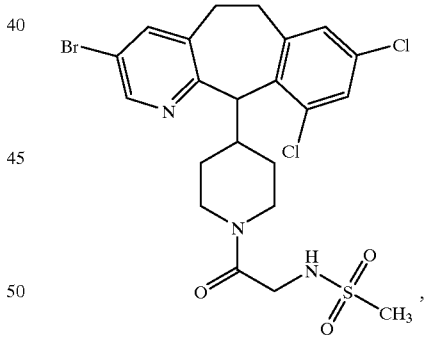
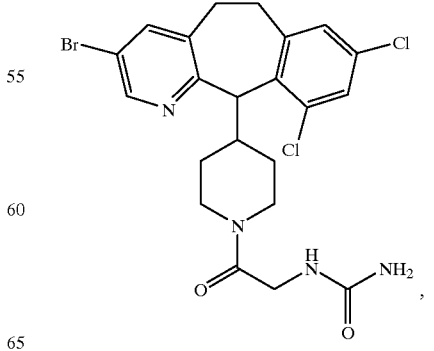

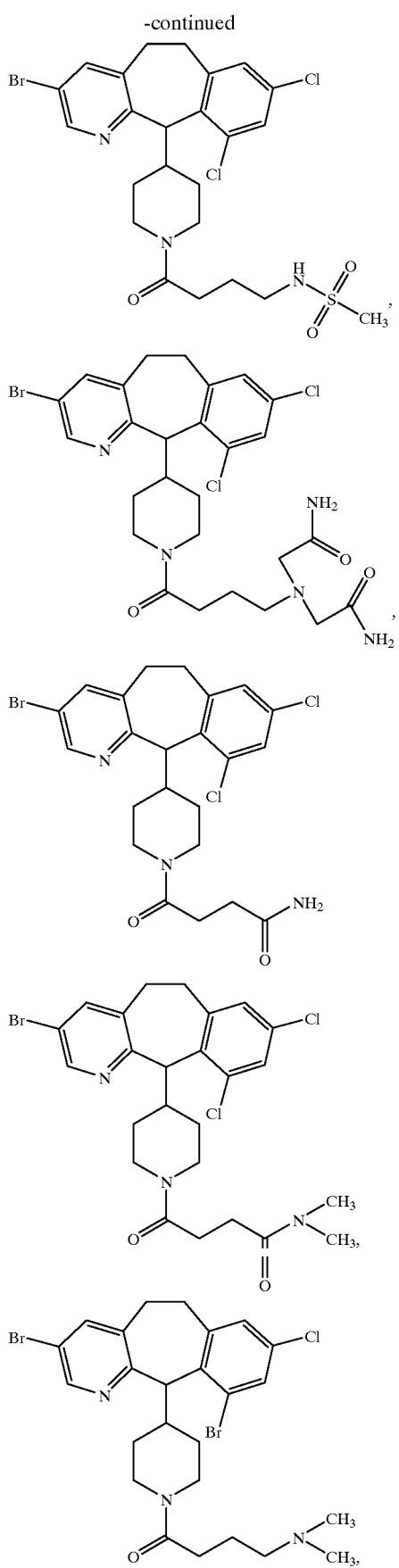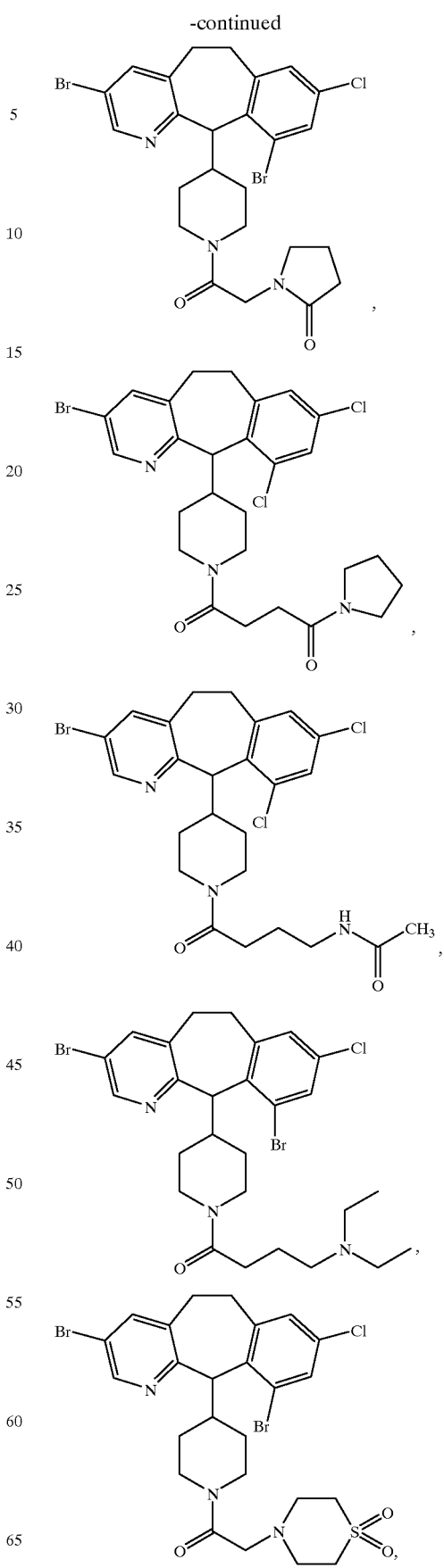

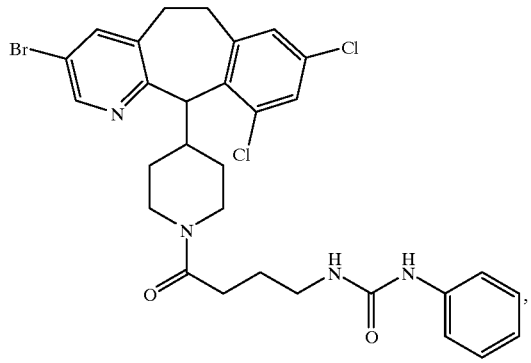
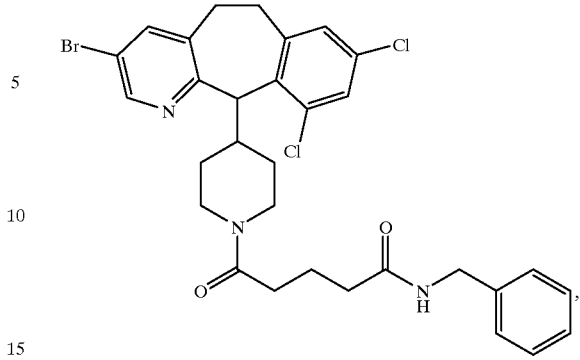
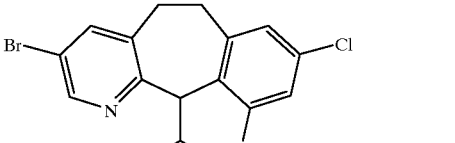
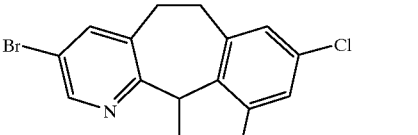
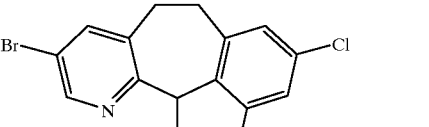

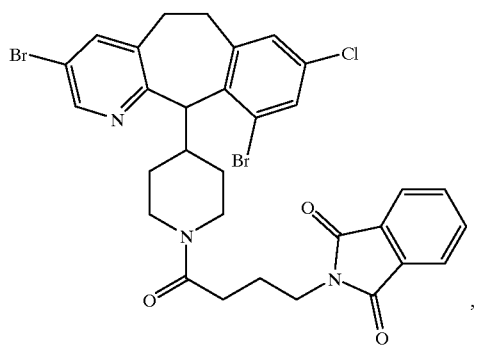,
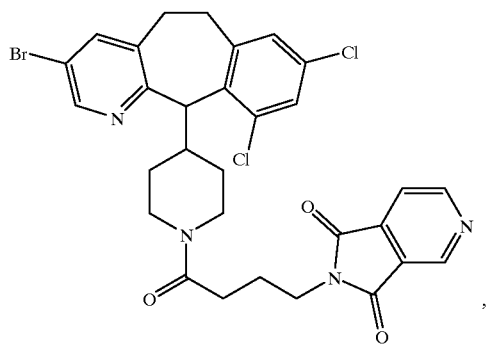,
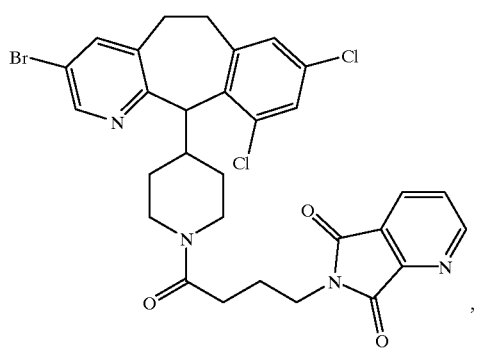,
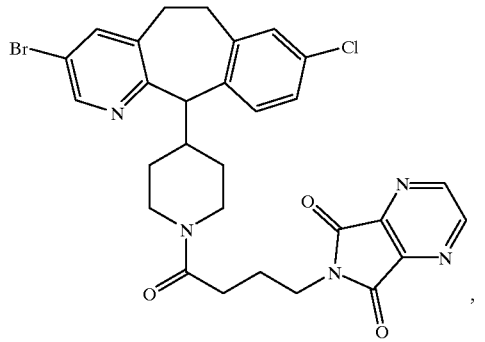,
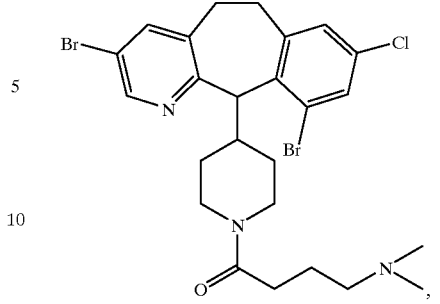,
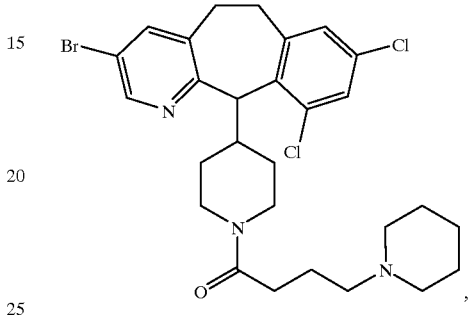,
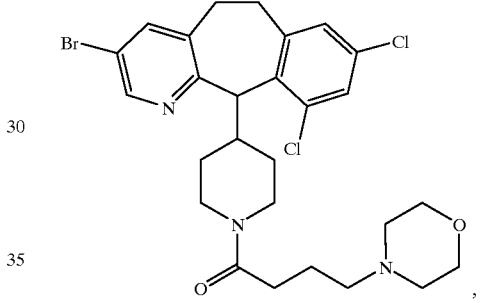,
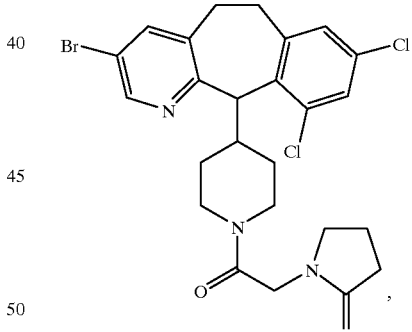,
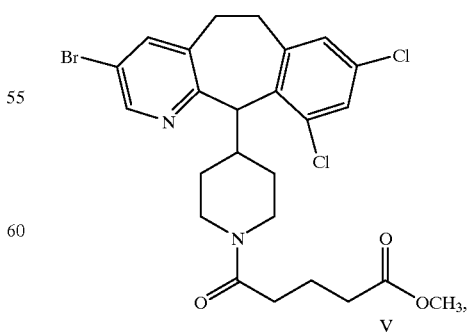

91
-continued
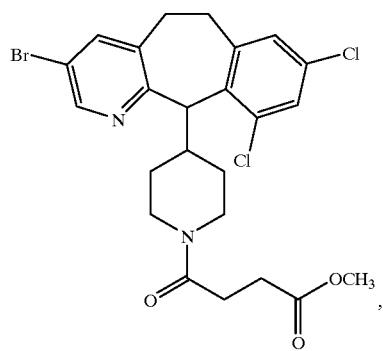
,
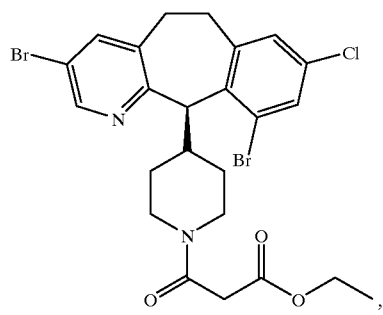
,
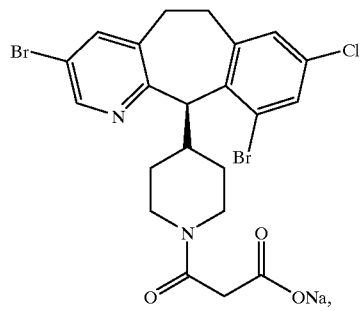
,
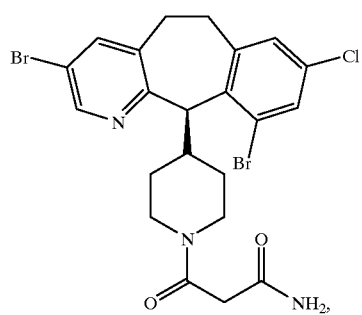
,
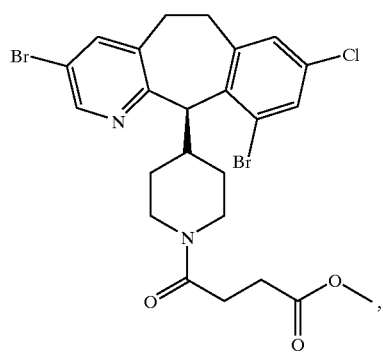
,
92
-continued
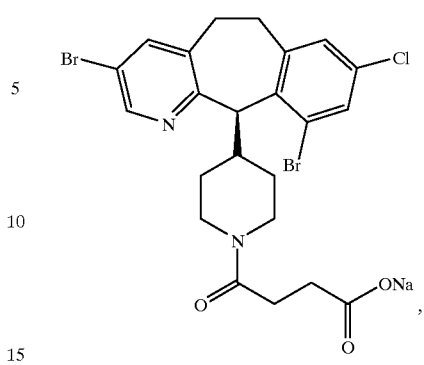
,
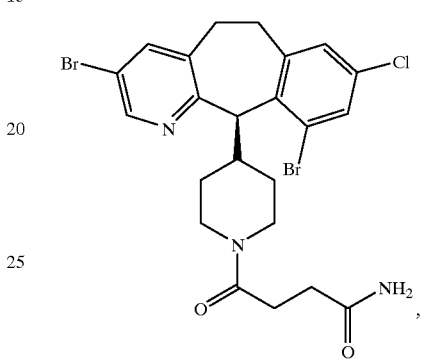
,
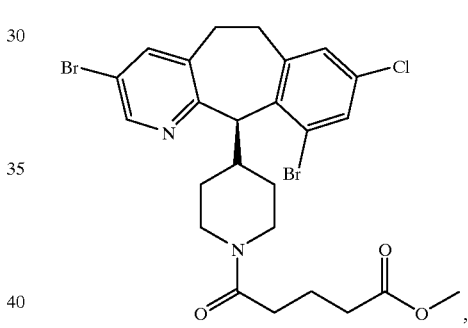
,
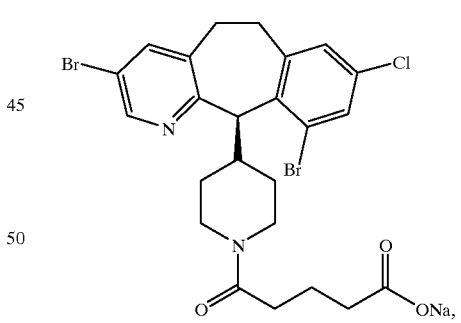
,
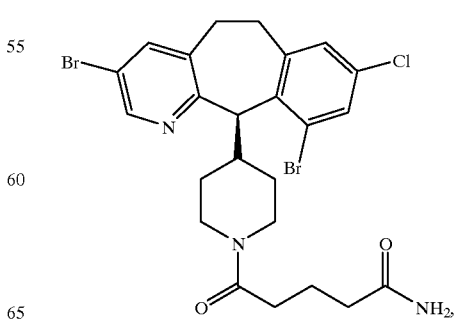

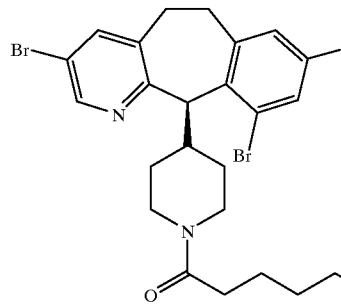
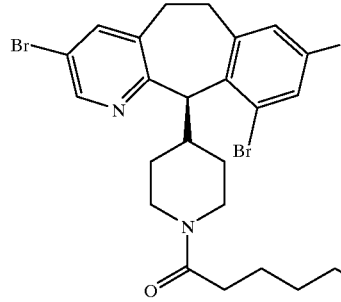
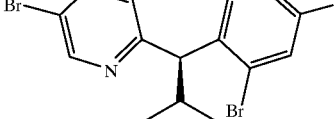

or a pharmaceutically acceptable salt thereof.

7. A method of treating tumor cells expressing an activated ras oncogene comprising administering an effective amount of a compound of claim 1.

8. The method of claim 7 wherein the cells treated are pancreatic tumor cells, breast cancer cells, prostate cancer cells, lung cancer cells, myeloid leukemia tumor cells, thyroid follicular tumor cells, myelodysplastic tumor cells, epidermal carcinoma tumor cells, bladder carcinoma tumor cells or colon tumors cells.

9. The method of claim 7 wherein the inhibition is of tumor cells wherein the Ras protein is activated as a result of oncogenic mutation in genes other than the Ras gene.

10. A method of inhibiting farnesyl protein transferase comprising the administration of an effective amount of the compound of claim 1.

11. A pharmaceutical composition for inhibiting the abnormal growth of cells comprising an effective amount of compound of claim 1 in combination with a pharmaceutically acceptable carrier.

12. The compound of claim 1 wherein the substituent

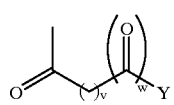

is selected from:

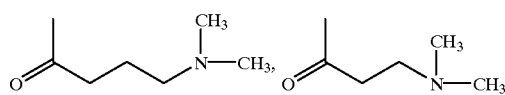

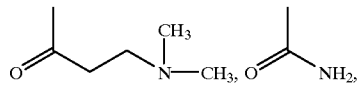

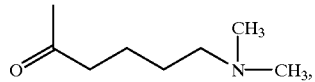

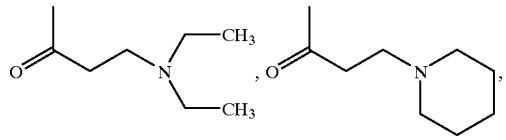

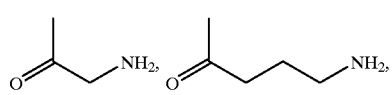

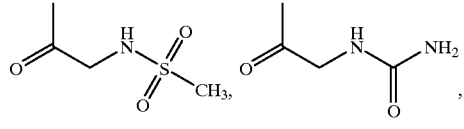

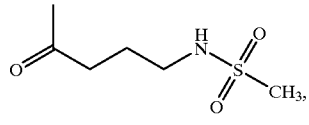

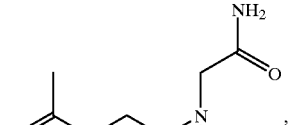

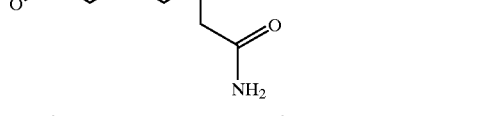

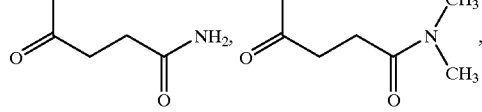

-continued

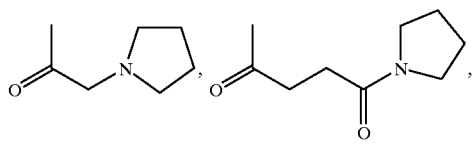

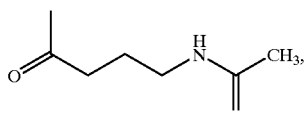

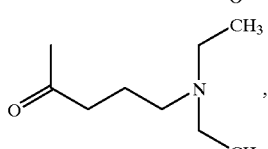

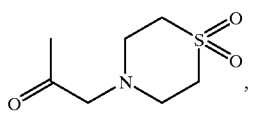

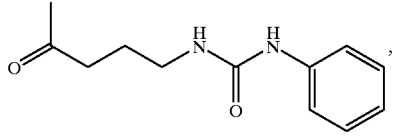

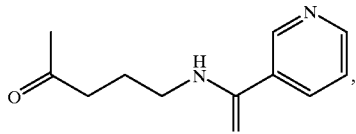

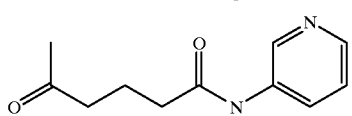

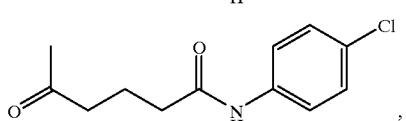

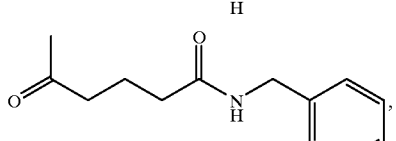

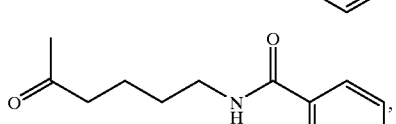

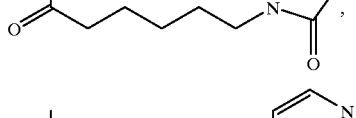

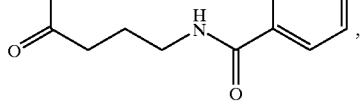

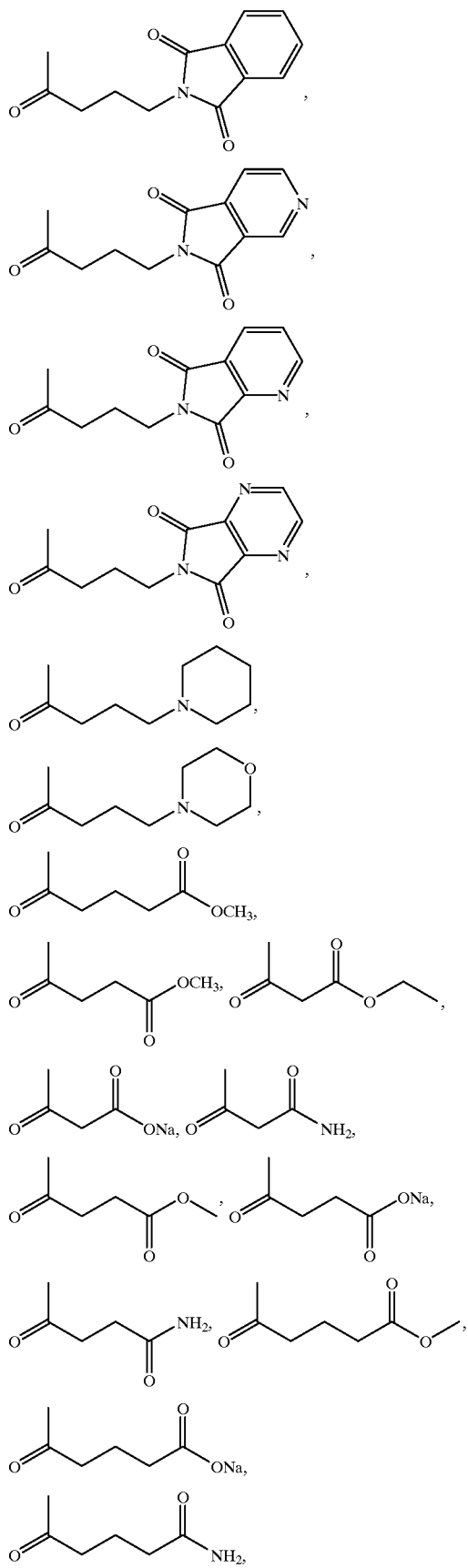
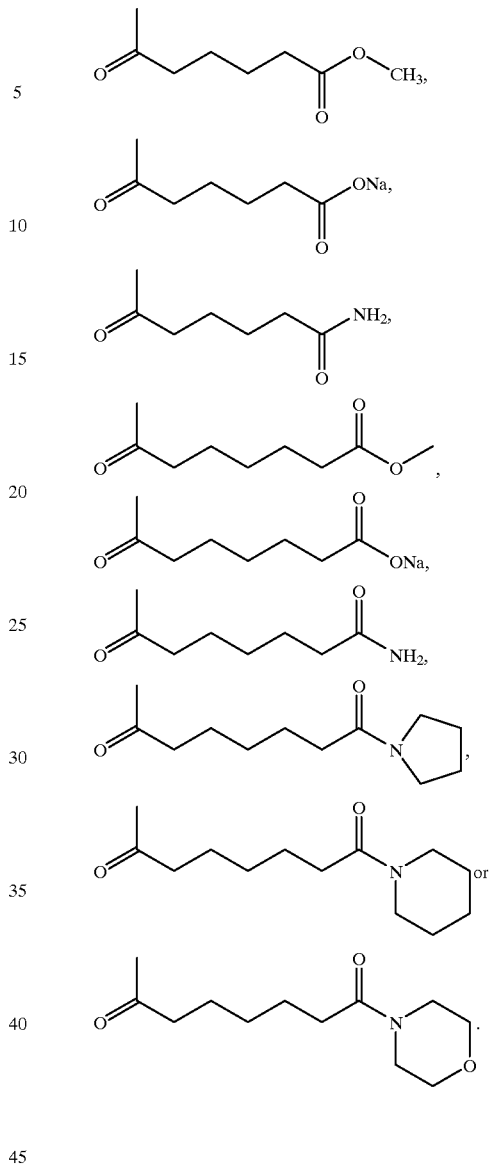
13. The compound of claim 1 wherein the substituent
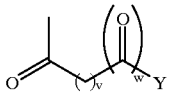
is selected from:
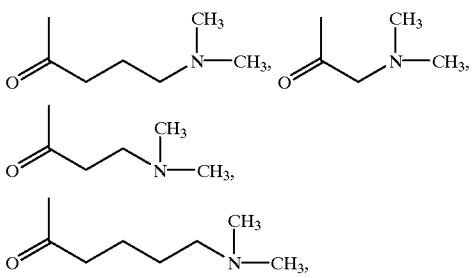

-continued
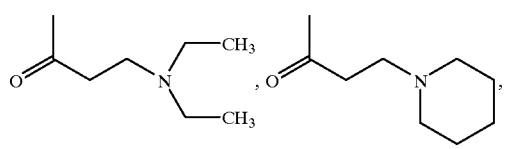
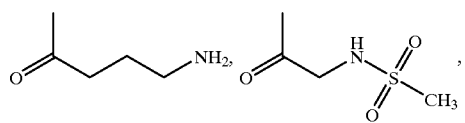
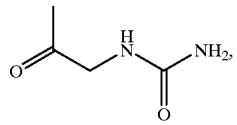
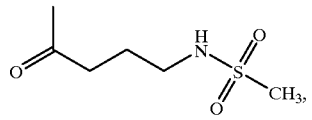
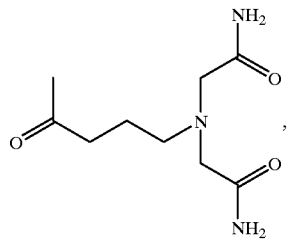
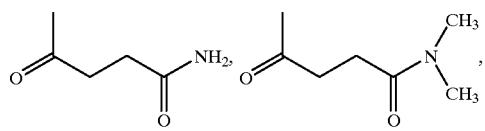
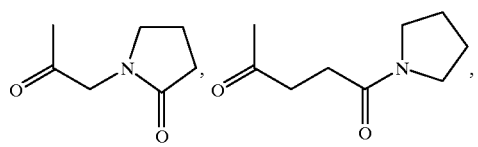
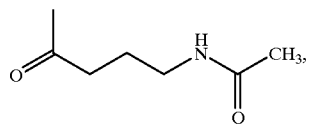
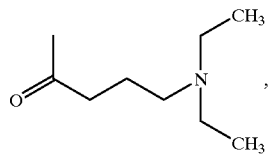
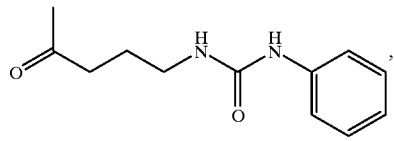
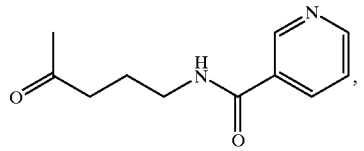
-continued
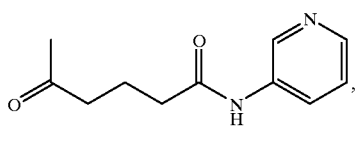
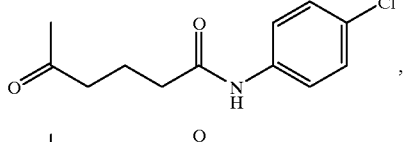
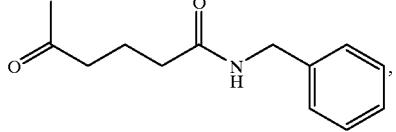
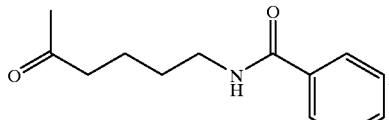
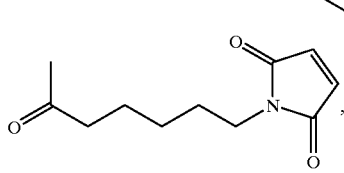
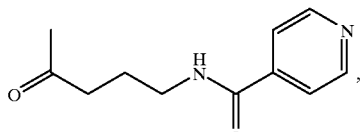
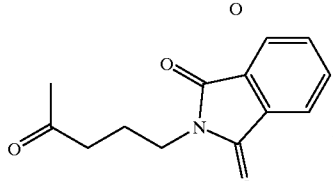
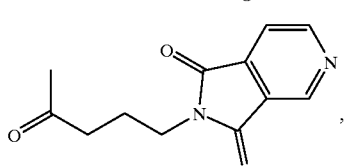
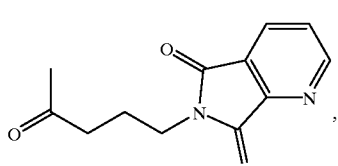
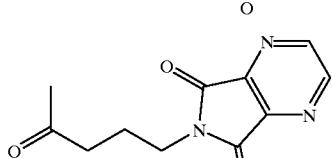
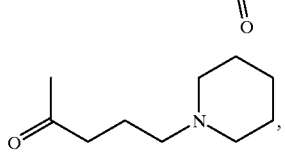

101

-continued

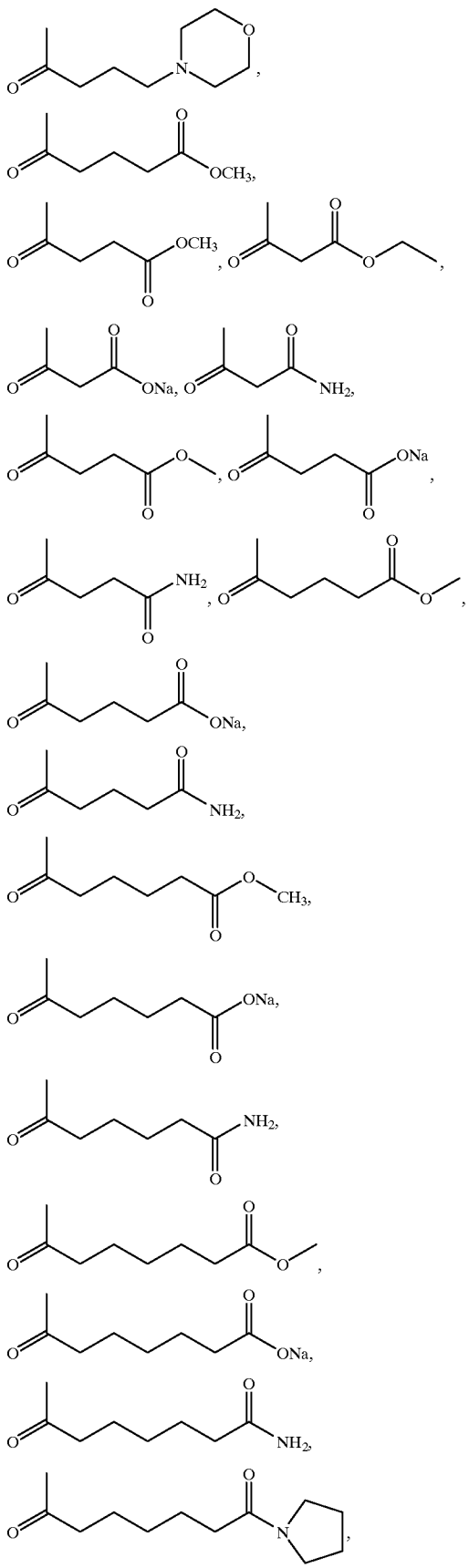

102

-continued

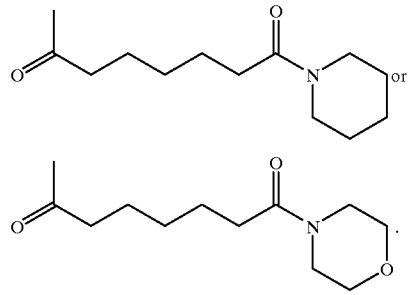

14. A compound of the formula

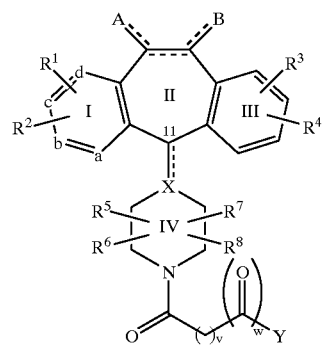

or a pharmaceutically acceptable salt thereof; wherein:

X is CH or C when the double bond is present at the C-11 position;

one of a, b, c and d represents N or NR$^9$ wherein R$^9$ is O$^-$, —CH$_3$ or —(CH$_2$)$_n$CO$_2$H wherein n is 1 to 3, and the remaining a, b, c and d groups represent CR$^1$ or CR$^2$; or each of a, b, c, and d are independently selected from CR$^1$ or CR$^2$;

each R$^1$ and each R$^2$ is independently selected from H, halo, —CF$_3$, —OR$^{10}$ (e.g., —OCH$_3$), —COR$^{10}$, —SR$^{10}$ (e.g., —SCH$_3$ and —SCH$_2$C$_6$H$_5$), —S(O)$_t$R$^{11}$ (wherein t is 0, 1 or 2, e.g., —SOCH$_3$ and —SO$_2$CH$_3$), —SCN, —N(R$^{10}$)$_2$, —NR$^{10}$R$^{11}$, —NO$_2$, —OC(O)R$^{10}$, —CO$_2$R$^{10}$, —OCO$_2$R$^{11}$, —CN, —NHC(O)R$^{10}$, —NHSO$_2$R$^{10}$, —CONHR$^{10}$, —CONHCH$_2$CH$_2$OH, —NR$^{10}$COOR$^{11}$,

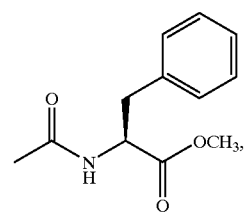

—SR$^{11}$C(O)OR$^{11}$ (e.g., —SCH$_2$CO$_2$CH$_3$), —SR$^{11}$N(R$^{12}$)$_2$ wherein each R$^{12}$ is independently selected from H and —C(O)OR$^{11}$ (e.g., —S(CH$_2$)$_2$NHC(O)O-t-butyl and —S(CH$_2$)$_2$NH$_2$), benzotriazol-1-yloxy, tetrazol-5-ylthio, or substituted tetrazol-5-ylthio (e.g., alkyl substituted tetrazol-5-ylthio such as 1-methyl-tetrazol-5-ylthio), alkynyl, alkenyl or alkyl, said alkyl or alkenyl group optionally being substituted with halo, —OR$^{10}$ or —CO$_2$R$^{10}$;

$R^3$ and $R^4$ are the same or different and each independently represents H, any of the substituents of $R^1$ and $R^2$, or $R^3$ and $R^4$ taken together represent a saturated or unsaturated $C_5$–$C_7$ fused ring to the benzene ring (Ring III);

$R^5$, $R^6$, $R^7$ and $R^8$ each independently represents H, —$CF_3$, —$COR^{10}$, alkyl or aryl, said alkyl or aryl optionally being substituted with —$OR^{10}$, —$SR^{10}$, —$S(O)_tR^{11}$, —$NR^{10}COOR^{11}$, —$N(R^{10})_2$, —$NO_2$, —$COR^{10}$, —$OCOR^{10}$, —$OCO_2R^{11}$, —$CO_2R^{10}$, $OPO_3R^{10}$, or $R^5$ is combined with $R^6$ to represent =O or =S and/or $R^7$ is combined with $R^8$ to represent =O or =S;

$R^{10}$ represents H, alkyl, aryl, or aralkyl;

$R^{11}$ represents alkyl or aryl;

the dotted line between carbon atoms 5 and 6 represents an optional double bond, such that when a double bond is present, A and B independently represent —$R^{10}$, halo, —$OR^{11}$, —$OCO_2R^{11}$ or —$OC(O)R^{10}$, and when no double bond is present between carbon atoms 5 and 6, A and B each independently represent $H_2$, —$(OR^{11})_2$; H and halo, dihalo, alkyl and H, (alkyl)$_2$, —H and —$OC(O)R^{10}$, H and —$OR^{10}$, =O, aryl and H, =$NOR^{10}$ or —O—$(CH_2)_p$—O— wherein p is 2, 3 or 4; and the substituent

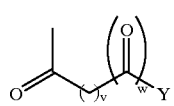

is selected from:

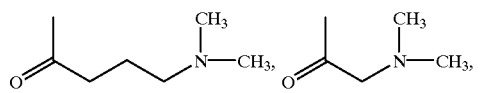

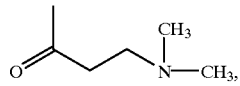

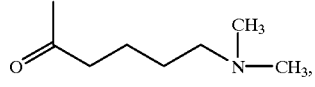

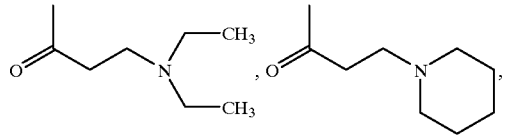

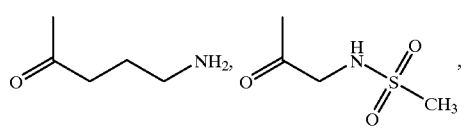

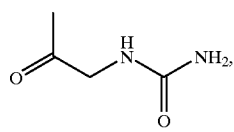

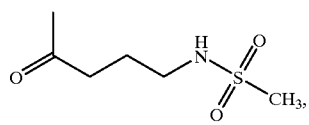

-continued

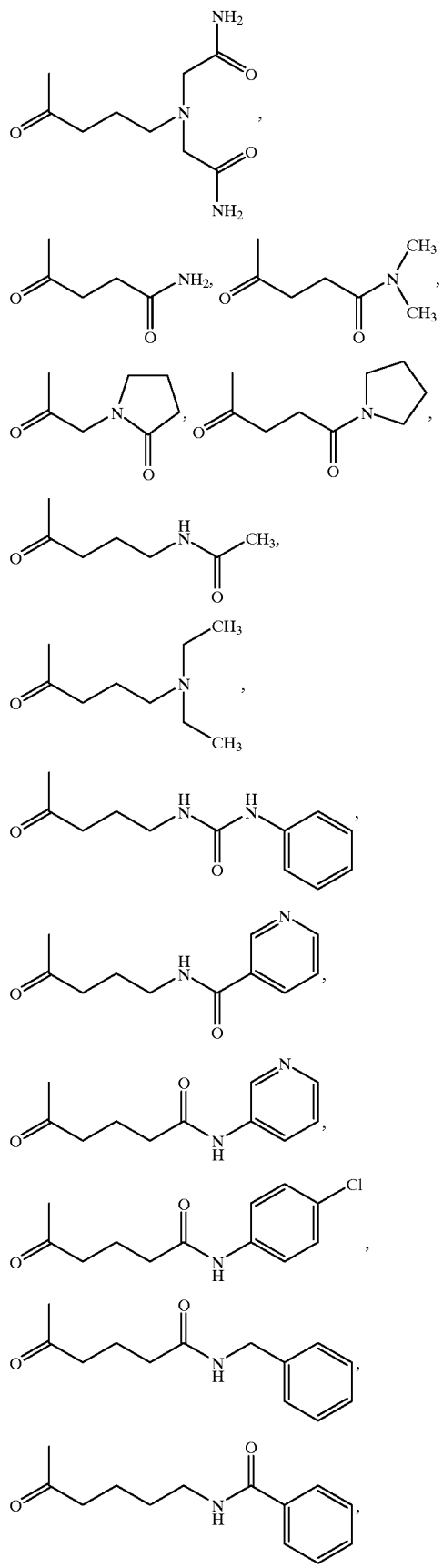

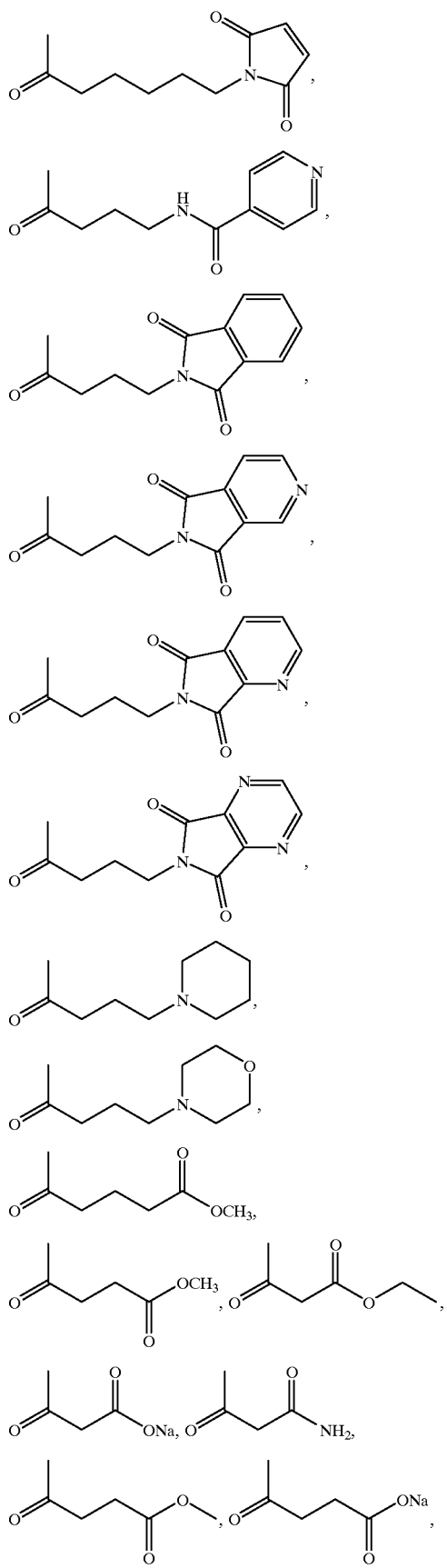
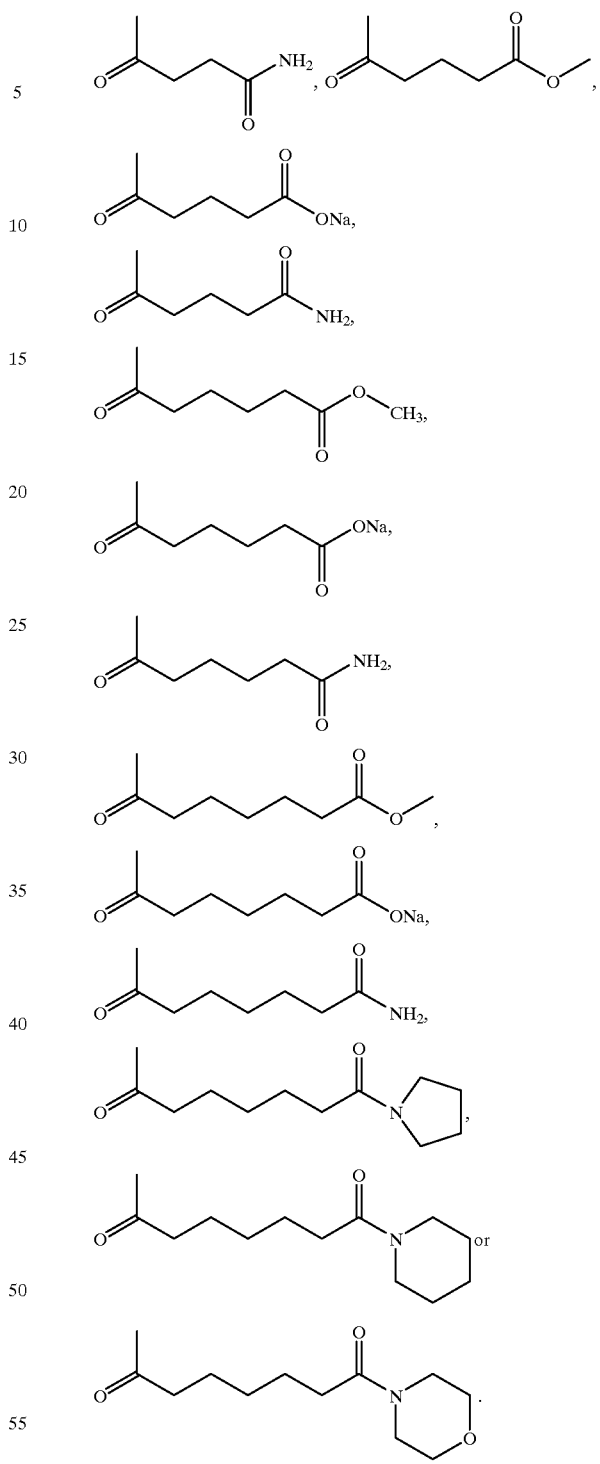
15. The compound of claim 14 wherein X is CH.
16. The compound of claim 15 wherein a is N.
17. A pharmaceutical composition comprising a compound of claim 14 and a pharmaceutically acceptable carrier.

18. A method of inhibiting farnesyl protein transferase comprising the administration of an effective amount of a compound of claim 14.

19. A method of treating pancreatic tumor cells, breast cancer cells, prostate cancer cells, lung cancer cells, myeloid leukemia tumor cells, thyroid follicular tumor cells, myelodysplastic tumor cells, epidermal carcinoma tumor cells, bladder carcinoma tumor cells or colon tumors cells comprising administering an effective amount of a compound of claim 14.

* * * * *